United States Patent [19]

Floyd et al.

[11] Patent Number: 4,902,684
[45] Date of Patent: Feb. 20, 1990

[54] BENZAZEPINE AND BENZOTHIAZEPINE DERIVATIVES

[75] Inventors: David M. Floyd, Pennington; John T. Hunt, Princeton; Spencer D. Kimball, East Windsor; John Krapcho, Somerset; Jagabandhu Das, Hamilton Square; George C. Rovnyak, Hopewell, all of N.J.; Joel C. Barrish, Holland, Pa.

[73] Assignee: E. R. Squibb & Sons, Inc., Princeton, N.J.

[21] Appl. No.: 353,806

[22] Filed: May 22, 1989

Related U.S. Application Data

[63] Continuation-in-part of Ser. No. 208,521, Jun. 20, 1988, abandoned.

[51] Int. Cl.[4] .................. A61K 31/55; C07D 281/10; C07D 223/16
[52] U.S. Cl. .................................. 514/211; 514/213; 540/491; 540/523
[58] Field of Search ............... 540/523, 491; 514/213, 514/211

[56] References Cited

U.S. PATENT DOCUMENTS

| | | | |
|---|---|---|---|
| 3,562,257 | 2/1971 | Kugita et al. | 540/491 |
| 4,567,175 | 1/1986 | Takeda et al. | 540/491 |
| 4,584,131 | 4/1986 | Floyd et al. | 540/491 |
| 4,590,188 | 5/1986 | Takeda et al. | 540/491 |
| 4,694,002 | 9/1987 | Floyd et al. | 540/491 |
| 4,729,994 | 3/1988 | Carson | 540/491 |
| 4,743,599 | 5/1988 | Muller et al. | 540/491 |
| 4,748,239 | 5/1988 | Floyd et al. | 540/491 |
| 4,752,645 | 6/1988 | Das et al. | 540/491 |

FOREIGN PATENT DOCUMENTS

| | | | |
|---|---|---|---|
| 0256888 | 2/1988 | European Pat. Off. | 540/491 |
| 0289241 | 11/1988 | European Pat. Off. | 540/523 |
| 292840 | 11/1988 | European Pat. Off. | 514/213 |

OTHER PUBLICATIONS

L. H. Werner, et al., "Imidazoline Derivatives with Antiarrhythmic Activity", *J. Med. Chem.*, 1967, 10, 575–582.

Primary Examiner—Robert T. Bond
Attorney, Agent, or Firm—Theodore R. Furman Jr.

[57] ABSTRACT

Vasodilating activity is exhibited by compounds having the formula

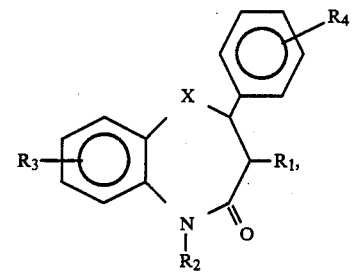

wherein
X can be —S— or —CH$_2$—; and
R$_2$ is

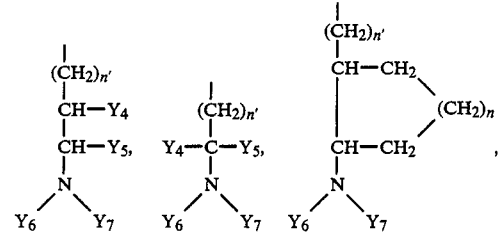

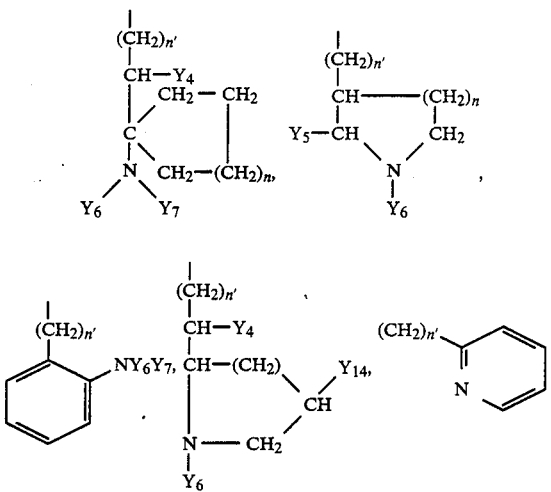

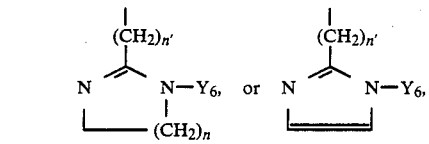

depending upon the definition of X.

43 Claims, No Drawings

BENZAZEPINE AND BENZOTHIAZEPINE DERIVATIVES

This is a continuation-in-part of U.S. Ser. No. 208,521, filed June 20, 1988, now abandoned.

BRIEF DESCRIPTION OF THE INVENTION

Compounds having the formula

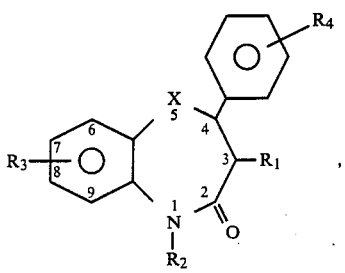

and the pharmaceutically acceptable salts thereof, have useful vasodilating activity. In formula I, and throughout the specification, the symbols are as defined below.

X is —CH$_2$— or —S—;

R$_1$ is

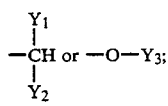

when X is —CH$_2$—, R$_2$ is

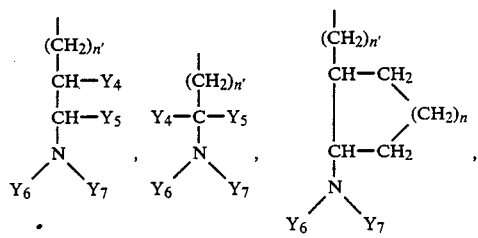

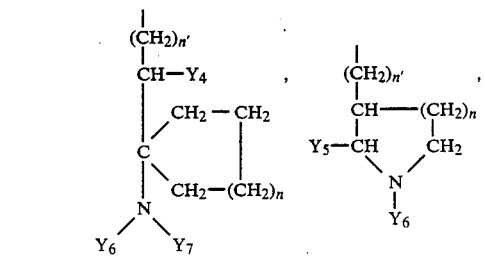

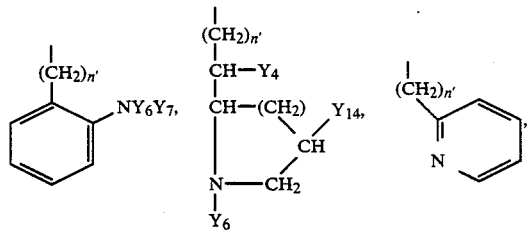

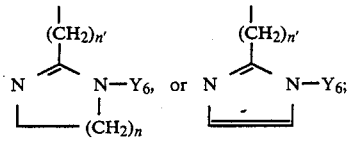

when X is —S—, R$_2$ is

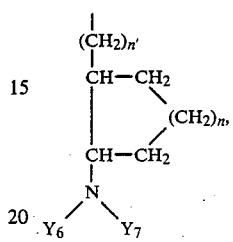

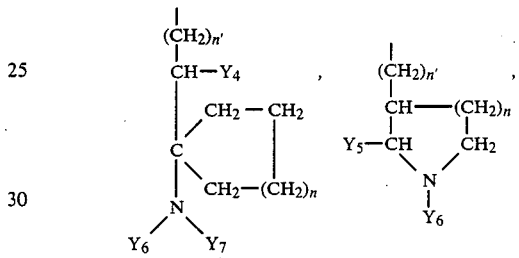

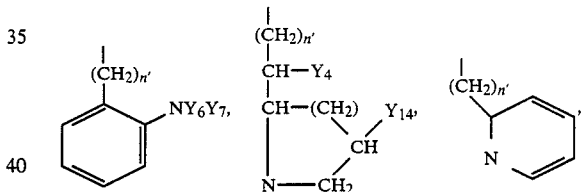

R$_3$ and R$_4$ are each independently hydrogen, halogen, alkyl, alkoxy, aryloxy, arylalkoxy, arylalkyl, cyano, hydroxy, alkanoyloxy, $$-O-\overset{\overset{O}{\|}}{C}-NY_8Y_9,$$

fluoro substituted alkoxy, fluoro substituted alkyl, (cycloalkyl)alkoxy, —NO$_2$, —NY$_{10}$Y$_{11}$, —S(O)$_m$alkyl, —S(O)$_m$aryl, $$-\overset{\overset{O}{\|}}{C}-Y_{12} \text{ or } -O-\overset{\overset{O}{\|}}{C}-Y_{13};$$

n or n' are independently 0, 1, 2 or 3;
m is 0, 1 or 2;

$Y_1$ and $Y_2$ are independently hydrogen or alkyl, $Y_1$ is hydrogen and $Y_2$ is alkenyl, alkynyl, aryl, heteroaryl, or cycloalkyl, or $Y_1$ and $Y_2$ together with the carbon atom to which they are attached are cycloalkyl;

$Y_3$ is hydrogen, alkyl, alkanoyl, alkenyl, arylcarbonyl, heteroarylcarbonyl, or

$Y_4$ and $Y_5$ are each independently hydrogen, alkyl, aryl or arylalkyl, provided that when both are present they are not both hydrogen, and provided further that when both are attached to the same carbon atom neither of them is hydrogen;

$Y_6$ and $Y_7$ are each independently hydrogen, alkyl, cycloalkyl or arylalkyl or $Y_6$ and $Y_7$ together with the nitrogen atom to which they are attached are azetidinyl, pyrrolidinyl, piperidinyl, or morpholinyl;

$Y_8$ and $Y_9$ are each independently hydrogen, alkyl, aryl or heteroaryl, or $Y_8$ and $Y_9$ together with the nitrogen atom to which they are attached are pyrrolidinyl, piperidinyl or morpholinyl;

$Y_{10}$ and $Y_{11}$ are each independently hydrogen, alkyl, alkanoyl, arylcarbonyl, heteroarylcarbonyl, or

$Y_{12}$ is hydroxy, alkoxy, aryloxy, amino, alkylamino or dialkylamino;

$Y_{13}$ is alkyl, alkoxy or aryloxy; and, $Y_{14}$ is hydroxy, alkoxy, aryloxy or arylalkoxy.

Listed below are definitions of various terms used to describe the benzazepines of this invention. These definitions apply to the terms as they are used throughout the specification (unless they are otherwise limited in specific (instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino (—NH$_2$), alkylamino, dialkylamino, nitro, halogen, hydroxyl, trifluoromethyl, alkyl (of 1 to 4 carbon atoms), alkoxy (of 1 to 4 carbon atoms), alkylthio, (of 1 to 4 carbon atoms), alkanoyloxy, carbonyl, or carboxyl groups.

The term "alkanoyl" refers to groups having the formula

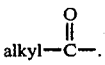

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl, oxazolyl or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The carbon atoms in the 3 and 4-positions of the benzazepine nucleus and, carbon atoms in the 2 and 3-positions of the benzothiazepine nucleus, of the compounds of formula I are asymmetric carbons. The compounds of formula I, therefore, exist in enantiomeric and diastereomeric forms and as racemic mixtures thereof. All are within the scope of this invention. It is believed that those compounds of formula I which have the cis configuration are the most potent and are therefore preferred.

DETAILED DESCRIPTION OF THE INVENTION

The compounds of formula I, and the pharmaceutically acceptable salts thereof, are cardiovascular agents. They act as calcium entry blocking vasodilators and are especially useful as antihypertensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, these compounds, in addition to being antihypertensive agents, are also useful as anti-arrhythmic agents, anti-anginal agents, anti-fibrillatory agents, anti-asthmatic agents, anti-ischemic agents, as an agent to increase the ratio of HDL-cholesterol to total serum cholesterol in the blood and in limiting myocardial infarction.

Additionally, the compounds of this invention are useful as therapy for congestive heart failure, therapy for peripheral vascular disease (e.g., Raynaud's disease), as anti-thrombotic agents, as anti-atherosclerotic agents, for treatment of cardiac hypertrophy (e.g., hypertrophic cardiomyopathy), for treatment of pulmonary hypertension, as an additive to cardioplegic solutions for cardiopulmonary bypasses and as an adjunct to thrombolytic therapy.

Compounds of this invention are also expected to be useful in the treatment of central nervous system vascular disorders, for example, as anti-stroke agents, anti-migraine agents, therapy for cerebral ischemia and therapy for subarachnoid hemorrhage, as well as in the treatment of central nervous system behavorial disorders, for example, in the treatment of psychiatric conditions including depression, mania, anxiety and schizophrenia, or for epilepsy or cognition benefit.

Further, compounds of this invention are expected to be used as anti-diarrheal agents, as therapy for dysmenorrhea, as therapy for tinnitus and other auditory and vestibulatory disorders, for the alleviation of the various forms of oedema, for reversal of adriamycin resistance, regulation of cell growth, for treatment of glaucoma, renal failure, hepatoxicity (e.g., liver cirrhosis), various endocrine hypersecretory states (e.g., diabetes, pheochromocytoma), drug-induced tardive dyskenesia, allergies, muscular dystrophy and cancer.

The compounds of this invention can also be formulated in combination with a beta-adrenergic agent, or antiarrhythmic agent, a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories). Such combination products if formulated as a fixed dose employ the compounds of this invention within the dose range described above and the other pharmaceutically active agent within its approved dose range.

The compounds of formula I can be formulated for use in the reduction of blood pressure in compositions such as tablets, capsules or elixirs for oral administration, or in sterile solutions or suspensions for parenteral administration. The compounds of formula I may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I can be prepared from the corresponding compounds having the formula

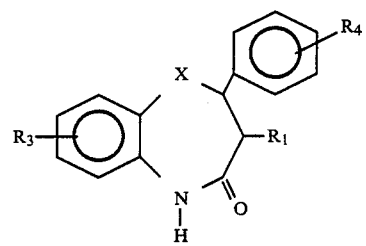

The preparation of the racemic and nonracemic forms of the compounds of formula II when X is $CH_2$ is described in U.S. Pat. No. 4,752,645 issued June 21, 1988 for those compounds wherein $R_1$ is

and in U.S. Pat. No. 4,748,239, issued May 31, 1988 for those compounds wherein $R_1$ is $-OY_3$ and $Y_3$ is hydrogen. Compounds of formula II where X is S and $R_1$ is $OY_3$ are prepared as described in U.S. Pat. No. 3,562,257 issued Feb. 9, 1971.

Compounds of formula II where X is S and $R_1$ is

are prepared as described in U.S. Pat. No. 4,694,002, issued Sept. 15, 1987. Compounds of formula II wherein $R_1$ is $-O-Y_3$ and $Y_3$ is other than hydrogen can be obtained by alkylation or acylation (using conventional techniques) of the corresponding compound of the formula II wherein $R_1$ is $-OH$.

The compounds of formula II where $R_1$ is OH can be prepared in nonracemic form by reacting the racemic compound of formula II where $R_1$ is OH with a nonracemic acid or amino acid

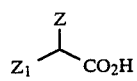

where Z and $Z_1$ are different, using conventional acylation techniques such as carbodiimide with a catalyst such as dimethylaminopyridine, to give a mixture of diastereomeric compounds II wherein $R_1$ is

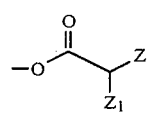

This mixture of diastereomeric compounds can be separated by those skilled in the art, using chromatographic techniques or crystallization. The nonracemic compounds of formula II where $R_1$ is OH are obtained from the purified diastereomers by hydrolysis with a base such as sodium hydroxide or sodium methoxide.

Treatment of a compound of formula II with a base (e.g., sodium hydride or cesium carbonate) in an inert solvent (e.g., dimethylformamide or dimethylsulfoxide) followed by reaction with a compound of the formula $$R_2-L \qquad \text{III}$$

(where L is a leaving group such as halo or tosyloxy) yields the corresponding product of formula I.

Alternatively, a compound of formula I can be prepared by reacting a compound of formula II with one of formula III under phase transfer conditions in a mixture of water and dichloromethane or toluene in the presence of an appropriate base (e.g., barium hydroxide or sodium hydroxide) and catalyst (e.g., benzyl trimethylammonium chloride or tetra-n-butylammonium hydrogen sulfate).

Alternatively, the products of formula I wherein $R_1$ is —OH can be alkylated or acylated (using conventional techniques) to obtain those products of formula I wherein $R_1$ is —O—$Y_3$ and $Y_3$ is other than hydrogen.

An additional procedure for preparing the compounds of formula I wherein $R_2$ is

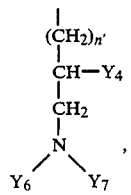

comprises treating a compound of formula II with an alkali metal hydride (e.g., sodium hydride) in an inert solvent (e.q., dimethylformamide or dimethylsulfoxide) followed by reaction with a compound of the formula

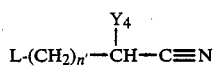   IV to obtain the corresponding compound having the formula

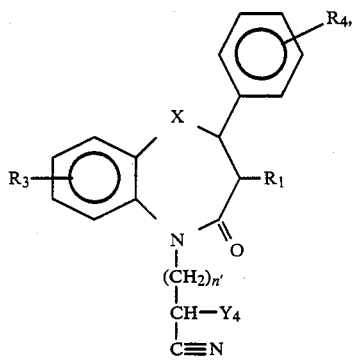   V

Reduction of a compound of formula V using, for example, catalytic hydrogenation (e.g., rhodium on alumina) yields the corresponding product of formula I having the formula

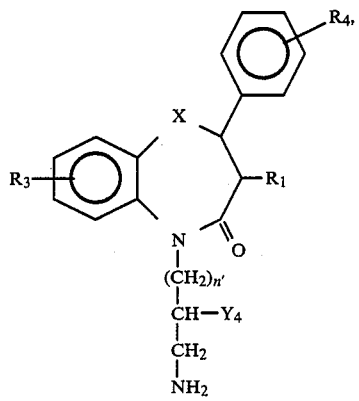   VI

Reductive amination of a compound of formula VI with the appropriate aldehyde or ketone using a chemical reducing agent (e.g., sodium cyanoborohydride) yields the corresponding product of formula I having the formula

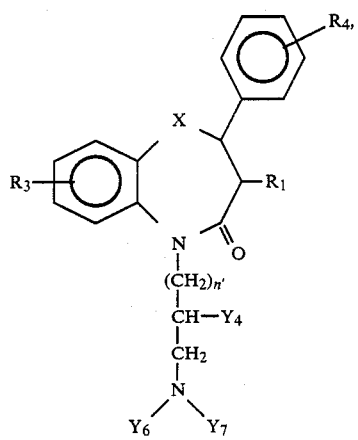   VII wherein at least one of $Y_6$ and $Y_7$ is other than hydrogen.

Alternatively, compounds of formula I wherein $R_2$ is

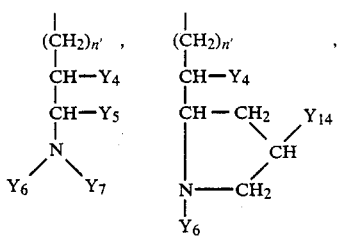

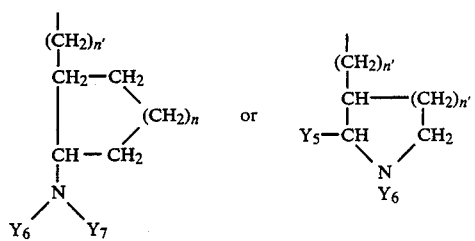 or 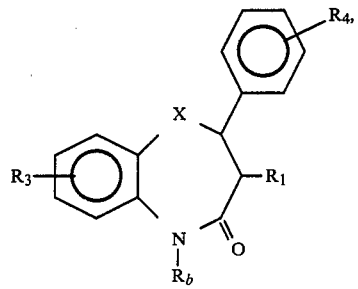

can be prepared by first treating a compound of formula II with an alkali metal hydride (e.g., sodium hydride) in an inert organic solvent (e.g., dimethylformamide or dimethylsulfoxide) followed by reaction with the appropriate compound having the formula $R_a$—L  VIII wherein $R_a$ is

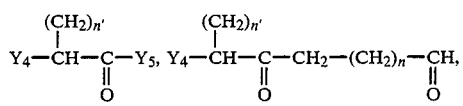

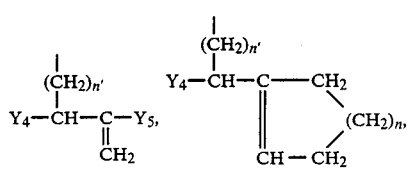

The resultant compound has the formula

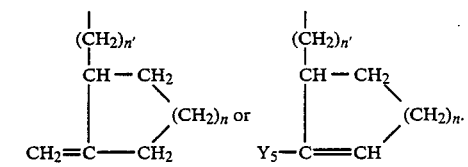  IX and can be reacted with ozone in an inert solvent (e.g., a halogenated hydrocarbon) followed by reduction (e.g., using a chemical reducing agent such as dimethylsulfide) to yield the corresponding compound having the formula

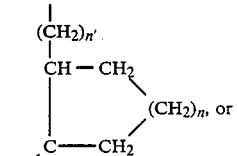  X wherein $R_b$ is

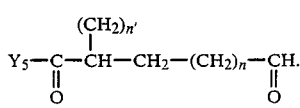

 or

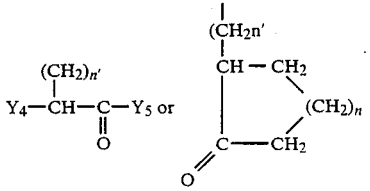

A compound of formula X can be treated with the appropriate amine having the formula $HNY_6Y_7$  XI in the presence of a reducing agent (e.g., hydrogen using a catalyst such as palladium on carbon, or a chemical reducing agent such as sodium cyanoborohydride) to obtain the corresponding product of formula I.

It is also possible to obtain an intermediate of formula X wherein $R_b$ is

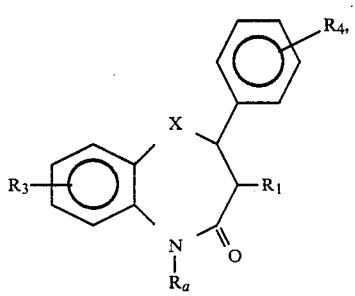

by reacting a compound of formula II with a compound of the formula

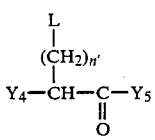  XIIa

-continued

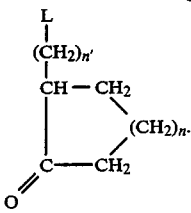

Compounds of formula I wherein $R_2$ is

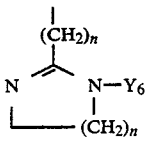

can be synthesized by reaction of a compound of formula II with an alkylating agent, such as chloroacetonitrile to give a compound of formula I wherein $R_2$ is —CH$_2$CN. The resultant compound of formula I wherein $R_2$ is —CH$_2$CN can be reacted with an alcohol, such as ethanol in the presence of a catalyst, such as hydrochloric acid or sodium ethoxide to give a compound of formula I wherein $R_2$ is

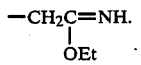

Treatment of this compound with a diamine of the formula H$_2$N—CH$_2$(CH$_2$)$_n$NHY$_6$ gives compounds of formula I wherein $R_2$ is

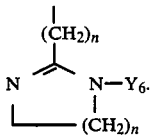

Preferred compounds of this invention are those wherein $R_3$ is located in the 6- or 7-position of the benzazepine nucleus or the 8- or 9- position of the benzothiazepine nucleus nd is halogen, trifluoromethyl or methoxy; and $R_4$ is located in the 4-position of the phenyl ring to which it is attached and is alkoxy. Most preferred are compounds wherein $R_3$ is 6-trifluoromethyl or 7-methoxy on the benzazepine nucleus, or 8-methoxy on the benzothiazepine nucleus, and $R_4$ is methoxy.

The following examples are specific embodiments of this invention.

EXAMPLE 1

[1(trans),3α, 4α]-1-[2-(Dimethylamino)cyclohexyl]-1,3,4,5-tetrahydro-4-(4-methoxyphenyl)-3-methyl-6-(trifluoromethyl)-2H-1-benzazepin-2-one, monohydrochloride To a suspension of 0.3 g of sodium hydride (6.3 mmol of a 50% oil dispersion) in 20 ml of dry dimethylformamide was added 2.0 g of (cis)-1,3,4,5-tetrahydro-4-(4-methoxyphenyl)-3-methyl-6- trifluoromethyl)-2H-1-benzazepin-2-one (5.73 mmol) in one portion as a solid. The solution was stirred for 45 minutes and then a solution of 1.59 g (6.3 mmol) of (trans)-1-iodo-2-(dimethylamino)cyclohexane in 12 ml of dry dimethylformamide was added dropwise over 15 minutes. The solution was stirred at room temperature for 20 minutes and then heated to 75° C. for 70 minutes. An additional 0.15 g of sodium hydride and 0.8 g of (trans)-1-iodo-2(dimethylamino)cyclohexane were added and heating was continued for an additional 30 minutes. The solution was allowed to cool and the dimethylformamide was removed under vacuum. Water was added to the residue, the aqueous solution was extracted twice with ethyl acetate and the combined organic phases were washed with brine and dried (magnesium sulfate) to afford 3.15 g of a semi-solid. Chromatography on silica with 1% triethylamine: 2% methanol:dichloromethane afforded 0.74 g of the free base of the title compound as a white foamy solid. The free base was dissolved in ether and hydrogen chloride-saturated ether was added to afford a white precipitate. The solution was evaporated and washed twice with ether to remove excess hydrogen chloride. The remaining white solid was recrystallized from isopropanol-isopropyl ether to afford 0.68 g of the title compound, melting point >250° C.

Analysis calc'd. for $C_{27}H_{34}ClF_3N_2O_2$ 1.5H$_2$O: C:62.51; H:6.77; N:5.40; Cl:6.83; F:10.99. Found: C:62.59; H:6.84; N:5.30; Cl:6.70; F:10.99.

EXAMPLE 2

(cis)-1-[2-(Dimethylamino)propyl]-1,3,4,5-tetrahydro-4-(4-methoxyphenyl)-3-methyl-6-(trifluoromethyl)-2H-1-benzazepin-2-one, isomer A, monohydrochloride A stirred solution of 3.0 g (8.69 mol) of (cis)-1,3,4,5-tetrahydro-4-(4-methoxyphenyl)-3-methyl-6-(trifluoromethyl)-2H-1-benzazepin-2-one in 90 ml of 2-butanone was treated with 1.7 g (10.75 mmol) of N,N-dimethyl-2-chloro-1-(methyl) ethylamine followed by 3.0 g (2.17 mmol) of pulverized potassium carbonate and heated to reflux. After approximately 2 days of heating, a significant amount of (cis)-1,3,4,5-tetrahydro-4-(4-methoxyphenyl)-3-methyl-6-(trifluoromethyl)-1-benzazepin-2-one was still present. An additional, 1.2 g of N,N-dimethyl-2-chloro-1-(methyl)ethyl-amine and 2.2 g of potassium carbonate were added and heating was continued for an additional day. After cooling, solids were filtered off, washed with 2-butanone, and the combined filtrates evaporated. The residue was shaken with 90 ml of ethyl acetate and 30 ml of water, the layers separated, and the ethyl acetate layer washed with 30 ml each of water and brine, dried (magnesium sulfate), evaporated. The residue was taken up in ether, the evaporation repeated, and the residue pump-dried to give 3.86 g of solid. Following two crystallizations from isopropyl ether, there was obtained 1.05 g of solid; melting point 154°–157° C. (s. 152C). TLC: Major product, $R_f$ 0.51, minor product, $R_f$ 0.42 (90:10 dichloromethanemethanol); Major product, $R_f$ 0.27; minor product, $R_f$ 0.17 (30:70 acetone-hexane).

The above material was chromatographed on 40 g of Baker silica gel, eluting with 30:70 acetone-hexane, to give 0.6 g of the single isomer as a colorless solid; melting point 159°–161° C.

Analysis calc'd. for $C_{24}H_{29}F_3N_2O_2$: C,66.34; H,6.73; N,6.45. Found: C,66.50; H,7.02; N,6.32.

The residue from the second isopropyl ether crystallization and fractions from the above chromatography rich in isomer A were combined and chromatographed to give an additional 0.36 g of identical material.

The 2 batches were combined (total, 0.92 g), suspended in 25 ml of methanol, treated with 0.45 ml of 5N ethanolic hydrogen chloride (solution obtained), and the solvent evaporated. The syrupy residue was rubbed under ether, evaporated, and pump-dried. This process was repeated to yield 0.92 g of the title colorless, non-hygroscopic, hydrochloride salt; melting point 101°–104° C. (foaming); sintering at 88° C. TLC: $R_f$ 0.40 (40:60 acetonehexane) $R_f$ 0.25 (8:1:1 dichloromethane-methanolacetic acid)

Analysis calc'd. for $C_{24}H_{29}F_3N_2O_2 \cdot HCl \cdot 0.5\ H_2O$: C,60.05; H,6.51; N,5.84; Cl, 7.39. Found: C,59.93; H,6.87; N,6.04; Cl, 7.14.

EXAMPLE 3

(cis)-1-[2-(Dimethylamino)propyl]-1,3,4,5-tetrahydro-4-(4-methoxyphenyl)-3-methyl-6-(trifluoromethyl)-2H-1-benzazepin-2-one, isomer B, monohydrochloride The isopropyl ether mother liquors from the crystallization of the free base of Isomer A of Example 2 were evaporated and the residual oil pump dried to give 2.4 g of a waxy residue. TLC (40:60 acetone-hexane) showed this material to be about a 40:60 mixture of isomer and isomer B.

The mixture was chromatographed on Baker silica gel, eluting with 40:60 acetone-hexane, to give 0.49 g of Isomer B base as a waxy solid. TLC: $R_f$ 0.19 (40:60 acetone-hexane). A solution of the base (0.48 g) in methanol was treated with 0.24 ml of 5N ethanolic hydrogen chloride and the solvent evaporated. The residue was rubbed under ether, evaporated, and pump-dried. This process was repeated to yield 0.50 g of colorless, slightly hygroscopic, hydrochloride salt; melting point 83°–86° C. (foaming); sintering at 76° C. TLC: $R_f$ 0.22 (40:60 acetone-hexane).

Analysis calc'd. for $C_{24}H_{29}F_3N_2O_2 \cdot HCl \cdot 0.5\ H_2O$: C,60.05; H,6.51; N,5.84; Cl, 7.39. Found: C,60.30; H,7.00; N,5.62; Cl,7.17.

EXAMPLE 4

(cis)-1-(2-Amino-1-methylethyl)-1,3,4,5-tetrahydro-4-(4-methoxyphenyl)-3-methyl-6-(trifluoromethyl)-2H-1-benzazepin-2-one, isomer B, monohydrochloride

(A)

(cis)-1,3,4,5-Tetrahydro-4-(4-methoxyphenyl)-α,3-dimethyl-2-oxo-6-(trifluoromethyl)-1H-1-benzazepine-1-acetonitrile, faster moving isomer To a suspension of 0.22 g of sodium hydride (5.37 mmol of a 60% oil dispersion) in 15 ml of dry dimethylformamide was added 1.50 g (4.29 mmol) of (cis)-3-methyl-4-(4-methoxyphenyl)-6-(tri-fluoromethyl)-2H-1-benzazepin-2-one. The solution was stirred for 15 minutes at room temperature, cooled at 0° C. and 0.42 ml (5.37 mmol) of 2-chloro-propionitrile was added neat. The solution was stirred at 0° C. for 10 minutes, warmed to room temperature for 15 minutes and heated to 45° C. for 90 minutes. An additional 50 mg of sodium hydride and 0.15 ml of chloropropionitrile were added and the solution was stirred at 45° C. for 20 minutes. The reaction was quenched with 1M ammonium chloride and dimethylformamide was removed under high vacuum with gentle warming. The residue was partitioned between ether and 1M ammonium chloride and the organic layer was washed with brine, dried (magnesium sulfate) and evaporated to afford a brown foamy solid which was combined with the crude product from a similar reaction performed on a 1.68 mmol scale. The crude product consisted of the two diastereomers of the product, designated the faster-moving isomer (FMI, $R_f$=0.74, 50% ethyl acetate/hexane) and the slower-moving isomer (SMI, $R_f$=0.66, 50% ethyl acetate/hexane). The solid was chromatographed on silica (60% ether/hexane) to afford 0.90 g of clean FMI as a white solid. The chromatography also afforded 0.34 g of nearly clean SMI, which was dissolved in hot exane containing 5% isopropyl ether and cooled to afford 0.29 g of clean SMI as hexagonal prisms, melting point 166°–168° C. Chromatography of the mixed fractions afforded an additional 0.44 g of clean FMI (total 1.34 g) and 0.31 g of SMI (total 0.60 g).

(B)

(cis)-1-(2-Amino-1-methylethyl)-1,3,4,5-tetrahydro-4-(4-methoxyphenyl)-3-methyl-6-(trifluoromethyl)-2H-1-benzazepin-2-one, isomer B, monohydrochloride A solution of 0.87 g of (cis)-1,3,4,5-tetrahydro-4-(4-methoxyphenyl)-α,3-dimethyl-2-oxo-6-(trifluoromethyl)-1H-1-benzazepine-1-acetonitrile, faster moving isomer (2.16 mmol) and 0.87 g of 5% rhodium on alumina in 125 ml of 1:1 methanol:ammonia saturated methanol was hydrogenated under 50 psi of hydrogen for 25 hours. The solution was filtered through celite, the celite was rinsed twice with methanol and the combined filtrates were evaporated. The semi-solid residue was taken up in dichloromethane, filtered through Celite and evaporated to afford 0.89 g of white foamy solid. To a solution of 0.34 g of this material in ether was added hydrogen chloride saturated ether. The solution, which became cloudy white, was evaporated and the residue was taken up in methanol and evaporated. The residue was taken up in 1 ml of methanol, 20 ml of ether was added followed by 20 ml of hexane, and the solution was chilled. The white solid was filtered and dried to afford 0.30 g of the title compound as a white solid, melting point 157°–162° C. (foaming).

Analysis calc'd. for $C_{22}H_{26}ClF_3N_2O_2 \cdot 0.21 H_2O$ C,59.15; H,5.96; N,6.27; Cl,7.93; F,12.76; Found: C,59.15; H,6.10; N,6.04; Cl,7.84; F,12.78.

EXAMPLE 5

(cis)-1-[2-(Dimethylamino)-1-methylethyl]-1,3,4,-5-tetrahydro-4-(4-methoxyphenyl)-3-methyl-6-(trifluoromethyl)-2H-1-benzazepin-2-one, isomer B, monohydrochloride A solution of 0.62 g of (cis)-1-(2-amino-1-methylethyl)-1,3,4,5-tetrahydro-4-(4-methoxyphenyl)-3-methyl-6-(trifluoromethyl)-2H-1-benzazepin-2-one, isomer B, monohydrochloride (1.52 mmol; see Example 4) and 1.3 ml of 37% aqueous formaldehyde in 10 ml of acetonitrile was added in one portion with stirring to 0.31 g of solid sodium cyanoborohydride and 0.16 ml of acetic acid was then added. The solution was stirred at room temperature for 2 hours, an additional 0.16 ml of acetic acid was added and the solution was stirred 30 minutes. Ether and 5% potassium carbonate were added, the mixture was partitioned, the organic layer was washed with brine, dried (magnesium sulfate) and evaporated to afford 0.84 g of a thick oil. Chromatography on silica with 2% methanol:1% triethylamine:dichloromethane produced 0.30 g of clean free base of the title compound. This material was dissolved in ether, hydrogen chloride saturated ether was added, the white suspension was evaporated and the residue was twice dissolved in methanol and evaporated. Hot isopropyl ether was added to the glassy solid and hot methanol was added dropwise until the solid dissolved. The solution was filtered, hot isopropyl ether was added until cloudiness persisted and the solution was cooled and refrigerated. The waxy precipitate was filtered and dried under vacuum to afford 220 mg of the title compound as a white solid, melting point >220° C.

Analysis calc'd. for $C_{24}H_{30}ClF_3N_2O_2 \cdot 0.60H_2O$: C,59.84; H,6.53; N,5,81; Cl,7.36; F,11.83; Found: C,59.84; H,6.52; N,5.76; Cl, 7.27; F,11.93.

EXAMPLE 6

(cis)-1-[2-(Dimethylamino)-1-methylethyl]-1,3,4,5-tetrahydro-4-(4-methoxyphenyl)-3-methyl-6-(trifluoromethyl)-2H-1-benzazepin-2-one, isomer A, monohydrochloride (A)

(cis)-1-(2-Amino-1-methylethyl)-1,3,4,5-tetrahydro-4-(4-methoxyphenyl)-3-methyl-6-(trifluoromethyl)-2H-1-benzazepine-2-one A solution of 0.60 g of (cis)-1,3,4,5-tetrahydro-4-(4-methoxyphenyl)-α,3-dimethyl-2-oxo-6-(trifluoromethyl)-1H-1-benzazepine-1-acetonitrile, slower moving isomer (1.49 mmol) and 0.49 g of 5% rhodium on alumina in 125 ml of 1:1 methanol:ammonia saturated methanol was hydrogenated under 50 psi of hydrogen for 20 hours. The solution was filtered through Celite, the Celite was rinsed twice with methanol and the combined filtrates were evaporated. The semi-solid residue was taken up in dichloromethane, filtered through Celite and evaporated to afford 0.56 g of the title compound as a white foamy solid.

(B)

(cis)-1-[2-(Dimethylamino)-1-methylethyl]-1,3,-4,5-tetrahydro-4-(4-methoxyphenyl)-3-methyl-6-(trifluoromethyl)-2H-1-benzazepin-2-one, isomer A, monohydrochloride A solution of 0.56 of crude (cis)-1-(2-amino-1-methylethyl)-1,3,4,5-tetrahydro-4(4-methoxyphenyl)-3-methyl-6-(trifluoromethyl)-2H-1-benzazepin-2-one (1.38 mmol) in 10 ml of acetonitrile containing 1.2 ml of 37% aqueous formaldehyde was added with stirring to 0.28 g of solid sodium cyanoborohydride (4.44 mmol) and 0.145 ml of acetic acid was then added. The solution was stirred for 2 hours, an additional 0.145 ml of acetic acid was added and the solution was stirred for 30 minutes. The reaction was partitioned between ether and 10% aqueous potassium carbonate and the organic layer was washed with brine, dried (magnesium sulfate) and evaporated to afford 0.70 g of oil. This material was flash chromatographed on silica (1% methanol/0.5% triethylamine/dichloromethane) to afford 0.32 g of clean free base of the title compound as a white foamy solid. This material was dissolved in ether and hydrogen chloride saturated ether was added to produce a white precipitate. The ether was evaporated, the solid was dissolved in methanol and the solution was evaporated. The solid was again dissolved in methanol and the solution was filtered through Celite and evaporated. The solid was dissolved in 2 ml of warm methanol, hot isopropyl ether was added until incipient cloudiness, the solution was cooled and the solid collected by filtration to afford 0.27 g of the title compound as a white crystalline solid, melting point >220° C.

Analysis calc'd for $C_{24}H_{30}ClF_3N_2O_2 \cdot HCl$: C,61.20; H,6.42; N,5.95; Cl,7.53; F,12.10; Found: C,61.15; H,6.52; N,5.88; Cl,7.71; F,11.78.

EXAMPLE 7

[3R-[1(R*),3α,4α)]-3-(Acetyloxy)-1,3,4,5-tetrahydro-4-(4-methoxyphenyl)-1-[(1-methyl-2-pyrrolidinyl)methyl]-6-(trifluoromethyl)-2H-1-benzazepin-2-one, monohydrochloride (A) R-N-(t-Butoxycarbonyl)-2-pyrrolidine methanol A solution of R-2-pyrrolidinemethanol (5.0 g, 50 mmol) in dry dichloromethane (125 ml) at 0° C. was treated dropwise with a solution of di-tbutyl dicarbonate (13 g, 59.5 mmol) in 50 ml of dichloromethane over a period of 15 minutes. Immediate evolution of carbon dioxide gas occurred. The cooling bath was removed and the mixture was stirred at room temperature for an additional 6 hours. The reaction mixture was then concentrated under reduced pressure to obtain the title compound as a light yellow viscous oil (13 g). The crude material was used in the next reaction without further purification.

(B) R-N-Methyl-2-pyrrolidinemethanol

Lithium aluminum hydride (7.6 g, 200 mmol) was added in small portions to dry tetrahydrofuran (200 ml) cooled to 0°–5° C. A solution of R-N-(t-butoxycarbonyl)-2-pyrrolidinemethanol (13 g crude, 50 mmol) in dry tetrahydrofuran (100 ml) was then added dropwise with vigorous stirring over a period of 45 minutes. After 30 minutes at 0° C. room temperature, the reaction mixture was heated to reflux for 16 hours. The reaction mixture was then cooled to 0° C. and the excess hydride was destroyed by a slow addition of saturated aqueous sodium sulfate. Addition was continued until all the inorganic salts were precipitated as a white granular solid. The mixture was diluted with ethyl acetate (500 ml), dried lmagnesium sulfate), filtered and concentrated to give the title compound as a colorless oil (5.7 g). The crude product was used without purification in the next reaction (C) R-2-(Chloromethyl)-1-methylpyrrolidine, hydrochloride To a solution of R-N-methyl-2-pyrrolidinemethanol (2.O g, 17.4 mmol) in chloroform (18 ml) at 0° C. was added dropwise thionyl chlrride (0.74 g, 52.1 mmol). The reaction mixture was heated to reflux for 2 hours, and then cooled to room temperature and concentrated at reduced pressure. The residue was recrystallized from acetone-ether to yield the title compound as a pale yellow solid (1.14 g).

(D)

3R-[1(R*),3α,4α]]-1-(1-Methyl-2-pyrrolidinyl)methyl]-3-(hydroxy)-1,3,4,5-tetrahydro-4-(4-methoxyphenyl)-6-(trifluoromethyl)-2H-1-benzazepin-2-one Sodium hydride (0.19 g, 8.1 mmol) was added to a solution of [3R-cis]-3-hydroxy-4-(4-methoxyphenyl)-6-(trifluoromethyl)-2H-1-benzazepin-2-one (1.05 g, 3.0 mmol) in dry dimethylformamide (30 ml). The mixture was stirred at room temperature for 1 hour whereupon R-2-(chloromethyl)-1-methylpyrrolidine, hydrochloride (0.78 g, 4.5 mmol) was added and the mixture was heated to 80° C. for 1 hour. The reaction mixture was then cooled and quenched with saturated aqueous potassium bicarbonate and extracted with ethyl acetate (three times). The combined extracts were washed with 10% aqueous lithium chloride, dried (magnesium sulfate) and concentrated. The crude yellow liquid was chromatographed on a silica gel column and eluted with 1–3% methanol in dichloromethane to give the title compound as a viscous liquid (0.24 g).

(E)

[3R-1(R*),3α,4α]]-3-(Acetyloxy)-1,3,4,5-tetra-hydro-4-(4-methoxyphenyl)-1-[(1-methyl-2-pyrrolidinyl)methyl]-6-(trifluoromethyl)-2H-1-benzazepin-2-one, monohydrochloride A solution of [3R-[1(R*),3α,4α]]-1-[(1-methyl-2-pyrrolidinyl)methyl]-3-(hydroxy)-1,3,4,5-tetrahydro-4-(4-methoxyphenyl)-6-(trifluoromethyl)-2H-1-benzazepin-2-one (0.24 g, 0.54 mmol), acetic anhydride (0.27 g, 2.68 mmol) and 4-dimethylaminopyridine (0.07 g, 1.07 mmol) in dry dichloromethane (6 ml) was stirred at room temperature for 60 hours. The reaction mixture was then absorbed onto silica gel (60–200mesh), poured onto a silica gel column and eluted with 1–3% methanol in dichloromethane to give the free base of the title compound. The viscous oil was dissolved in ether and treated with a saturated etheral hydrogen chloride solution. The white precipitate was recrystallized from toluenehexane to yield the title compound as a white solid (0.23 g), melting point 158°–162° C. $[\alpha]_D = +126.8°$ (c=1.0, methanol).

Analysis calc'd. for $C_{26}H_{30}F_3ClN_2O_4 1.0H_2O$): C,57.31; H,5.92; N,5.14; F, 10.46; Cl,6.51; Found: C,57.63; H,5.68; N,5.23; F,10.21; Cl,6.34.

EXAMPLE 8

[3R-[1(S*),3α,4α]]-3-(Acetyloxy)-1-[2-(dimethylamino)-3-phenylpropyl]-1,3,4,5-tetrahydro-4-(4-methoxyphenyl)-6-(trifluoromethyl)-2H-1-benzazepin-2-one, monohydrochloride (A) S-2-(Dimethylamino)-3-phenyl-1-propanol To a solution of S-2-amino-3-phenyl-1-propanol (6.0g, 4.0 mmol) and 37% aqueous formaldehyde (20 ml) in acetonitrile (200 ml) was added with stirring sodium cyanoborohydride (4.0 g, 64 mmol) in small portions. The mixture was stirred for 30 minutes whereupon glacial acetic acid was added dropwise to the solution until it tested neutral to pH paper. The mixture was stirred at room temperature for 2 hours with occasional addition of glacial acetic acid to maintain a neutral pH. The reaction mixture was then concentrated and the residual oil was diluted with 2N potassium hydroxide (250 ml). It was extracted with ethyl acetate three times and the combined extracts washed with 1N potassium hydroxide and extracted with 1N aqueous hydrochloric acid three times. The acid extracts were combined, neutralized with solid potassium hydroxide and extracted with ethyl acetate three times. The extracts were combined, dried over anhydrous magnesium sulfate and concentrated to obtain the title compound as a viscous oil (6.48 g).

(B) S-1-Chloro-2-(dimethylamino)-3-phenylpropane, hydrochloride

To S-2-(Dimethylamino)-3-phenyl-1-propanol (3.0 g, 16.7 mmol) in chloroform (20 ml) at 0° C. was added dropwise thionyl chloride (5.97 g, 50.2 mmol). The reaction mixture was heated to reflux for 2 hours and then evaporated to dryness under reduced pressure. The residue was recrystallized from acetone-ether to give the title compund as an off white solid (2.38 g, melting point 167.5°–168.5° C.).

(C)

[3R-[1(S*),3α,4α]]-1-[2-(Dimethylamino)-3-phenylpropyl]-3-(hydroxy)-1,3,4,5-tetrahydro-4-(4-methoxyphenyl)-6-trifluoromethyl)-2H-1-benzazepin-2-one Sodium hydride (0.22 g, 9.0 mmol) was added to a solution of (3R-cis)-3-hydroxy-4-(4-methoxyphenyl)-6-(trifluoromethyl)-2H-1-benzazepin-2-one (1.05 g, 3.0 mmol) in dry dimethylformamide (30 ml). The mixture was stirred at room temperature for 1 hour whereupon (S)-1-Chloro-2-(dimethylamino)-3-phenylpropane, hydrochloride (0.89 g, 4.5 mmol) was added and the mixture was heated to 85° C. for 2 hours. The reaction mixture was cooled, quenched with water and extracted with ethyl acetate three times. The combined extracts were washed with 10% aqueous lithium chloride three times; brine, and dried over anhydrous magnesium sulfate. After concentration, the crude product was chromatographed on a silica gel column and eluted with 10–30% ethyl acetatehexane to yield the title compound as a white foam (1.16 g).

(D)

[3R-[1(S*),3α,4α]]-3-(Acetyloxy)-1-[2-(dimethylamino)-3-phenylpropyl]-1,3,4,5-tetrahydro-4-(4-methoxyphenyl)-6-(trifluoromethyl)-2H-1-benzazepin-2-one, monohydrochloride A solution of [3R-[1(S*),3α,4α]]-1-[2-dimethylamino)-3-phenylpropyl]-3-(hydroxy)-1,3,4, 5-tetrahydro-4-(4-methoxyphenyl)-6-(trifluoromethyl)-2H-1-benzazepin-2-one (1.16 g, 2.26 mmol), acetic anhydride (1.16 g, 11.32 mmol) and 4-dimethylaminopyridine (0.55 g, 4.53 mmol) in dry dichloromethane (25 ml) was stirred at room temperature for 16 hours. The reaction mixture was absorbed onto silica gel (60–200 mesh), poured onto a silica gel column and eluted with 5–25% ethyl acetatehexane to obtain the free base of the title compound as a white foam. The free base was dissolved in ether and excess hydrogen chloride ether solution was added to give the title compound as a white solid (0.96 g), melting point 144°–147° C. $[\alpha]_D = +52.40°$ (c=1.0, methanol).

Analysis calc'd. for $C_{31}H_{34}ClF_3N_2O_4·0.76H_2O$: C,61.56; H,5.92; N,4.63; Cl,1,5.86; F,9.42; Found: C,61.60; H,6.00; N,4.59; Cl,5.93; F,9.23.

EXAMPLE 9

[3R-[1(R*),3α,4α]]-3-(Acetyloxy)-1-2-(dimethylamino)-3-phenylpropyl]-1,3,4,5-tetrahydro-4-(4-methoxyphenyl)-6-(trifluoromethyl)-2H-1-benzazepin-2-one, monohydrochloride (A) R-2-(Dimethylamino)-3-phenyl-1-propanol To a solution of R-2-amino-3-phenyl-1propanol (6 g, 40 mmol) and 37% aqueous formaldehyde (20 ml) in acetonitrile (200 ml) was added with stirring sodium cyanoborohydride (4.0 g, 64 mmol) in small portions. The mixture was stirred for 30 minutes whereupon glacial acetic acid was added dropwise to the solution until it tested neutral to pH paper. The mixture was stirred at room temperature for 2 hours with occasional addition of glacial acetic acid to maintain a neutral pH. The reaction mixture was then concentrated and the residual oil was diluted with 2N potassium hydroxide (250 ml) solution. It was extracted with ethyl acetate three times and the combined extracts washed with 1N potassium hydroxide solution and extracted with 1N hydrochloric acid solution three times. The acid extracts were combined, neutralized with solid potassium hydroxide and extracted with ethyl acetate three times. The extracts were combined, dried over anhydrous magnesium sulfate and concentrated to obtain the title compound as a viscous oil (6.23 g).

(B) R-1-Chloro-2-(dimethylamino)-3-phenylpropane, hydrochloride

To R-2-(dimethylamino)-3-phenyl-1-propanol (3.0 g, 16.7 mmol) in chloroform (20 ml) at 0° C. was added dropwise thionyl chloride (6.0 g, 50.2 mmol). The reaction mixture was heated to reflux for 2 hours whereupon it was evaporated to dryness under reduced pressure. The residue was recrystallized from acetone-ether to give the title compound as an off white solid (2.27 g, m.p. 170°–171.5° C.,).

(C) [3R-[1(R*),3α,4α]]-1-[2-(Dimethylamino)-3-phenylpropyl-3-(hydroxy)-1,3,4,5-tetrahydro-4-(4-methoxyphenyl)-6-(trifluoromethyl)-2H-1-benzazepin-2-one Sodium hydride (0.13 g, 5.4 mmol) was added to a solution of (3R-cis)-3-hydroxy-4-(4-methoxyphenyl)-6-(trifluoromethyl)-2H-1-benzazepin-2-one (0.70 g, 2.0 mmol) in dry dimethylformamide (20 ml). The mixture was stirred at room temperature for 1 hour whereupon R-1-chloro-2-(dimethylamino)-3phenylpropane, hydrochloride (0.60 g, 3.0 mmol) was added and the mixture was heated to 80° C. for 2.5 hours. The reaction mixture was cooled, quenched with water and extrated with ethyl acetate three times. The combined extracts were washed with 10% aqueous lithium chloride three times; brine; filtered, dried over anhydrous magnesium sulfate and concentrated. The crude product was chromatographed on a silica gel column and eluted with 20–50% ethyl acetate-hexane to yield the title compound as a white foam (0.60 g).

(D) [3R-1(R*),3α,4α]-3-(Acetyloxy)-1-2-(dimethylamino)-3-phenylpropyl]-1,3,4,5-tetrahydro-4-(4-methoxyphenyl)-6-(trifluoromethyl)-2H-1-benzazepin-2-one, monohydrochloride A solution of [3R-[1(R*),3α,4α]]-1-[2-(dimethylamino)-3-phenylpropyl]-3-(hydroxy)-1,3, 4,5-tetrahydro-4-(4-methoxyphenyl)-6-(trifluoromethyl)-2H-1-benzazepin-2-one (1.0 g, 1.95 mmol), acetic anhydride (1.0 g, 9.8 mmol) and 4-dimethylaminopyridine (0.48 g, 3.90 mmol) in dry dichloromethane (20 ml) was stirred at room temperature for 14 hours. The reaction mixture was absorbed onto silica gel (60–200mesh), poured onto a silica gel column and eluted with 5–25% ethyl acetate-hexane to obtain the free base as a white foam. The free base was dissolved in ether and excess hydrogen chloride-ether solution was added to give the title compound as a white solid (0.61 g), m.p. 146°–150° C. $[\alpha]_D = +137.3°$ (c=1.0, methanol).

Analysis calc'd for $C_{31}H_{34}ClF_3N_2O_4 \cdot 0.56 \cdot H_2O$: C,61.93; H,5.89; N,4.66; Cl,5.90; F,9.48; Found: C,62.02; H,6.21; N,4.67; Cl,5.83; F,9.33.

EXAMPLE 10

(3R-cis)-1-[2-(Dimethylamino)-2-methylpropyl]-1,3,4,5-tetrahydro-3-hydroxy-4-(4-methoxyphenyl)-6-(trifluoromethyl)-2H-1-benzazepin-2-one, monohydrochloride The following preparation is run under argon.

A stirred solution of (3R-cis)-3-hydroxy-4-(4-methoxyphenyl)-6-(trifluoromethyl)-2H-1-benzazepin-2-one (2.5g; 7.12 mmol) in 75 ml of dimethylformamide was treated with 0.3 g (7.5 mmol of 60% sodium hydride and stirred for 1 hour. To this solution was added a dried toluene solution of 1-chloro-2-(dimethylamino)-2-methylpropane (released from 3.75 g (21.8 mmol) of the hydrochloride salt with potassium carbonate into toluene) and the mixture was heated in an oil bath at 71–78° C. (both temp.) for 1.25 hours. After cooling, the bulk of dimethylformamide was removed on a rotary evaporator at 0.2 mm and the residue was shaken with 125 ml of ethyl acetate and 50 ml of water. The layers were separated and the organic phase was washed with water (twice, 50 ml), brine (25 ml), dried (magnesium sulfate), and evaporated. The solid residue was suspended in ether, the evaporation repeated, and the solid pump dried; weight 3.33 g. This was combined with 0.64 g of product from an earlier run by dissolving in ether, filtering to clarify, and evaporating. The solid residue (3.94 g) was shaken with 60 ml of ethyl acetate and 40 ml of water containing 17 ml of 1N hydrochloric acid. The layers were separated and the organic phase extracted with 40 ml of water. The combined aqueous phases were washed with ether (wash discarded), layered over with 40 ml of ethyl acetate, 19 ml of N sodium hydroxide was added, the mixture shaken and separated. The aqueous phase was extracted with ethyl acetate (two times 30 ml), the combined ethyl acetate layers were washed with brine (20 ml), dried (magnesium sulfate), and evaporated finally at 0.2 mm to give 3.66 g of solid. Following crystallization from 25 ml of hot isopropanol the colorless material (free base of the title compound) weighed 2.36 g, melting point 157°–159° C. (sintering at 155° C.).

Analysis calc'd for $C_{24}H_{29}F_3N_2O_3$: C,63.98; H,6.49; N,6.22; F,12.65; Found: C,64.17; H,6.53; N,6.08; F,12.93.

The base (2.34 g) in 50 ml of ethyl acetate was treated with 1.2 ml of 5N ethanolic hydrogen chloride and the solvent evaporated finally at 0.2 mm. The almost solid residue was rubbed under ethyl ether and the evaporation repeated to give after pump drying, 2.67 g of the title compound as a colorless solid; m.p. 90°–93° C. (foaming), sintering 82° C. $[\alpha]_D = +114°$ (C=1.0, methanol).

Analysis calc'd for $C_{24}H_{29}F_3N_2O_3 \cdot HCl \cdot 0.5H_2O$: C,58.12; H,6.30; N,5.64; Cl,7.15; Found: C,58.06; H,6.53; N,5.37; Cl,7.00.

EXAMPLE 11

(3R-cis)-1-2-(Dimethylamino)-1-phenylethyl-1,-3,4,5-tetrahydro-3-hydroxy-4-(4-methoxyphenyl)-6-(trifluoromethyl)-2H-1-benzazepin-2-one, isomer A, monohydrochloride A toluene solution of N,N-dimethyl-2-chloro-2-phenylethylamine was prepared by partitioning 3.59 g of the hydrochloride salt (16.3 mmol) between 15 ml of toluene and 100 ml of aqueous sodium bicarbonate. The aqueous phase was washed with an additional 10 ml of toluene and the combined organic phases were dried (magnesium sulfate) and filtered. To a stirred suspension of 0.75 g of sodium hydride (15.6 mmol of a 50% oil dispersion) in 30 ml of dry dimethylformamide was added 5.0 g of (3R-cis)-3-hydroxy-4-(4-methoxyphenyl)-6-(trifluoromethyl)-2H-1-benzazepin-2-one (14.2 mmol) in one portion as a solid. The solution was stirred for 1 hour at room temperature, heated to 70° C. and the toluene solution of N,N-dimethyl-2-chloro-2-phenylethylamine was added dropwise over 2 hours. A solution of 7 g of the above hydrochloride salt (4.5 mmol) and 0.51 g of potassium t-butoxide (4.5 mmol) was stirred in 5 ml of dimethylformamide for 2 minutes and added to the alkylation reaction. The resulting solution was stirred at 70° C. for an additional 2.25 hours and quenched with aqueous sodium bicarbonate. Solvents were removed under high vacuum with gentle warming. The residue was partitioned between ethyl acetate and aqueous sodium bicarbonate, the organic phase was washed with brine, dried (magnesium sulfate), filtered and evaporated to afford a light yellow foamy gum. The crude product was dissolved in 25 ml of ether, seeded with (3R-cis)-3-hydroxy-4-(4-methoxyphenyl)-6-(trifluoromethyl)-2H-1-benzazepin-2-one and chilled to afford (after filtration) 0.25 g of recovered (3R-cis)-3-hyroxy-4-(4-methoxyphenyl)-6-(trifluoromethyl)-2H-1-benzazepin-2-one. Evaporation of the mother liquor provided 7.23 g of foamy solid which was chromatographed on silica (2% methanol/0.5% triethylamine/dichloromethane) to yield 1.90 g of clean FMI (faster-moving isomer) as a light yellow foamy solid. A solution of 0.41 g of clean FMI was dissolved in ether and treated with hydrogen chloride-saturated ether. The white solid was filtered, rinsed twice with ether and air-dried to produce 0.41 g of white solid. This material was dissolved in 2 ml of isopropanol/6ml isopropyl ether with warming and the solution was filtered of a small amount of insoluble material. The filtrate was treated with hexane and the resulting white solid was collected by filtration and dried to afford 0.39 g of the title compound, melting point 136°–142° C. $[\alpha]_D = -146.2°$ (c=1, methanol).

Analysis calc'd. for $C_{28}H_{30}ClF_3N_2O_3 \cdot 0.52$ moles $H_2O$: C,61.77; H,5.75; N,5.14; Cl1,6.51; F,10.47; Found: C,61.77; H,6.02; N,5.26; Cl,6.46; F,10.63.

EXAMPLE 12

(3R-cis)-1-[2-(Dimethylamino)-1-phenylethyl]-1,3,4,5-tetrahydro-3-hydroxy-4-(4-methoxyphenyl)-6-(trifluoromethyl)-2H-1-benzazepin-2-one, isomer B, monohydrochloride No pure SMI (slower-moving isomer)-containing fractions were obtained from the chromatography of (3R-cis)-1-[2-(dimethylamino)-1-phenylethyl]-1,3,4,5-tetrahydro-3-hydroxy-4-(4-methoxyphenyl)-6-(trifluoromethyl)-2H-1-benzazepin-2-one, isomer A, monohydrochloride. Fractions containing SMI (contaminated with FMI and (3R-cis)-3-hydroxy-4-(4-methoxyphenyl)-6-(trifluoromethyl)-2H-1-benzazepin-2-one) were pooled and evaporated to afford 3.40 g of crude SMI. This material was rechromatographed on silica (2% methanol/0.5% triethylamine/dichloromethane) to yield 0.81 g of SMI, containing trace amounts of FMI and a significant amount of (3R-cis)-3-hydroxy-4-(4-methoxyphenyl)-6-(trifluoromethyl)-2H-1-benzazepin-2-one. This material was chromatographed on six preparative thin layer chromatography plates (5% methanol/dichloromethane), the major band was excised, extracted twice with 5% methanol/1% triethylamine/dichloromethane and the combined extracts evaporated and chased three times with carbon tetrachloride to afford 0.41 g of clean free base of the title compound. This material was dissolved in ether, filtered through Celite to remove cloudiness and hydrogen chloride saturated ether was added. The resulting white solid was filtered, rinsed twice with ether and air-dried to afford 0.42 g of the title compound as a white solid, melting point 165°–171° C. $[\alpha]_D = +221.8°$ (C=1, methanol).

Analysis calc'd for $C_{28}H_{30}N_2O_3ClF_3 \cdot 0.49H_2O$: C,61.84; H,5.74; N,5.15; Cl,6.51; F,10.48; Found: C,61.84; H,5.81; N,5.07; Cl,6.12; F,10.18.

EXAMPLE 13

[3R-[1(S*),3α,4α]]-3-(Acetyloxy)-1,3,4,5-tetrahydro-4-(4-methoxyphenyl)-1-(2-pyrrolidinylmethyl)-6-(trifluoromethyl)-2H-1-benzazepin-2one, monohydrochloride (A) S-N-(Benzyloxycarbonyl)-2-pyrrolidinemethanol Powdered anhydrous potassium carbonate (41 g, 297 mmol) was added with stirring to a solution of S-2-pyrrolidinemethanol (6 g, 59.32 mmol) in acetone (120 ml). The mixture was cooled to 0° C. and benzyl chloroformate (16.94 ml, 118.6 mmol) was added dropwise. After 40 minutes, the reaction mixture was diluted with ethyl acetate and water. The organic layer was separated and the aqueous layer was extracted with ethyl acetate. The organic extracts were combined, dried (magnesium sulfate) and concentrated. The crude oil was chromatographed on a silica gel column and eluted with 25% ethyl acetate in hexane to obtain the title compound 2 (12.22 g) as a pale yellow oil.

(B) S-1-(Benzyloxycarbonyl)-2-(bromomethyl)-pyrrolidine

Triphenyl phosphine (4.46 g, 17 mmol) and carbon tetrabromide (5.64 g, 17 mmol) were added to a solution of S-N-(Benzyloxycarbonyl)-2-pyrrolidinemethanol (2 g, 8.5 mmol) in ether (100ml). The mixture was stirred at room temperature for 19 hours, cooled and the precipitated solids were filtered off. The residual solids were washed with hexane. The filtrate was concentrated and purified by chromatography on a silica gel column. Elution with 10–20% ethyl acetate in hexane afforded the title compound (2.11 g), as a colorless oil.

(C) [3R-[1(S*),3α,4α)]-1-(Benzyloxycarbonyl-2 pyrrolidinyl)methyl]-3-hydroxy-1,3,4,5-tetrahydro-4-(4-methoxyphenyl)-6-(trifluoromethyl)-2H-1-benzazepin-2-one (3R-cis)-3-Hydroxy-4-(4-methoxyphenyl)-6-(trifluoromethyl)-2H-1-benzazepin-2-one (0.8 g, 2.3 mmol) was added to a suspension of sodium hydride (0.066 g, 2.7 mmol) in dimethylformamide (23 ml). After 1 hour at room temperature, S-1-(benzyloxycarbonyl)-2-(bromomethyl)pyrrolidine (0.97 g, 3.4 mmol) was added. The reaction mixture was heated at 65° C. for 2.5 hours and then additional amounts of sodium hydride (0.028 g, 1.14 mmol) and S-1-(benzyloxycarbonyl)-2-(bromomethyl)pyrrole (0.33 g, 1.14 mmol) were added. After an additional 1 hour at 65° C. the mixture was cooled and then diluted with water and extracted with ethyl acetate three times. The ethyl acetate extracts were combined, washed with 10% aqueous lithium chloride, dried (magnesium sulfate) and concentrated. The crude residue was chromatographed on a silica gel column and eluted with 20-40% ethyl acetate in hexane to obtain the title compound (0.8 g).

(D)

[3R-[1(S*),3α,4α]]-3-Acetoxy-1-(1-benzyloxycarbonyl-2-pyrrolidinyl)methyl]-1,3,4,5-tetrahydro-4-(4-methoxyphenyl)-6-(trifluoromethyl)-2H-1-benzazepin-2-one N,N-Dimethylaminopyridine (0.45 g/3.7 mmol) was added to a solution of [3R-[1(S*),3α,4α]]-1-(benzyloxycarbonyl-2-pyrrolidinyl)methyl]-3-hydroxy-1,3,4,5-tetrahydro-4-(4-methoxyphenyl)-6-(trifluoromethyl)-2H-1-benzazepin-2-one (1.14 g, 1.85 mmol) and acetic anhydride (0.87 ml, 9.24 mmol) in dichloromethane (20 ml). The mixture was stirred at room temperature for 4 days, absorbed into silica gel (60 mesh) and flash chromatography on a silica gel column. Elution with 10-40% ethyl acetate in hexane afforded the title compound (0.68 g) as a viscous oil.

(E)

[3R-[1(S*),3α,4α]]-3-(Acetyloxy)-1,3,4,5-tetrahydro-4-(4-methoxyphenyl)-1-(2-pyrrolidinyl-methyl)-6-(trifluoromethyl)-2H-1-benzazepin-2-one, monohydrochloride Ammonium formate (0.23 g, 3.64 mmol) was added in one portion to a suspension of 10% palladium on charcoal (0.05 g) and [3R-1(S*),3α,4α]]-3-acetoxy-1-(1-benzyloxycarbonyl-2-pyrrolidinyl)methyl]-1,3,4,5-tetrahydro-4-(4-methoxyphenyl)-6-(trifluoromethyl)-2H-1-benzazepin-2-one (0.48 g, 0.73 mmol) in methanol (10 ml). The mixture was heated under reflux for 30 minutes, whereupon it was cooled and filtered through Celite. The residual solids were washed with ethyl acetate. The filtrate was concentrated to obtain a white foam, which was dissolved in ether and treated with excess etheral hydrogen chloride solution. The solution was concentrated and crystallized from toluene/hexane to obtain the title compound (0.325 g) as an off-white solid, melting point 217°-219° C. [α]$_D$= +78.7° (c=1.0, methanol).

Analysis calc'd for $C_{25}H_{27}F_3N_2O_4HCl \cdot 0.29H_2O$: C,58.06; H,5.37; N,5.42, Cl,6.86; F,11.02; Found: C,58.37; H,5.57; N,5.54; Cl,7.05; F,10.58.

EXAMPLE 14

[3R-[1(S*),3α,4α]]-3-(Acetyloxy)-1,3,4,5-tetrahydro-4-(4-methoxyphenyl)-1-(1-methyl-2-pyrrolidinyl)methyl]-6-(trifluoromethyl)-2H-1-benzazepin-2-one, monohydrochloride (A) S-N-(t-Butyloxycarbonyl)-2-pyrrolidinemethanol A solution of S-2-pyrrolidinemethanol (10 g, 100 ) in dry dichloromethane (250 ml) was treated dropwise at 0°-5° C. with a solution of di-t-butyl dicarbonate (26 g, 119 mmol) in 100 ml of dichloromethane over a period of 30 minutes. After 6 hours at room temperature, the reaction mixture was concentrated to obtain the title compound (23.5 g) as a viscous oil.

(B) S-N-Methyl-2-pyrrolidinemethanol

A solution of S-N-(t-butyloxycarbon 1)-2-pyrrolidinemethanol (17.5 g crude, 87 mmol) in dry tetrahydrofuran (100 ml) was added dropwise at 0°-5° C. to a suspension of lithium aluminum hydride (11.4 g, 300 mmol). The mixture was heated under reflux for 16 hours. It was then cooled in an ice-water bath and excess hydride was destroyed by dropwise addition of saturated sodium sulfate solution. The mixture was diluted with ethyl acetate and filtered through anhydrous magnesium sulfate. The residual solid was washed thoroughly with ethyl acetate. The combined filtrate was concentrated under reduced pressure to obtain a yellow oil, which was distilled to obtain the title compound, boiling point 97° C./50 mm. Hg.

(C) S-2-(Chloromethyl)-1-methylpyrrolidine

Thionyl chloride (3.28 ml, 45 mmol) was added dropwise to a solution of S-N-methyl-2-pyrrolidinemethanol (1.73 g, 15 mmol) in chloroform (15 ml) at 0°-5° C. The mixture was heated under reflux for 2 hours and was then concentrated. The crude residue was crystallized from acetone/ether to obtain the title compound (1.48 g) as a hydrochloride salt.

(D)

[3R-[1(S*),3α,4α]]-1-[(1-Methyl-2-pyrrolidinyl)methyl]-3-hydroxy-1,3,4,5-tetrahydro-4-(4-methoxyphenyl)-6-(trifluoromethyl)-2H-1-benzazepin-2-one (3R-cis)-3-Hydroxy-4-(4-methoxyphenyl)-6-(trifluoromethyl)-2H-1-benzazepin-2-one (0.7 g, 2 mmol) was added to a suspension of sodium hydride (0.13 g, 5.4 mmol) in dimethylformamide (20 ml). The mixture was stirred at room temperature for 1 hour, cooled at 0° C. and the hydrochloride salt of S-2-(chloromethyl)-1-methylpyrrolidine (0.52g, 3 mmol) was added. After stirring for 1 hour at room temperature, additional sodium hydride (0.012 g, 0.5 mmol) was added. The mixture was stirred for an additional 3 hours and was then diluted with water. It was then extracted with ethyl acetate and the ethyl acetate extract was washed with 10% aqueous lithium chloride solution, dried over anhydrous magnesium sulfate and concentrated. The crude residue was chromatographed on a silica gel column and eluted with 2-5% methanol in dichloromethane to obtain the title compound (0.65 g) as a white foam.

(E)

[3R-[1(S*),3α,4α]]-3-(Acetyloxy)-1,3,4,5-tetrahydro-4-(4-methoxyphenyl)-1-(1-methyl-2-pyrrolidinyl)methyl]-6-(trifluoromethyl)-2H-1-benzazepin-2-one, monohydrochloride N,N-Dimethylaminopyridine (0.41 g, 3.34 mmol) [(1-methyl-2-pyrrolidinyl)methyl]-3-hydroxy-1,3,4, 5-tetrahydro-4-(4-methoxyphenyl)-6-(trifluoromethyl)-2H-1-benzazepin-2-one (0.75 g, 1.67 mmol) and acetic anhydride (0.79 ml, 8.4 mmol) in dichloromethane (18 ml). The mixture was stirred at room temperature for 24 hours. It was absorbed onto coarse silica gel and flash chromatographed on a silica gel column using 2-3% methanol in dichloromethane as eluents to obtain the title compound as its free base. The free base was dissolved in ether and was then treated with excess etheral hydrogen chloride solution. An additional 20 ml of ether was added and the precipitated salt was decanted off and dried in vacuo at 70° C. to obtain the title compound (0.536 g) as a white solid, melting point 151°-154° C. [α $_D$= +80.0° (c=1.0, methanol).

Analysis calc'd for $C_{26}H_{29}F_3N_2O_4HCl \cdot 0.63H_2O$: C,58.00; H,5.85; N,5.20; Cl,6.59; F,10.59; Found: C,57.74; H,5.56; N,4.93; Cl,7.01; F,10.16.

EXAMPLE 15

[3R-[1(R*),3α,4α]]-1,3,4,5-Tetrahydro-3-hydroxy-4-(4-methoxyphenyl)-1-(2-pyrrolidinylmethyl)-6-(trifluoromethyl)-2H-1-benzazepin-2-one, monohydrochloride (A) R-N-(Benzyloxycarbonyl)-2-pyrrolidinemethanol Benzyl chloroformate (6 ml, 39.5 mmol) was added dropwise at 0° C. to a suspension of powdered anhydrous potassium carbonate (13.7 g, 99 mmol) and (R)-2-pyrrolidinemethanol (2 g, 19.8 mmol) in acetone (100 ml). After 1 hour, the reaction mixture was diluted with water and ethyl acetate. The organic layer was separated and the aqueous layer was extracted with ethyl acetate twice. The combined organic extracts were dried (magnesium sulfate), filtered and concentrated. The crude oil was chromatographed on a silica gel column and eluted with 20–60% ethyl acetate in hexane to obtain the title compound (4.57 g).

B) R-1-(benzyloxycarbonyl)-2-(bromomethyl)pyrrolidine

A solution of R-N-(benzyloxycarbonyl)-2-pyrrolidinemethanol (4.55 g, 19.3 mmol), triphenyl phosphine (10.2 g, 38.7 mmol) and carbon tetrabromide (12.8 g, 38.7 mmol) in ether (200 ml) was stirred at room temperature overnight. The reaction mixture was diluted with hexane and filtered. The filtrate was concentrated and the residue was chromatographed on a silica gel column. Elution with 5–10% ethyl acetate in hexane afforded th title compound (3.59 g) as a colorless solid.

(C) [3R-[1(R*),3α,4α]]-1-(1-Benzyloxycarbonyl-2-pyrrolidinyl)methyl]-3-hydroxy-1,3,4,5-tetrahydro-4-(4-methoxyphenyl)-6-trifluoromethyl)-2H-1-benzazepin2-one (3R-cis)-3-Hydroxy-4-(4-methoxyphenyl)-6-(trifluoromethyl)-2H-1-benzazepin-2-one (2.46 g, 7 mmol) was added to a suspension of sodium hydride (0.25 g, 10.5 mmol) in dimethylformamide (70 ml). The mixture was stirred at room temperature for 1 hour and R-1-(benzyloxycarbonyl)-2-(bromomethyl)pyrrolidine (3 g, 10.5 mmol) was added. The reaction mixture was heated at 80° C. for 4 hours and additional methanol (0.08 g, 3.5 mmol) was added. After an additional 2 hours at 80° C., the mixture was cooled and quenched with water. It was extracted with ethyl acetate three times. Combined extracts were washed with 10% aqueous lithium chloride solution, dried (magnesium sulfate) and concentrated. The crude residue was chromatographed on a silica gel column and eluted with 1% methanol in dichloromethane to obtain the title compound (4.32 g), contaminated with unreacted (3R-cis)-3-hydroxy-4-(4-methoxyphenyl)-6-(trifluoromethyl)-2H-1-benzazepin-2-one.

(D) [3R-[1(R*),3α,4α)]-1,3,4,5-Tetrahydro-3-hydroxy-4-(4-methoxyphenyl)-1-(2-pyrrolidinylmethyl)-6-(trifluoromethyl)-2H-1-benzazepin-2-one, monohydrochloride Ammonium formate (1.8 g, 28.3 mmol) was added in one portion to a suspension of 10% palladium on charcoal (1 g) and [3R-[1(R*),3α,4α]]-1-(1-benzyloxycarbonyl-2-pyrrolidinyl)methyl]-3-hydroxy-1,3,4,5-tetrahydro-4-(4-methoxyphenyl)-6-trifluoromethyl)-2H-1-benzazepin-2-one (3.5 g, 5.66 mmol) in methanol (60 ml).

The mixture was heated under reflux for 1.5 hours, cooled and filtered through Celite. The residual solid was washed with chloroform. Combined filtrates were concentrated and the residue was chromatographed on a silica gel column. Elution with 3–10% methanol in dichloromethane afforded the free base of the title compound. The free bases was dissolved in ether and treated with excess etheral hydrogen chloride solution. Concentration under reduced pressure and finally an vacuo afforded the title compound (0.21 g) as a white solid, melting point 147°–151° C. $[α]_D = +108.5°$ (C=1.0, methanol).

Analysis calc'd for $C_{23}H_{25}F_3N_2O_3 \cdot HCl \cdot 1.0H_2O$: C,56.50; H,5.77; N,5.73; Cl,7.25; F,11.66; Found: C,56.76; H,5.74; N,5.50; Cl,7.12; F,11.36.

EXAMPLE 16

[3R-[1(S*),3α,4α]]-1,3,4,5-Tetrahydro-3-hydroxy-4-(4-methoxyphenyl)-1-(2-pyrrolidinylmethyl)-6-(trifluoromethyl)-2H-1-benzazepin-2-one, monohydrochloride (A) [3R-[1(S*),3α,4α]]-1-(1-Benzyloxycarbonyl-2-pyrrolidinyl)methyl]-3-hydroxy-1,3,4,5-tetrahydro-4-(4-methoxyphenyl)-6-(trifluoromethyl)-2H-1-benzazepin-2-one (3R-cis)-3-Hydroxy-4-(4-methoxyphenyl)-6-(trifluoromethyl)-2H-1-benzazepin-2-one (1.41 g, 4 mmol) was added to a suspension of sodium hydride (0.19 g, 4.8 mmol) in dimethylformamide (40 ml). After 1 hour, (S)-1-(benzyloxycarbonyl)-2-(bromomethyl)pyrrolidine (1.7 g, 6 mmol) was added and the mixture was heated to 80° C. for 1.5 hours. Additional sodium hydride (0.05 g, 2 mmol) and (3R-cis)-3-hydroxy-4-(4-methoxyphenyl)-6-(trifluoromethyl)-2H-1-benzazepin-2-one (0.57 g, 2 mmol) were added. The reaction mixture was heated for an additional 2 hours, cooled and quenched by the addition of water. It was extracted with ethyl acetate three times. Combined ethyl acetate extracts were washed with 10% aqueous lithium chloride solution, dried (magnesium sulfate) and concentrated. The crude residue was chromatographed on a silica gel column and eluted with 30–50% ethyl acetate in hexane to afford the title compound (1.12 g) as a white foam.

(B) 3R-[1(S*),3α,4α]]-1,3,4,5-tetrahydro-3-hydroxy-4-(4-methoxyphenyl)-1-(2-pyrrolidinylmethyl)-6-(trifluoromethyl)-2H-1-benzazepin-2-one, monohydrochloride Ammonium formate (0.57 g, 9.1 mmol) was added to a suspension of 10% palladium on charcoal (0.34 g) and 3R-[1(S*),3α,4α)]-1-(1-benzyloxy-carbonyl-2-pyrrolidinyl)methyl]-3-hydroxy-1,3,4,5-tetrahydro-4-(4-methoxyphenyl)-6-(trifluoromethyl)-2H-1-benzazepin-2-one (1.12 g, 1.82 mmol) in methanol (40 ml). The mixture was heated under reflux for 30 minutes, cooled and filtered through anhydrous magnesium sulfate. Residual solid was washed with ethyl acetate. Combined filtrate was concentrated and was then chromatographed on a silica gel column. Elution with 2–5% methanol in ethyl acetate followed by 10% methanol in dichloromethane to afford the free base of the title compound (0.72 g). The free base was dissolved in ethyl acetate and treated with excess ethereal hydrogen chloride solution, concentrated and dried in vacuo at 70° C.

to yield the title compound (0.64 g), m.p. 159°–163° C. ]α]$_D$= +71.3° (C=1.0, methanol).

Analysis calc'd for $C_{23}H_{25}F_3N_2O_3 \cdot HCL \cdot 0.5H_2O$: C,57.56; H,5.67; N,5.84; Cl,7.39; F,11.88; Found C,57.34; H,5.84; N,5.62; Cl,7.31; F,12.17.

EXAMPLE 17

(3R-cis)-3-(Acetyloxy)-1-2-(dimethylamino)-2methyl-propyl]-1, 3, 4, 5-tetrahydro-4-(4-methoxyphenyl)-6-(trifluoromethyl)-2H-1-benzazepin-2one, monohydrochloride A stirred solution of 1.9 g (3.9 mmol) of (3R-cis)-1-2-(dimethylamino)-2-methylpropyl]-1,3,4,5-tetrahydro-3-hydroxy-4-(4-methoxyphenyl)-6,-(trifluoromethyl)-2H-1-benzazepin-2-one, monohydrochloride (see Example 10) was heated in 50 ml of acetic anhydride heated in an oil bath at 110°–124° C. (bath temperature). Acetylation was comparatively slow and approximately 4.25 hours of heating was necessary before the starting material was no longer seen by TLC. Concurrently, a high $R_f$, by-product gradually formed during the heating. After cooling, the bulk of acetic anhydride was removed on a rotary evaporator at 0.2 mm and the residual oil (3.6 g) was taken up in 10 ml of ethyl acetate. Since no crystallization occurred, the ethyl acetate was evaporated and the oil rubbed under ether to give a solid. Most of the ether was decanted and the material was rubbed under fresh ether and cooled overnight.

The colorless solid which had become gelatinous was filtered under argon, washed with ether (hygroscopic), and dried in vacuo. Once free of solvent the solid was no longer hygroscopic and could be exposed to the atmosphere; weight 1.23 g; melting point 88°–91° C. (bubbles); sintering at 81° C. [α]$_D$= +104° (C=1.0, methanol).

Analysis calc'd for $C_{26}H_{31}N_2O_4 \cdot HCl \cdot H_2O$: C,57.09; H,6.26; N,5.12; Cl,6.48; Found: C,57.46; H,6.46; N,4.84; Cl,6.33.

EXAMPLE 18

(3R-cis)-1-1-(Dimethylamino)methyl]propyl]-1,3,4,5-tetrahydro-3-hydroxy-4-(4-methoxyphenyl)-6-(trifluoromethyl)-2H-1-benzazepin-2-one, isomer B monohydrochloride

(A)

(3R-cis)-3-(t-Butyldimethylsiloxy)-4-(4-methoxyphenyl)-6-(trifluoromethyl)-2H-1-benzazepin-2-one To a stirred solution of 10 g of (3(R)-cis)-3-hydroxy-4-(4-methoxyphenyl)-6-(trifluoromethyl)-2H-1-benzazepin-2-one (28.5 mmol) and 4.85 g of imidazole (71.2 mmol) in 10ml of dry dimethylformamide at 35° C. was added 5.10 g of t-butyldimethylsilyl chloride. The solution was stirred at 35° C. overnight, cooled to room temperature and partitioned between ether and water. The organic phase was washed with water and brine, dried (magnesium sulfate) and evaporated to afford 14.2 g of the title compound as an amorphous solid, melting point 114°–116° C.

(B)

(3R-cis)-3-(t-Butyldimethylsiloxy)-1-1-(cyano)propyl]-4-(4-methoxyphenyl)-6-(trifluoromethyl)-2H-1-benzazepin-2-one To a stirred suspension of 0.54 g of sodium hydride (11.2 mmol of a 50% oil dispersion) in 10 ml of dry dimethylformamide was added 4 g of (3R-cis)-3-(t-butyldimethylsiloxy)-4-(4-methoxyphenyl)-6-(trifluoromethyl)-2H-1-benzazepin-2-one (8.6 mmol) in one portion as a solid. The solution was stirred 30 minutes, 1.33 g of 2-chlorobutyronitrile (12.9 mmol) was added neat and the solution was heated to 75° C for 1 hour. An additional 0.15 g of sodium hydride and 0.3 g of 2-chlorobutyronitrile were added and the solution was heated at 75° C. for 45 minutes. The solution was quenched with 1M ammonium chloride and dimethylformamide was remove under vacuum with gentle warming. The residue was partitioned between ether and 1M ammonium chloride, the organic phase was washed with water and brine, dried (magnesium sulfate) and evaporated to afford 4.68 g of brown gum. Thin-layer chromatography (50% ether/hexane) indicated a 3:2 mixture of the diastereomers of the product, the faster-moving isomer ($R_f$=0.63) and the slower-moving isomer ($R_f$=0.56). Flash chromatography on silica (30% ether/hexane) afforded 1.10 g of the title compound, the faster-moving isomer, as a white solid, melting point 54°–57° C.

(C)

(3R-cis)-1-1-(Amino)methyl)propyl]-3-(t-butyldimethylsiloxy)-4-(4-methoxyphenyl)-6-(trifluoromethyl)-2H-1-benzazepin-2-one A solution of 1.10 g of (3R-cis)-3-(t-butyldimethylsiloxy)-1-1-(cyano)propyl]-4-(4-methoxyphenyl)-6-(trifluoromethyl)-2H-1-benzazepin-2-one (2.06 mmol) and 0.27 g of rhodium on alumina in 100 ml of ammonia-saturated methanol was hydrogenated at 50psi for 6 hours. An additional 0.10 g of rhodium on alumina was added, the solution was resaturated with ammonia and the solution was hydrogenated at 50psi for an additional 2 hours. The solution was filtered through Celite, the Celite rinsed twice with methanol and the combined filtrates were evaporated to afford 1.17 g of foamy solid. Flash chromatography on silica (2% methanol/0.5% triethylamine/dichloromethane) afforded 0.70 g

(D)

(3R-cis)-1-1-(Dimethylamino)methyl]propyl]-3-(t-butyldimethylsiloxy)-4-(4-methoxyphenyl)-6-(trifluoromethyl)-2H-1-benzazepin-2-one To 0.26 g of solid sodium cyanoborohydride (4.2 mmol) at 0° C. was added in portions with stirring a solution of 0.70 g of (3R-cis)-1-[1-[(amino)methyl]propyl-3-(t-butyldimethylsiloxy)-4-(4-methoxyphenyl)-6-(trifluoromethyl)-2H-1-benzazepin- 2-one (1.30 mmol) and 1.2 ml of 37% aqueous formaldehyde in 10 ml of acetonitrile followed by 0.14 ml of neat acetic acid. The ice bath was removed, the solution was stirred for 2 hours, another 0.05 ml of acetic acid was added and the solution was stirred for 30 minutes. The solution was partitioned between ether and 10% aqueous potassium carbonate, the ether layer was washed with brine, dried (manesium sulfate) and evaporated to afford 0.91 g of thick oil. Flash chromatography on silica (1% methanol/0.2% triethylamine/dichloromethane) afforded 0.49 g of the title compound as a clear gum.

(E)

(3R-cis)-1-1-(Dimethylamino)methyl]propyl]-1,-3,4,5-tetrahydro-3-hydroxy-4-(4-methoxyphenyl)-6-(trifluoromethyl)-2H-1-benzazepin-2-one, isomer B, monohydrochloride To a solution of 0.49 g of (3R-cis)-1-[(dimethylamino)methyl]propyl]-3-(t-butyldimethyl-siloxy)-4-

(4-methoxyphenyl)-6-(trifluoromethyl)-2H-1-benzazepin-2-one (0.87 mmol) in 10 ml of dry dimethylformamide was added 0.55 g of tetrabutylammonium fluoride trihydrate (1.74 mmol) in one portion as a solid. The solution was stirred for 20 minutes, partitioned between ether and water and the organic layer was washed with brine, dried (magnesium sulfate) and evaporated to afford 0.49 g of semi-solid. Preparative thin layer chromatography (3 plates, 5% methanol/dichloromethane) afforded 0.35 g of the free base of the title compound as a white crystalline solid. The free base was suspended in ether, ethyl acetate was added until dissolution and hydrogen chloride saturated ether was added. The resulting white solid was quickly collected by filtration, washed with ether and dried under vacuum to afford 0.24 g of the title compound as a white solid, m.p. 144°–148° C., $[\alpha]_D = +89.60°$ (C=1, methanol).

Analysis calc'd. for $C_{24}H_{30}ClF_3N_2O_3 \cdot 1.06H_2O$: C,56.96; H,6.38; N,5.45; F,11.11; Cl,7.24; Found: C,56.96; H,6.40; N,5.54; F,11.26; Cl,7.00.

EXAMPLE 19

(3R-cis)-1-1-(Dimethylamino)methyl]propyl-1,3,-4,5-tetrahydro-3-hydroxy-4-(4-methoxyphenyl)-6-(trifluoromethyl)-2H-1-benzazepin-2oone, isomer A, monohydrochloride (A)

(3R-cis)-3-(t-Butyldimethylsiloxy)-1-1-(cyano)propyl]-4-(4-methoxyphenyl)-6-(trifluoromethyl)-2H-1-benzazepin-2-one No clean slower-moving isomer (SMI) was obtained from the chromatography of the nitrile mixture described for (3R-cis)-1-1-(dimethylamino)methyl]-propyl]-1,3,4,5-tetrahydro-3-hydroxy-4-(4-methoxyphenyl)-6-(trifluoromethyl)-2H-1-benzazepin-2-one, monohydrochloride (see Example 8). Fractions containing SMI were pooled and evaporated to afford 1.91 g of solid. This material was flash chromatographed on silica (25% ether/hexane) to afford 1.21 g of the nearly clean SMI of the title compound as a white solid.

(B)

(3R-cis)-1-1-(Amino)methyl]propyl]-3-(t-butyldimethylsiloxy)-4-(4-methoxyphenyl)-6-(trifluoromethyl)-2H-1-benzazepin-2-one A solution of 1.21 g of (3R-cis)-3-(t-butyldimethylsiloxy)-1-1-(cyano)propyl]-4-(4-methoxyphenyl)-6-(trifluoromethyl)-2H-1-benzaze-pin-2-one (2.27 mmol) and 0.30 g of 5% rhodium on alumina in 75 ml of ammonia-saturated methanol was hydrogenated at 50 psi for 5 hours. The solution was filtered through Celite, the Celite rinsed twice with methanol and the combined filtrates were evaporated to afford 1.36 g of crude title compound as a clear gum.

(C)

(3R-cis)-1-1-(Dimethylamino)methyl]propyl]-3-(t-butyldimethylsiloxy)-4-(4-methoxyphenyl)-6-(trifluoromethyl)-2H-1-benzazepin-2-one To 0.46 g of solid sodium cyanoborohydride (7.26 mmol) at 0° C. was added in portions with stirring a solution of 1.36 g of (3R-cis)-1-1(amino)methyl]-propyl]-3-(t-butyldimethylsiloxy)-4-(4-methoxyphenyl)-6-(trifluoromethyl)-2H-1-benzazepin-2-one (2.27 mmol) and 2.1 ml of 37% aqueous formaldehyde in 20 ml of acetonitrile followed by 0.3 ml of neat acetic acid. The ice bath was removed, the solution was stirred for 2 hours, another 0.15 ml of acetic acid was added and the solution was stirred for 2 hours. The solution was partitioned between ether and 10% aqueous potassium carbonate, the ether layer was washed with 10% aqueous potassium carbonate and brine, dried (magnesium sulfate) and evaporated to afford 1.31 g of a clear gum. Flash chromatography on silica (1% methanol/0.5% triethylamine/dichloromethane) afforded 1.02 g of a white foamy solid containing crude title compound. This material was chromatographed on 6 preparative thin layer plates (25% ethyl acetate/hexane) and the band with Rf=0.52 was excised and extracted with 5% methanol/dichloromethane. The extract was filtered and the filtrate evaporated to afford 0.44 g of the title compound as a light tan gum.

(D)

(3R-cis)-1-1-(Dimethylamino)methyl]propyl]-1,3,4,5-tetrahydro-3-hydroxy-4-(4-methoxyphenyl)-6-(trifluoromethyl)-2H-1-benzazepin-2-one, isomer A, monohydrochloride To a solution of 0.44 g of (3R-cis)-1-1-(dimethylamino)methyl]propyl]-3-(t-butyldimethylsiloxy)-4-(4-methoxyphenyl)-6-(trifluoromethyl)-(2H-1-benzazepin-2-one (0.78 mmol) in 10 ml of dry dimethylformamide was added 0.49 g of tetrabutylammonium fluoride trihydrate (1.56 mmol) in one portion as a solid. The solution was stirred for 25 minutes, partitioned between ether and water and the organic layer was washed with brine, dried (magnesium sulfate) and evaporated to afford 0.45 g of tan gum. Preparative thin layer chromatography (3 plates, 2% methanol/dichloromethane) afforded 0.36 g of the free base of the title compound as a white crystalline solid. The free base was dissolved in ether, the solution was filtered through Celite and hydrogen chloride saturated ether was added to the filtrate. The resulting white solid was collected by filtration, washed twice with ether and dried under vacuum to afford 0.35 g of the title compound as a white solid, m.p. 126°–131° C., $[\alpha]_D = +106.8$ (c=1, methanol).

Analysis calc'd. for $C_{24}H_{30}ClF_3N_2O_3 \cdot 0.78H_2O$: C,57.54; H,6.35; N,5.59; Cl,7.08; F,11.38; Found: C,57.54; H,6.39; N,5.64; Cl,6.96; F,11.09.

EXAMPLE 20

(3R-cis)-1,3,4,5-Tetrahydro-3-hydroxy-4-(4-methoxyphenyl)-1-1-methyl-2-(methylamino)ethyl]-6-(trifluoromethyl)-2H-1-benzazepin-2-one, isomer B monohydrochloride (A)

(3R-cis)-3-(t-Butyldimethylsiloxy)-1-(1-cyanoethyl)-4-(4-methoxyphenyl)-6-(trifluoromethyl)-2H-1-benzazepin-2-one To a stirred solution of (3R-cis)-3-(t-butyldimethylsiloxy)-4-(4-methoxyphenyl)-6-(trifluoromethyl)-2H-1-benzazepin-2-one (4 g, 8.60 mmol; see Example 18) in dry dimethylformamide (40 ml) was added sodium hydride as a 60% oil dispersion (380mg, 9.50 mmol). The solution was stirred at room temperature for 30 minutes and 2-chloropropionitrile (0.68 ml, 8.66 mmol) was added neat. The solution was heated to 50° C. for 1 hour, an additional 0.02 g of sodium hydride and 0.07 ml of 2-chloropropionitrile were added and the reaction was heated at 50° C. for 3 hours. The solution was cooled to room temperature, concentrated in vacuo to remove dimethylformamide and the brown residue was partitioned between ethyl acetate and water. The organic phase was washed with water and brine, dried (magnesium sulfate) and evaporated and the residue was applied to a column of silica gel. Elution with 5% ethyl acetate:hexanes afforded 1.76 g of the faster-moving isomer, of the title compound, and 1.0 g of the slower-moving isomer.

(B)
(3R-cis)-1-1-(Amino)methyl]ethyl]-3-(t-butyldimethylsiloxy)-4-(4-methoxyphenyl)-6-(trifluoromethyl)-2H-1-benzazepin-2-one A solution of (3R-cis)-3-(t-butyldimethylsiloxy)-1-(1-cyanoethyl)-4-(4-methoxyphenyl)-6-(trifluoromethyl)-2H-1-benzazepin-2-one (0.8 g, 1.5 mmol) in methanol (100 ml) was saturated with gaseous ammonia at 0° C. for 5 minutes and 5% rhodium on alumina (0.2 g) was added. The solution was hydrogenated at 45 psi for 1.5 hours, additional catalyst (100 mg) was added and the solution was hydrogenated at 55 psi for an additional 1 hour. The mixture was filtered through a pad of Celite, which was rinsed with methanol. The combined filtrates were evaporated to afford 0.75 g of the title compound.

(C)
(3R-cis)-1-1-(Trifluoroacetylamino)methyl]-ethyl]-3-(t-butyldimethylsiloxy)-4-(4-methoxyphenyl)-6-(trifluoromethyl)-2H-1-benzazepin-2-one To a solution of (3(R)-cis)-1-1-(amino)methyl]ethyl]-3-(t-butyldimethylsiloxy)-4-(4-methoxyphenyl)-6-(trifluoromethyl)-2H-1-benzazepin-2-one (0.76 g, 1.46 mmol) and pyridine (0.37 ml, 4.66 mmol) in dichloromethane (10 ml) was added a solution of trifluoroacetic anhydride (0.41ml, 2.91 mmol) in 5 ml of dichloromethane over 2 minutes and the solution was stirred at room temperature overnight. Additional pyridine (0.37 ml, 4.66 mmole) and trifluoroacetic anhydride (0.41 ml) in 5 ml dichloromethane were added and the solution was stirred for 20 minutes. The solution was extracted with water and brine, dried (magnesium sulfate) and evaporated to afford 0.77 g of the title compound as a red oil.

(D)
(3R-cis)-1-1-((Trifluoroacetyl)methylamino)methyl]ethyl]-3-(t-butyldimethylsiloxy)-4-(4-methoxyphenyl)-6-(trifluoromethyl-2H-1-benzazepin-2-one To a solution of (3R-cis)-1-1-(trifluoroacetylamino)-methyl]ethyl]-3-(t-butyldimethylsiloxy)- 4-(4-methoxyphenyl)-6-(trifluoromethyl)-2H-1-benzazepin-2-one (570 mg, 0.94 mmole) in dry dimethylformamide (5 ml) was added sodium hydride as a 60% oil dispersion (44.9 mg, 1.12 mmole). The solution was stirred for 30 minutes at room temperature, methyl iodide (0.07 ml, 1.12 mmol) was added and the solution was stirred at room temperature for 2 hours. The solution was partitioned between ethyl acetate and water, the organic phase was washed with water and brine, dried (magnesium sulfate) and evaporated to afford 450 mg of the title compound as a red oil.

(E)
(3R-cis)-1-1-(Methylamino)methyl]ethyl]-3-(t-butyldimethylsiloxy)-4-(4-methoxyphenyl)-6-(trifluoromethyl)-2H-1-benzazepin-2-one A mixture of (3R-cis)-1-1-((trifluoroacetyl)methylamino)methyl]ethyl]-3-(t-butyldimethylsiloxy)-4-(4-methoxyphenyl)-6-(trifluoromethyl)-2H-1-benzazepin-2-one (450mg, 0.72 mmole) and sodium carbonate (0.5 g, 4.72 mmole) in methanol (20 ml) was refluxed overnight. The reaction was cooled to room temperature and evaporated and the residue was partitioned between dichloromethane and water. The organic phase was washed with water and brine, dried (magnesium sulfate) and evaporated. The residue was applied to 3 preparative silica gel plates which were eluted with 5% methanol:dichloromethane. The product bands were cut and extracted with 5% methanol: dichloromethane:0.5% triethylamine. The mixture was filtered through a pad of Celite and the pad was rinsed with dichloromethane. The combined filtrates were evaporated and the residue was chased with toluene to afford 230 mg of the title compound as a yellow oil.

(F)
(3R-cis)-1,3,4,5-Tetrahydro-3-hydroxy-4-(4-methoxyphenyl)-1-[1-methyl-2-(methylamino)-ethyl]-6-(trifluoromethyl)-2H-1-benzazepin-2-one, isomer B monohydrochloride To a solution of (3R-cis)-1-[1-[(methylamino)methyl]ethyl]-3-(t-butyldimethylsiloxy)-4-(4-methoxyphenyl)-6-(trifluoromethyl)-2H-1- benzazepin-2-one (1.2 g, 2.24 mmol) in dry tetrahydrofuran (50 ml) was added tetrabutylammonium fluoride trihydrate (1.06 g, 3.36 mmol). The solution was stirred overnight, evaporated and the residue was partitioned between dichloromethane and water. The organic phase was washed with water and brine, dried (magnesium sulfate) and evaporated to afford 0.86 g of a yellow oil. The residue was applied to 4 preparative silica gel plates, which were eluted with 10% methanol:dichloromethane. Product bands were cut and extracted with 15% methanol:dichloromethane:0.5% triethylamine. The compound was dissolved in ether and a solution of hydrogen chloride saturated ether was added to afford a white solid which was filtered and rinsed with ether to afford 320 mg of pure title compound, m.p. 178°–180° C., $[\alpha]_D = +63.90$ (C=1,ethanol).

Analysis calc'd for $C_{22}H_{25}F_3N_2O_3HCl \cdot 0.98H_2O$: C, 55.45; H, 5.90; N, 5.73; Cl, 7.94; F, 11.61; Found: C, 55.45; H, 5.91; N, 5.88; Cl, 7.44; F, 11.96.

EXAMPLE 21

(cis)-1-(2-Aminophenyl)-1,3,4,5-tetrahydro-4-(4-methoxyphenyl)-3-methyl-6-(trifluoromethyl)-2H-1-benzazepin-2-one, monohydrochloride (A)
(cis)-1-(2-Nitrophenyl)-1,3,4,5-tetrahydro-4-(4-methoxyphenyl)-3-methyl-6-(trifluoromethyl)-2H-1-benzazepin-2-one To a solution of 125 mg of sodium hydride (3.15 mmol of a 60% oil dispersion) in 5 ml of dry dimethylformamide was added 1.0 g (2.86 mmol) of (cis)-1,3,4,5-tetrahydro-4-(4-methoxyphenyl)-3-methyl-(6-trifluoromethyl)-2H-1-benzazepin-2-one. The solution was stirred at room temperature for 35 minutes and 0.32 ml (3.0 mmol) of 2-fluoronitrobenzene was added neat dropwise. The solution was stirred at room temperature for 105 minutes and heated to 45° C. for 40 minutes. Solvent was removed under high vacuum with gentle warming and the residue was partitioned between ether and 1M ammonium chloride. The organic layer was washed twice with water and once with brine, dried and evaporated to afford a yellow foamy solid which was dissolved in 25 ml of ether. Addition of 175 ml of hexane and cooling overnight afforded 0.78 g of the title A compound (58%) as a yellow crystalline solid.

(B)
(cis)-1-(2-Aminophenyl)-1,3,4,5-tetrahydro-4-(4-methoxyphenyl)-3-methyl-6-(trifluoromethyl)-2H-1-benzazepin-2-one, monohydrochloride A solution of 0.73 g (1.55 mmol) of the title A compound and 146 mg of 10% palladium on carbon in 50 ml of absolute ethanol was hydrogenated for 4.25 hours and filtered through celite. The celite was rinsed twice with ethanol and the combined filtrates were evaporated. The residue was twice dissolved in CCl$_4$ and evaporated to afford 0.73 g of white foamy solid which $^1$H and $^{13}$C NMR spectra indicated was the nearly clean free base of the product. The residue was dissolved in 50 ml of ether and filtered of cloudiness through celite. After addition of HCl-saturated ether and standing for 30 minutes, the white precipitate was collected by filtration, rinsed twice with ether and dried under vacuum at 75° C. for several days to yield 0.58 g (79%) of the title compound as a white powdery solid, m.p. 165°–170° C.

Analysis calc'd for $C_{25}H_{23}F_3N_2O_2 \cdot 0.9HCl \cdot 0.19H_2O$: C, 63.00; H, 5.13; N, 5.88; F, 11.96; Cl, 6.69; Found: C, 63.00; H, 4.87; N, 6.03; F, 11.79; CCl, 6.55.

EXAMPLE 22

(3R-cis)-1-[2-(Dimethylamino)phenyl]-1,3,4,5-tetrahydro-3-hydroxy-4-(4-methoxyphenyl)-6-(trifluoromethyl)-2H-1-benzazepin-2-one, monohydrochloride (A)
(3R-cis)-1-(2-Nitrophenyl)-1,3,4,5-tetrahydro-4-(4-methoxyphenyl)-3-hydroxy-6-(trifluoromethyl)-2H-1-benzazepin-2-one To a solution of (3R-cis)-3-hydroxy-4-(4-methoxyphenyl)-6-(trifluoromethyl)-2H-1-benzazepin-2-one (2 g, 5.69 mmol) in dry dimethylformamide (10 ml) was added sodium hydride as a 60% oil dispersion (230 mg, 5.69 mmol). The solution was stirred at room temperature for 1 hour and was added dropwise to a solution of 1-fluoro-2-nitrobenzene (1.2 ml, 11.38 mmole) in 5 ml of dimethylformamide over 2 hours. The reaction was stirred overnight at room temperature, concentrated in vacuo to remove dimethylformamide and the residue was partitioned between ethyl acetate and 1N aqueous hydrochloric acid. The organic phase was washed with water and brine, dried over magnesium sulfate and evaporated to afford a yellow oil. The oil was dissolved in warm ethyl acetate and the yellow solid which crystallized out of solution was filtered and rinsed with cold ethyl acetate to afford 1.68 g (63%) of the title A compound (B)
(3R-cis)-1-(2-Nitrophenyl)-1,3,4,5-tetrahydro-4-(4-methoxyphenyl)-3-acetyloxy-6-(trifluoromethyl)-2H-1-benzazepin-2-one To a stirred solution of the title A compound (1.68 g, 3.56 mmole) and 4-dimethylaminopyridine (50 mg) in tetrahydrofuran (50 ml) was added pyridine (0.32 ml, 3.92 mmol) followed by acetic anhydride (0.44 ml, 4.63 mmol) and the reaction was stirred overnight at room temperature. The solution was partitioned between ethyl acetate and water. The aqueous phase was extracted with ethyl acetate (3×50 ml). The combined organic phases were washed with water, 1N sodium hydrogen carbonate, and brine and dried over magnesium sulfate. The solvent was removed in vacuo to afford 0.85 g (46%) of the title B compound as a yellow solid.

(C)
(3R-cis)-1-(2-Aminophenyl)-1,3,4,5-tetrahydro-4-(4-methoxyphenyl)-3-acetyloxy-6-(trifluoromethyl)-2H-1-benzazepin-2-one To a solution of the title B compound (0.85 g, 1.65 mmol) in 100 ml of acetonitrile was added 10% palladium on carbon (0.2 g). The solution was hydrogenated at 50 psi for 3 hours. The mixture was filtered through a pad of celite, which was rinsed with acetonitrile. The combined filtrates were evaporated to afford 0.60 g (75%) of the title C compound.

(D)
(3R-cis)-1-(2-Dimethylaminophenyl)-1,3,4,5-tetrahydro-4-(4-methoxyphenyl)-3-acetyloxy-6-(trifluoromethyl)-2H-1-benzazepin-2-one, monohydrochloride A solution of the title C compound (120 mg, 0.25 mmol) and 37% formaldehyde (0.6 ml) in acetonitrile (5 ml) was added to solid NaCNBH$_3$ (62 mg, 0.98 mmol). The reaction was stirred at room temperature for 5 minutes followed by the addition of 0.1 ml of acetic acid. An additional 0.1 ml of acetic acid was added after 2 hours. The solution was partitioned between ethyl acetate and aqueous potassium carbonate. The organic phase was washed with aqueous potassium carbonate, water, and brine, dried over magnesium sulfate and evaporated. The residue was dissolved in ether and a solution of HCl-saturated ether was added to afford a white solid. By $^1$H NMR, the acetyl group had partially hydrolyzed.

(E)
(3R-cis)-1-2-(Dimethylamino)phenyl]-1,3,4,5-tetrahydro-3-hydroxy-4-(4-methoxyphenyl)-6-(trifluoromethyl)-2H-1-benzazepin-2-one, monohydrochloride A mixture of the title D compound (420 mg, 0.79 mmole) and potassium carbonate (2 g) in methanol (30 ml) was refluxed under argon for 5 hours. The reaction was cooled to room temperature, concentrated in vacuo and the residue was extracted with methylene chloride. The organic phase was washed with water and brine, dried over magnesium sulfate and evaporated. The residue was applied to 4 preparative silica gel plates which were eluted with 1:1 ethyl acetate:hexanes. The product bands were cut and extracted with methylene chloride. The solution was filtered through a pad of celite and the pad was rinsed with methylene chloride. The combined filtrates were evaporated. The yellow solid was dissolved in ether and a saturated solution of HCl in ether was added. The light yellow solid was filtered and rinsed with ether to afford 302 mg (74%) of pure title compound. [α = +243.4° (c=1.3, ethanol), m.p. 217°–220° C.

Analysis calc'd for $C_{26}H_{25}F_3N_2O_3 \cdot HCl \cdot 0.72H_2O$: C, 60.07; H, 5.31; N, 5.38; Cl, 6.81; F, 10.96; Found: C, 60.07; H, 5.27; N, 5.18; Cl, 6.89; F, 10.62.

EXAMPLE 23

(3R-cis)-1,3,4,5-Tetrahydro-3-hydroxy-4-(4-methoxyphenyl)-1-(2-pyridinylmethyl)-6-(trifluoromethyl)-2H-1-benzazepin-2-one, monohydrochloride A stirred solution of 5.0 g (0.0142 mol) of (3R-cis)-3-hydroxy-4-(4-methoxyphenyl)-6-(trifluoromethyl)-2H-

1-benzazepin-2-one in 150 ml of butanone was treated with 2.8 g (0.0171 mol) of 2-chloromethylpyridine hydrochloride and 5.0 g (0.0362 mol) of pulverized potassium carbonate and heated to reflux overnight. TLC (95:5 $CH_2Cl_2$-MeOH) showed the reaction to be complete. After combining with an earlier 0.5 g run, the solids were filtered off, washed with butanone, and the bulk of the solvent was removed on a rotary evaporator. The residue was shaken with 150 ml of ethyl acetate and 50 ml of water, the layers separated, the organic phase washed with water (50 ml), brine (50 ml), dried over magnesium sulfate, and the solvent evaporated finally at 0.2 mm, to give 7.3 g of a light yellow foamy residue. After standing over the weekend, the above was taken up in ether, filtered to remove some insoluble orange material, evaporated, and pump-dried to give 6.9 g of a light yellow brittle foam. TLC: $R_f$ 0.65 (95:5 $CH_2Cl_2$-MeOH).

The above base in 50 ml of methanol was treated with 3.5 ml of 5N ethanolic hydrochloric acid and the solvent evaporated, finally at 0.2 mm the partly solid residue was rubbed under ether and the evaporation repeated to give, after pump-drying, 8.3 g of a pale yellow solid. Following crystallization from 90 ml of hot i-PrOH, the colorless product weighed 6.95 g (93%); m.p. 184°–186° (foaming), s. 170° C., $[\alpha]_D = +97.0°$ (c=1.0 MeOH).

Analysis calc'd for $C_{24}H_{21}N_2F_3O_3.HCl.0.75H_2O$: C, 58.54; H, 4.81; N, 5.69; Cl, 7.20; Found: C, 58.46; H, 5.15; N, 5.34; Cl, 7.24.

EXAMPLE 24

(3R-cis)-1,3,4,5-Tetrahydro-3-hydroxy-4-(4-methoxyphenyl)-1-(2-piperidinylmethyl)-6-(trifluoromethyl)-2H-1-benzazepin-2-one, monohydrochloride, Isomer A A solution of 3.00 g (6.09 mmol) of the title compound from Example 23 in 200 ml of ethanol was treated with 0.30 g of $PtO_2$ and placed on the Parr apparatus under 50 psi of hydrogen for 2 hours. TLC at this point indicated the reduction of the pyridyl group was complete. The catalyst was filtered under nitrogen and solvent evaporated to give a solid residue. The latter was dissolved in 30 ml of $CH_3CN$ and luted with 330 ml of ether to give a solid. This mixture was cooled overnight and filtered to give 1.29 g (43%) of Isomer A, m.p. 177°–180° C. (s. 160° C.). Isomer A was dissolved in 20 ml of hot isopropyl alcohol, filtered through filter cel (to remove trace of catalyst), cooled overnight and filtered to give 0.72 g of nearly colorless solid, $[\alpha]_D$ +112°, (c=1.0 MeOH). After recrystallization from 18 ml of hot isopropyl alcohol, the product weighed 0.63 g (21%); m.p. 177°–180° C. (s. 160° C.); $[\alpha]_D$ +113° C. (c=1.0, MeOH); $R_f$ 0.59 (80:20 $CH_2Cl_2$-MeOH).

Analysis calc'd for $C_{24}H_{27}F_3N_2O_3.HCl.0.25H_2O$: C, 58.89; H, 5.87; N, 5.72; Cl, 7.24; Found: C, 58.82; H, 5.90; N, 5.68; Cl, 7.23.

(3R-cis)-1,3,4,5-Tetrahydro-3-hydroxy-4-(4-methoxyphenyl)-1-(2-piperidinylmethyl)-6-(trifluoromethyl)-2H-1-benzazepin-2-one, monohydrochloride, Isomer B Evaporation of the filtrate obtained during the first crystallization of Isomer A yielded 1.46 g of crude Isomer B. Conversion to the free base followed by column chromatography on 35 g of silica gel using 15:1 methylene chloride and methanol gave 0.48 g of pure isomer. This material was dissolved in 5 mL of chloroform and treated with 0.22 mL of 5.1N alcoholic HCl in 3 mL of chloroform. Removal of the solvent in vacuo gave a solid which was triturated with ether to give 0.54 g of product, $[\alpha]_D = +66.0°$ (c=1.0 MeOH), m.p. 130°–140° C.

Analysis calc'd for $C_{24}H_{27}F_3N_2O_3.HCl.1.25H_2O$: C, 56.80; H, 6.05; N, 5.52; Cl, 6.98; Found: C, 56.77; H, 5.77; N, 5.39; Cl, 6.93.

EXAMPLE 25

[3R-[1(R*),3α,4α]]-1,3,4,5-Tetrahydro-3-hydroxy-4-(4-methoxyphenyl)-1-(3-piperidinyl)-6-(trifluoromethyl)-2H-1-benzazepin-2-one, monohydrochloride (A)

[3R-[1(S*),3α,4α]]-[(Benzyl-2-pyrrolidinyl)methyl]-3-hydroxy-1,3,4,5-tetrahydro-4-(4-methoxyphenyl)-6-(trifluoromethyl)-2H-1-benzazepin-2-one (B)

[3R-[1(R*),3α,4α]]-1-(Benzyl-3-piperidinyl)-3-hydroxy-1,3,4,5-tetrahydro-4-(4-methoxyphenyl)-6-(trifluoromethyl)-2H-1-benzazepin-2-one Sodium hydride (1.44 g, 59.9 mmol) was added with stirring to a solution of (3R-cis)-3-(hydroxy)-1,3,4,5-tetrahydro-4-[4-methoxyphenyl)-6-(trifluoromethyl)-2H-1-benzazepin-2-one (10 g, 28.5 mmol) in dry dimethylformamide (250 ml). After 1 hour at room temperature, the mixture was cooled to 0° C. and S-1-benzyl-2-(chloromethyl)-pyrrolidine (7.36 g, 30 mmol) was added in one portion. The mixture was warmed to room temperature and stirred for 4 hours. It was diluted with a saturated aqueous potassium bicarbonate solution and extracted with ethyl acetate (×3). The combined organic extracts were washed with 10% aqueous sodium chloride, dried over magnesium sulfate, filtered and concentrated. The orange solid was dissolved in a minimum amount of 0.5N HCl solution and extracted with ether (×3) to remove unreacted (3R-cis)-3-hydroxy-1,3,4,5-tetrahydro-4-[4-methoxyphenyl)-6-(trifluoromethyl)-2H-1-benzazepin-2-one. Solid sodium chloride was added and the aqueous layer was extracted with ethyl acetate (×3). The combined extracts were dried over magnesium sulfate, filtered and concentrated to obtain crude title A and title B compounds as a pale orange solid. The adducts of title A and title B could not be separated at this stage and were taken on to the next step without further purification.

(C)

[3R-[1(S*),3α,4α]]-1-[(2-Pyrrolidinyl)methyl]-3-hydroxy-1,3,4,5-tetrahydro-4-(4methoxyphenyl)-6-(trifluoromethyl)-2H-1-benzazepin-2-one and (D)

[3R-[1(R*),3α,4α]]-1-(3-Piperidinyl)-3-hydroxy-1,3,4,5-tetrahydro-4-(4-methoxyphenyl)-6-(trifluoromethyl)-2H-1-benzazepin-2-one Ammonium formate (9.58 g, 151.9 mmol) was added to a suspension of 10% palladium on carbon (3.7 g) and a mixture of the title A and title B compounds (18.5 g, 33 mmol) under argon in anhydrous methanol (350 ml). The mixture was heated to reflux for 5 hours, cooled and filtered through anhydrous magnesium sulfate. Residual solids were washed well with methanol. The filtrate was concentrated, dissolved in a minimal amount of water and washed with ether (×3). The aqueous layer was basified with aqueous potassium hydrogen carbonate and extracted with ethyl acetate (×3). The combined extract was washed with water, dried over magnesium sulfate, filtered and concentrated to obtain a mixture of the title C compound and the title D compound (10.89 g, 76%) as a pale yellow foam. The isomers could not be separated and were taken on to the next step without further purification.

(E)
[3R-[1(S*),3α,4α]]-1-[(Benzyloxycarbonyl-2-pyrrolidinyl)methyl]-3-hydroxy-1,3,4,5-tetrahydro-4-(4-methoxyphenyl)-6-trifluoromethyl)-2H-1-benzazepin-2-one and (F)
[3R-[1(R*),3α,4α]]-1-(Benzyloxycarbonyl-3-piperidinyl)-3-hydroxy-1,3,4,5-tetrahydro-4-(4-methoxyphenyl)-6-trifluoromethyl)-2H-1-benzazepin-2-one To a mixture of the title C and title D compounds (7.07 g, 16.3 mmol) in 1,4-dioxane (80 ml) and saturated aqueous potassium hydrogen carbonate (30 ml) at room temperature was added dropwise benzyl chloroformate (5.84 g, 32.5 mmol). The reaction mixture was immediately diluted with water and extracted with ethyl acetate ($\times$3). The combined extract was washed with brine, dried over magnesium sulfate, filtered and concentrated. The crude yellow liquid was chromatographed on a silica gel column and eluted with 15–30% ethyl acetate in hexane to obtain the title E compound (7.89 g, 85%, $R_f$ 0.38 (silica gel, 50% ethyl acetate/hexane)) and the title F compound (0.87 g, 9.4%, $R_f$ 0.50 (silica gel, 50% ethyl acetate/hexane)).

G.
[3R-[1(R*),3α,4α]]-1,3,4,5-Tetrahydro-3-hydroxy-4-(4-methoxyphenyl)-1-(3-piperidinyl)-6-(trifluoromethyl)-2H-1-benzazepin-2-one, monohydrochloride To a solution of the title F compound (800 mg, 1.41 mmol) in ethyl acetate (25 ml) and trifluoroacetic acid (1 ml) was added with stirring palladium hydroxide on carbon (160 mg). The reaction flask was equipped with a hydrogen filled balloon. The reaction flask was evacuated under reduced pressure and filled with hydrogen ($\times$3). The mixture was then stirred at room temperature overnight before the hydrogen was removed and magnesium sulfate (anhydrous) was added. The solids were removed by suction filtration and washed well with ethyl acetate. The filtrate was washed with aqueous potassium hydrogen carbonate ($\times$3). The combined aqueous layers were extracted with ethyl acetate and the organic extracts were combined, dried over magnesium sulfate, filtered and concentrated. The crude residue was triturated with 20 ml of ether and the precipitated free amine was filtered, collected and dried to obtain a white solid (420 mg) which was dissolved in 5 ml of CH$_2$Cl$_2$ and an ethereal HCl solution (5 ml) was added. The solution was concentrated under reduced pressure and finally in vacuo to obtain the title compound (450 mg, 68%) as a white solid, m.p. 183°–188° C., $[\alpha]_D = +102.6$ (c=1, MeOH).

Analysis calc'd for C$_{23}$H$_{25}$F$_3$N$_2$O$_3$.HCl.H$_2$O:
C, 56.51; H, 5.77; N, 5.73; Cl, 7.25;
Found: C, 56.58; H, 5.75; N, 5.53; Cl, 7.02.

EXAMPLE 26
[3R-[1(R*),3α,4α]]-3-(Acetyloxy)-1,3,4,5-tetrahydro-4-(4-methoxyphenyl)-1-(3-piperidinyl)-6-(trifluoromethyl)-2H-1-benzazepin-2-one, monohydrochloride A.
[3R-[1(R*),3α,4α]]-1-(Benzyloxycarbonyl-3-piperidinyl)-3-acetyloxy-1,3,4,5-tetrahydro-4-(4-methoxyphenyl)-6-(trifluoromethyl)-2H-1-benzazepin-2-one A solution of the title F compound from Example 25 (880 mg, 1.53 mmol) in ethyl acetate (20 ml) was treated dropwise with acetyl chloride (700 μl. The reaction mixture was heated to 70° C. for 24 hours, whereupon it was cooled and excess acetyl chloride was destroyed by addition of methanol (2 ml). The mixture was diluted with ethyl acetate and washed with aqueous potassium hydrogen carbonate ($\times$3). The combined aqueous wash was extracted with ethyl acetate ($\times$1). The organic extracts were combined, dried over magnesium sulfate, filtered and concentrated under reduced pressure to obtain the title A compound (920 mg, 100%) as a white foam.

(B)
[3R-[1(R*),3α,4α]]-3-(Acetyloxy)-1,3,4,5-tetrahydro-4-(4-methoxyphenyl)-1-(3-piperidinyl)-6-(trifluoromethyl)-2H-1-benzazepin-2-one, monohydrochloride To a solution of the title A compound (920 mg, 1.53 mmol) in ethyl acetate (25 ml) and trifluoroacetic acid (1 ml) was added with stirring 200 mg palladium hydroxide on carbon (Pearlman's catalyst). The reaction flask was equipped with a hydrogen filled balloon. The flask was evacuated under reduced pressure and filled with hydrogen from the balloon ($\times$3). It was then stirred at room temperature overnight, whereupon the balloon was removed. Anhydrous magnesium sulfate was added to the reaction mixture and it was filtered through a pad of magnesium sulfate. The solids were washed well with ethyl acetate. The filtrate was washed with aqueous potassium hydrogen carbonate ($\times$3). The combined aqueous layers were extracted with ethyl acetate ($\times$2). The organic extracts were combined, dried over magnesium sulfate, filtered and concentrated. The brown, oily residue (770 mg) was chromatographed on a silica gel column (pretreated with 1% Et$_3$N) and eluted with 5% methanol in ethyl acetate to obtain the free amine (430 mg) as a white foam. The free amine was dissolved in CH$_2$Cl$_2$ and excess ethereal HCl was added. The solution was concentrated under reduced pressure to give the title compound (420 mg, 65%) as a white solid, m.p. 177°–180° C., $[\alpha]_D = +107.9°$ (c=1, MeOH).

Analysis calc'd for C$_{25}$H$_{27}$F$_3$N$_2$O$_4$.HCl.0.81H$_2$O: C, 56.91; H, 5.66; N, 5.31, Cl, 6.72; F, 10.80;
Found: C, 56.84; H, 5.67; N, 5.38; Cl, 6.41; F, 10.79.

EXAMPLE 27
[3R-[1(S*),3α,4α]]-6-Chloro-1,3,4,5-tetrahydro-3-hydroxy-4-(4-methoxyphenyl)-1-(2-pyrrolidinylmethyl)-2H-1-benzazepin-2-one A) S-N-t-Butoxycarbonyl-2-pyrrolidinemethanol S-2-Pyrrolidinemethanol (15 g, 148.3 mmol) and di-t-butyl dicarbonate (40 g, 178 mmol) in methylene chloride (500 ml) were stirred at room temperature for 5 hours. The solvent was evaporated at reduced pressure and the crude product converted to the next step (B) without further purification.

B) S-N-t-Butoxycarbonyl-2-(bromomethyl)pyrrolidine

The title A compound (29.8 g, 148.3 mmol), triphenyl phosphine (77.8 g, 297 mmol) and carbon tetrabromide (99 g, 297 mmol) in ether (1000 ml) were stirred at room temperature for 18 hours. The solid precipitate was removed by filtration and the solids washed well with hexane. Concentration of the filtrate yielded a yellow liquid which, when chromatographed on a silica gel column and eluted with 0–5% ethyl acetate in hexane, gave the title B compound (17.49 g, 45%) as a colorless liquid.

C)
[3R-[1(S*),3α,4α]]-1-[(t-Butoxycarbonyl-2-pyr- rolidinyl)methyl]-3-hydroxy-1,3,4,5,-tetrahydro-4-(4- methoxyphenyl)-6-(trifluoromethyl)-2H-1-benzazepin- 2-one (cis)-6-Chloro-4-(4-methoxyphenyl)-3-hydroxy- 1,3,4,5-tetrahydro-2H-1-benzazepin-2-one (3.0 g, 9.44 mmol) was added to a suspension of sodium hydride (0.27 g, 11.33 mmol) in dimethylformamide (95 ml, stored over 4Å mole sieve) and stirred for 1 hour. The title B compound (3.0 g, 11.33 mmol) was added and the mixture was heated to 80° C. for 3 hours. Additional sodium hydride (0.11 g, 4.58 mmol) and the title B compound (1.25 g, 4.72 mmol) were added. The reaction was heated an additional 2 hours at 80° C., cooled and quenched by the addition of water and extracted with ethyl acetate (×3). The combined extract was washed with 10% aqueous lithium chloride (×3), dried over magnesium sulfate and concentrated. The crude yellow liquid was chromatographed on a silica gel column and eluted with 5–20% ethyl acetate in hexane to isolate the title C compound (0.65 g, 13.7%, [α]$_D$+135.2° (c=1.0, methanol)).

(D)
[3R-[1(S*),3α,4α]]-6-Chloro-1,3,4,5-tetrahydro-3- hydroxy-4-(4-methoxyphenyl)-1-(2-pyrrolidinylme- thyl)-2H-1-benzazepin-2-one A solution of the title C compound (0.67 g, 1.34 mmol) and trifluoroacetic acid (1 ml, 13.1 mmol) in methylene chloride (10 ml) was stirred at room temperature for 6 hours. Saturated aqueous potassium bicarbonate was added to basify the reaction mixture, which was further diluted with water and extracted with ethyl acetate (×3). The combined extract was dried over magnesium sulfate, filtered and concentrated to give the crude product which was chromatographed on preparative silica gel plates to yield the title compound (0.28 g, 52%) as a pale yellow foam, m.p. 80°–84° C., [α]$_D$=+148.0° (c=1, MeOH).

Analysis calc'd for $C_{22}H_{25}ClN_2O_3 \cdot 0.42H_2O$:
C, 64.70; H, 6.38; N, 6.86; Cl, 8.68;
Found: C, 64.96; H, 6.34; N, 6.60; Cl, 8.78.

EXAMPLE 28
[3R-[1(S*),3α,4α]]-3-(Acetyloxy)-6-chloro-1,3,4,5-tet- rahydro-4-(4-methoxyphenyl)-1-2-pyrrolidinylmethyl)- 2H-1-benzazepin-2-one A)
[3R-[1(S*),3α,4α]]-1-[(t-Butoxycarbonyl-2-pyr- rolidinyl)methyl]-3-acyloxy)-1,3,4,5-tetrahydro-4-(4- methoxyphenyl)-6-(trifluoromethyl)-2H-1-benzazepin- 2-one N,N-dimethylaminopyridine(0.35 g, 2.88 mmol) was added to a solution of the title C compound from Example 27 (0.72 g, 1.44 mmol) and acetic anhydride (0.68 ml, 7.2 mmol) in methylene chloride (20 ml). The mixture was stirred for 18 hours at room temperature, absorbed onto silica gel (60–200 mesh), chromatographed on a silica gel column and eluted with 10–20% ethyl acetate in hexane to give the title A compound (0.66, 85%) as a white foam.

B)
[3R-[1(S*),3α,4α]]-3-(Acetyloxy)-6-chloro-1,3,4,5-tet- rahydro-4-(4-methoxyphenyl)-1-(2-pyrrolidinylme- thyl)-2H-1-benzazepin-2-one A solution of the title A compound (0.65 g, 1.20 mmol) and trifluoroacetic acid (1.37 ml, 18.0 mmol) in methylene chloride (15 ml) was stirred at room temperature for 1.5 hours. Saturated aqueous potassium hydrogen carbonate, then water were added to the reaction mixture before it was extracted with ethyl acetate (×3), dried over magnesium sulfate, filtered and concentrated to give the title compound (0.53 g, 100%) as a white foam, m.p. 74°–78° C., [α]$_D$=+130.0° (c=1, MeOH).

Analysis calc'd for $C_{24}H_{27}ClN_2O_4 \cdot 0.29H_2O$:
C, 64.33; H, 6.20; N, 6.25; Cl, 7.91;
Found: C, 64.61; H, 6.09; N, 5.97; Cl, 7.51.

EXAMPLE 29
[3R-[1(2R*),3α,4α]]-1-[2-(Dimethylamino)-1-phenyl- propyl-1,3,4,5-tetrahydro-3-hydroxy-4-(4-methoxy- phenyl)-6-(trifluoromethyl)-2H-1-benzazepin-2-one, isomer A A) 1S,2R-2-(N,N-Dimethylamino)-1-phenyl-1-propanol To a suspension of 20 g of 1S,2R-norephedrine hydrochloride (106 mmol) in 50 ml of ether was added 21 g of 25% sodium methoxide in methanol (100 mmol). An additional 50 ml of methanol was added and the solution was stirred for several minutes and filtered. The white precipitate was rinsed several times with ether and the combined filtrates were evaporated to afford 16.6 g of the free base of 1S,2R-norephedrine as a clear oil (100%). The free base was dissolved in 125 ml of acetonitrile and 42 ml of 37% aqueous formaldehyde was added. With intermittent cooling in an ice bath, 10.5 g of sodium cyanoborohydride (167 mmol) was added as a solid in portions. Again with intermittent cooling, glacial acetic acid was added dropwise until the pH of the solution dropped to 8. The solution was stirred at room temperature for 30 minutes and evaporated. The residue was extracted from 2N sodium hydroxide three times with ether and the combined ether layers were washed with 0.5N sodium hydroxide and extracted three times with 10% hydrochloric acid. The combined acidic washes were neutralized with solid sodium hydroxide and extracted three times with ether. The combined ether washes were washed with brine, dried over potassium carbonate and evaporated to afford 15.6 g of the title A compound (82%) as a white crystalline solid.

B)
1R,2R-2-(N,N-Dimethylamino)-1-phenyl-1-chloropropane

To a solution of the title A compound (15.2 g, 70.5 mmol) in 100 ml of methylene chloride was added 20.6 ml of thionyl chloride (282 mmol) in 100 ml of methylene chloride dropwise over 1 hour. Addition of 200 ml of carbon tetrachloride and cooling to 0° C. did not afford a solid product. The methylene chloride was distilled away and the remaining solution was chilled overnight to afford a 1:1 mixture of the 1R,2R and 1S,2R isomers of the title B compound as a pink solid which was collected by filtration, rinsed three times with hexane and air-dried. Recrystallization from 150 ml acetone:5 ml methanol afforded 0.98 g of the title B compound, Isomer A, as light tan prisms. $[\alpha]_D -110.9$ (c=1, methanol).

C) [8R-[1(2R*), 3α,4α]]-1-[2-(Dimethylamino)-1-phenylpropyl]-3-(t-butyldimethylsiloxy)-1,3,4,5-tetrahydro-4-(4-methoxyphenyl)-6-(trifluoromethyl)-2H-1-benzazepin-2-one, Isomer A To a suspension of 93 mg of sodium hydride (1.93 mmol of a 50% oil dispersion) in 4 ml of dry dimethylformamide was added 0.75 g of the 3-t-butyldimethylsilyl ether of (3R-cis)-3-hydroxy-4-(4-methoxyphenyl)-6-(trifluoromethyl)-2H-1-benzazepin-2-one (1.61 mmol). The solution was stirred for 10 minutes, heated to 70° C. and a solution of 0.87 g of the title B compound (3.22 mmol) and 0.36 g of KOt-Bu (3.22 mmol) in 2 ml of dry dimethylformamide was added. Heating and stirring was continued for 70 minutes, an additional 45 mg of sodium hydride and 0.22 g of the title B compound were added and the solution was heated an additional 90 minutes. The solution was quenched with aqueous potassium carbonate, dimethylformamide was removed under high vacuum with gentle warming and the residue was partitioned between ether and aqueous potassium carbonate. The organic layer was washed with brine, dried over magnesium sulfate and evaporated to afford 1.51 g of light yellow oil. Flash chromatography on silica (40% ethyl acetate/hexane) afforded 0.58 g of the title C compound as a white foamy solid, contaminated by about 20% of the imidate resulting from alkylation on the amide carbonyl oxygen.

(D)
[3R-[1(2R*),3α,4α]]-1-[2-(Dimethylamino)-1-phenylpropyl-1,3,4,5-tetrahydro-3-hydroxy-4-(4-methoxyphenyl)-6-(trifluoromethyl)-2H-1-benzazepin-2-one, isomer A To a solution of 0.58 g of crude title C compound (<1.02 mmol) in 25 ml of dry tetrahydrofuran was added 0.68 g of tetrabutylammonium fluoride trihydrate (1.56 mmol) in one portion as a solid. The solution was stirred for 20 minutes and was partitioned between ether and water. The aqueous layer was washed with ether and the combined organic layers were washed with brine, dried over magnesium sulfate and evaporated to afford 0.51 g of clear gum. This material was chromatographed on three preparative silica thin layer chromatography plates (5% methanol/methylene chloride). The band corresponding to $R_f=0.48$ (10% methanol/methylene chloride) was extracted with 10% methanol/methylene chloride/0.5% triethylamine and the solution was filtered and evaporated to afford 0.37 g of the free base of the title compound as a white foamy solid. The free base was dissolved in ether, filtered through a pad of celite, and HCl-saturated ether was added. The resulting white precipitate was collected by filtration, rinsed with ether and dried to afford 205 mg of the title compound as a white powdery solid, m.p. >220° C. $[\alpha]_D +180$ (c=1.0, methanol).

Analysis calc'd for $C_{29}H_{31}F_3N_2O_3 \cdot HCl \cdot 1.26H_2O$: C, 60.92; H, 6.09; N, 4.90; F, 9.97; Cl, 6.20;

Found: C, 60.92; H, 6.05; N, 4.74; F, 9.76; Cl, 6.11.

EXAMPLE 30

[3R-[1(2R*),3α,4α]]-1-[2-(Dimethylamino)-1-phenylpropyl]-1,3,4,5-tetrahydro-3-hydroxy-4-(4-methoxyphenyl)-6-(trifluoromethyl)-2H-1-benzazepin-2-one, monohydrochloride, Isomer B (A)
[3R-[1(2R*),3α,4α]]-1-[2-(Dimethylamino)-1-phenylpropyl]-3-(tbutyldimethylsiloxy)-1,3,4,5,-tetrahydro-4-(4-methoxyphenyl)-6-(trifluoromethyl)-2H-1-benzazepin-2-one, Isomer B To a suspension of 1.08 g of sodium hydride (22.6 mmol of a 50% oil dispersion) in 10 ml of dry dimethylformamide was added 3.5 g of the 3-tbutyldimethylsilyl ether of (3R-cis)-3-hydroxy-4-(4-methoxyphenyl)-6-(trifluoromethyl)-2H-1-benzazepin-2-one (7.52 mmol). The solution was stirred for 30 minutes, 3.05 g of a 1:1 mixture of 1R,2R and 1S,2R-(N,N-Dimethylamino)-1-phenyl-1-chloropropane (13 mmol, see Example 29) was added as a solid and the solution was stirred and heated to 65° C. for 1 hour. The solution was quenched with aqueous sodium hydrogen carbonate, dimethylformamide was removed under high vacuum with gentle warming and the residue was partitioned between ether and aqueous potassium carbonate. The organic layer was washed with brine, dried over magnesium sulfate and evaporated to afford 6.18 g of thick brown oil. Flash chromatography on silica (75% ether/hexane followed by 75% ethyl acetate/hexane) afforded 1.18 g of crude title A compound ($R_f=0.41$ in 50% ethyl acetate/hexane) contaminated with a small amount of the faster-moving isomer (compound C of Example 29). Flash chromatography of this material on silica (50% ethyl acetate/hexane) afforded 0.84 g of the title A compound (18%) as a yellow foamy solid.

(B)
[3R-[1(2R*),3α,4α]]-1-[2-(Dimethylamino)-1-phenylpropyl]-1,3,4,5-tetrahydro-3-hydroxy4-(4-methoxyphenyl)-6-(trifluoromethyl)-2H-1-benzazepin-2-one, Isomer B, monohydrochloride To a solution of 0.84 g of crude title A compound (1.34 mmol) in 25 ml of dry tetrahydrofuran was added 0.90 g of tetrabutylammonium fluoride trihydrate (2.86 mmol) in one portion as a solid. The solution was stirred for 30 minutes and was partitioned between ether and water. The aqueous layer was washed with ether and the combined organic layers were washed with brine, dried over magnesium sulfate and evaporated to afford 0.85 g of clear gum. This material was chromatographed on four preparative silica thin layer chromatography plates (75% ethyl acetate/hexane). The band corresponding to $R_f=0.19$ (75% ethyl acetate/hexane) was extracted with 5% methanol/methylene chloride and the solution was filtered and evaporated to afford 0.50 g of the free base of the title compound as a white foamy solid. The free base was dissolved in ether, filtered through a pad of celite, and HCl-saturated ether was added. The resulting white precipitate was collected by filtration, rinsed with ether and dried, but appeared hygroscopic on standing. The solid was dissolved in methanol, evaporated, suspended in hot isopropyl ether and methanol was added dropwise until dissolution occurred. The solution was cooled and the resulting white solid was collected by filtration and dried to afford 0.42 g of the title compound as a white powdery solid, m.p. 191°–192° C. $[\alpha]_D +242.6$ (c=1.05, methanol).

Analysis calc'd for $C_{29}H_{31}F_3N_2O_3 \cdot HCl \cdot 0.22H_2O$: C, 62.98; H, 5.91; N, 5.06; Cl, 6.41; F, 10.30;
Found: C, 62.98; H, 5.79; N, 5.04; Cl, 6.21; F, 10.58.

EXAMPLE 31

[3R-1(2S*),3α,4α]]-1-[(2-(Dimethylamino)-1-phenyl-propyl]-1,3,4,5-tetrahydro-3-hydroxy-4-(4-methoxyphenyl)-6-(trifluoromethyl)-2H-1-benzazepin-2-one, Isomer B, monohydrochloride

(A)
1R,2S-2-(N,N-Dimethylamino)-1-phenyl-1-propanol

To a stirred solution of 1R,2S-Norephedrine (25 g, 0.165 mol) and formaldehyde (50 ml of a 37% solution in water) in acetonitrile (150 ml) at 0° C. was added 16.3 g of sodium cyanoborohydride (0.26 mol) in several portions. Glacial acetic acid (35 ml) was added over 20 minutes. The reaction was stirred at room temperature for 1 hour, concentrated to ⅓ the volume, and neutralized to pH 10 with 1N sodium hydroxide. The solution was extracted with ether (3×100 ml). The combined organic phases were washed with water and brine, dried over magnesium sulfate and evaporated. The compound was recrystallized from ethanol:water to afford 7.01 g (24%) of the title A compound.

(B)
1R,2S-2-(N,N-Dimethylamino)-1-phenyl-1-chloropropane

To a stirred solution of the title A compound (2.19 g, 12.22 mmol) in chloroform (25 ml) was added a solution of thionyl chloride (8.89 ml, 122 mmol) in chloroform (15 ml) dropwise over 5 minutes. The reaction was stirred for 15 minutes and evaporated. The dark residue was chased with chloroform (2×100 ml) and triturated with (1:1) ether:hexanes (3×100 ml) to afford 2.28 g (80%) of the title B compound as a yellow solid, containing 15% of the 1S,2S isomer.

(C)
[3R-[1(2S*),3α,4α]]-1-[2-(Dimethylamino)-1-phenyl-propyl]-3-(t-butyldimethylsiloxy)-1,3,4,5-tetrahydro-4-(4-methoxyphenyl)-6-(trifluoromethyl)-2H-1-benzazepin-2-one, Isomer B To a stirred solution of the compound of part A of Example 18 (1.5 g, 3.22 mmol) in dry dimethylformamide (20 ml) was added sodium hydride as a 60% oil dispersion (0.39 g, 9.67 mmol). The reaction was stirred for 1 hour under argon at room temperature. The title B compound (0.76 g, 3.22 mmol) was added neat and the reaction was stirred at 50° C. overnight. The solution was cooled to room temperature and evaporated. The residue was partitioned between water and methylene chloride. The organic phase was washed with water and brine, dried over magnesium sulfate and evaporated. The residue was applied to a silica gel column and eluted with ether:hexanes (1:1) to afford 1.18 g (56%) of the title C compound.

(D)
[3R-1(2S*),3α,4α]]-1-[(2-(Dimethylamino)-1-phenyl-propyl]-1,3,4,5-tetrahydro-3-hydroxy-4-(4-methoxyphenyl)-6-(trifluoromethyl)-2H-1-benzazepin-2-one, Isomer B, monohydrochloride To a stirred solution of the title C compound (1.18 g, 1.78 mmol) in dry tetrahydrofuran (20 ml) was added tetra-n-butyl ammonium fluoride trihydrate (1.12 g, 3.56 mmol). The reaction was stirred at room temperature for 1 hour and diluted with ether. The organic phase was washed with water and brine, dried over magnesium sulfate and evaporated. The residue was applied to a silica gel column and the column was eluted with ether to afford a solid which was dissolved in ether. A solution of HCl-saturated ether was added to afford a white solid which was filtered and rinsed with ether to afford 470 mg of pure title compound, m.p. 148°–151° C. $[\alpha]_D = +167.6$ (c=0.75, CH₃OH).

Analysis calc'd for $C_{29}H_{31}F_3N_2O_3 \cdot HCl \cdot 1.87 H_2O$: C, 59.77; H, 6.18; N, 4.80; Cl, 6.08; F, 9.78;
Found: C, 59.37; H, 5.78; N, 4.90; Cl, 6.51; F, 9.84.

EXAMPLE 32

[3R-[1(2S*),3α,4α]]-1-[2-(Dimethylamino)-1-phenyl-propyl]-1,3,4,5-tetrahydro-3-hydroxy-4-(4-methoxyphenyl)-6-(trifluoromethyl)-2H-1-benzazepin-2-one, monohydrochloride, Isomer A

A)
1S,2S-2-(N,N-Dimethylamino)-1-phenyl-1-chloropropane

To a stirred solution of the compound of part A of Example 31 (2.19 g, 12.22 mmol) in chloroform (25 ml) was added a solution of thionyl chloride (8.89 ml, 122 mmol) in chloroform (15 ml) dropwise over 5 minutes. The reaction was stirred for 1 hour at room temperature and evaporated. The residue was chased with chloroform (3×100 ml) and triturated with 1:1 ether:hexanes (4×100 ml) to afford a 1:1 mixture of the 1R,2S and 1S,2S isomers as a yellow amorphous solid. Recrystallization from acetone afforded 0.8 g of the pure title A compound.

(B)
[3R-[1(2S*),3α,4α]]-1-[(2-(Dimethylamino)-1-phenyl-propyl]-3-(t-butyldimethylsiloxy)-1,3,4,5-tetrahydro-4-(4-methoxyphenyl)-6-(trifluoromethyl)-2H-1-benzazepin-2-one, Isomer A A mixture of the title A compound (0.4 g, 1.72 mmol), the compound of part A of Example 18 (0.8 g, 1.42 mmol) and Cs₂CO₃ (1.7 g, 5.16 mmol) in dry dimethylformamide (10 ml) was heated to 55° C for 2 hours. The reaction was concentrated in vacuo and the residue was triturated in water. The solid was collected and dissolved in ethyl acetate. The organic phase was dried over magnesium sulfate and evaporated. The residue was applied to silica gel and eluted with 1:1 ether/hexanes to afford 0.7 g of pure title B compound.

(C)

[3R-[1(2S*),3α,4α]]-1-[2-(Dimethylamino)-1-phenyl-propyl]-1,3,4,5-tetrahydro-3-hydroxy-4-(4-methoxyphenyl)-6-(trifluoromethyl)-2H-1-benzazepin-2-one, monohydrochloride To a stirred solution of the title B compound (0.7 g, 1.12 mmol) in dry tetrahydrofuran (20 ml) was added tetra-n-butyl ammonium fluoride trihydrate (0.35 g, 1.12 mmol). The reaction was stirred at room temperature for 2 hours and evaporated. The residue was partitioned between ethyl acetate and water. The organic phase was washed with water and brine, dried over magnesium sulfate and evaporated. The residue was applied to 4 preparative silica gel plates, which were eluted with methylene chloride. The product bands were cut and extracted with 10% methanol:methylene chloride. The compound was dissolved in ether and a solution of HCl-saturated ether was added. The solution was evaporated and chased with methanol to afford 380 mg of pure title compound as a white solid, m.p. 233°-235° C.

Analysis calc'd for $C_{29}H_{31}F_3N_2O_3 \cdot HCl \cdot 0.8H_2O$: C, 61.83; H, 6.01; N, 4.97; Cl, 6.29 F, 10.12;

Found: C, 61.77; H, 5.81; N, 5.03; Cl, 6.54; F, 10,00.

EXAMPLE 33

[3R-[1(S*),3α,4α]]-1,3,4,5-Tetrahydro-3-hydroxy-4-(4-methoxyphenyl)-1-(3-pyrrolidinyl)-6-(trifluoromethyl)-2H-1-benzazepin-2-one, fumarate (1:1) salt A) 3R-1-Benzyl-3-(p-toluenesulfonyloxy)pyrrolidine A mixture of 3R-1-benzyl-3-hydroxypyrrolidine (1 g, 5.6 mmol) and p-toluene sulfonyl chloride (1.6 g, 8.4 mmol) was stirred in pyridine (10 ml) for 4 hours. The reaction mixture was partitioned between sodium hydrogen carbonate solution and methylene chloride. The organic layer was washed with sodium hydrogen carbonate solution, followed by brine. It was then dried over sodium sulfate and concentrated first on low vacuum and finally on the high vacuum pump to remove traces of pyridine. The resultant yellow residue was flash chromatographed on a 5×25 cm SiO₂ column using ethyl acetate:hexane, 1:1 as the elutant. The pure fractions were concentrated to afford 933 mg of the title A compound as a colorless oil.

(B)

[3R-[1(S*),3α,4α]]-1-Benzyl-3-pyrrolidinyl)-3-hydroxy-1,3,4,5-tetrahydro-4-(4-methoxyphenyl)-6-trifluoromethyl)-2H-1-benzazepin 2-one A mixture of (3R-cis)-3-hydroxy-4-(4-methoxyphenyl)-6-(trifluoromethyl)-2H-1-benzazepin-2-one (911 mg, 2.60 mmol), the title A compound 900 mg; 2.72 mmol) and $Cs_2CO_3$ (4.23 g, 13 mmol) in 26 ml of distilled MEK was refluxed for 8 hours and stirred at room temperature for 18 hours. Ethyl acetate (60 ml) was added and the suspension was filtered. The filtrate was concentrated and the residue was flash chromatographed on a 5×25 cm SiO₂ column using the following elution scheme: 2L. ethyl acetate:hexane, 1:1; 1L. ethyl acetate: hexane, 3:1; 500 ml 1% methanol/ethyl acetate. The pureractions were concentrated to afford 1.24 g of an off white solid. The solid was recrystallized from ethyl ether to afford 935 mg of 71% of the title B compound as a white crystaline powder, m.p. 147°-149° C.

(C)

[3R-[1(S*),3α,4α]]-1-(3-pyrrolidinyl)-3-hydroxy-1,3,4,5-tetrahydro-4-(4-methoxyphenyl)-6-(trifluoromethyl)-2H-1-benzazepin-2-one A mixture of the title B compound (865 mg, 1.7 mmol), ammonium formate (552 mg, 8.76 mmol), and 10% palladium on carbon (150 mg) was refluxed in 25 ml MeOH:AcOH, 4:1 for 4 hours. At this time, additional ammonium formate (220 mg, 3.5 mmol) and 10% palladium on carbon (120 mg) were added. This mixture was refluxed for 30 minutes and the catalyst was then removed by filtration through celite. The filter cake was washed well with methanol and the filtrate was concentrated in vacuo. The residue was partitioned between $Na_2CO_3$ solution and ethyl acetate. The organic layer was washed with brine, dried over sodium sulfate and concentrated. The residue was flash chromatographed on a 5×20 cm SiO₂ column that was pretreated with $CH_2Cl_2$:MeOH:$Et_3N$, 94:5:1. The column was eluted first with 2 L. 5% MeOH:$CH_2Cl_2$ and 2 L 70% MeOH:$CH_2Cl_2$. The pure fractions were concentrated to afford 60 mg (84%) yield of the title C compound as a colorless foam.

D)

[3R-[1(S*),3α,4α]]-1,3,4,5-Tetrahydro-3-hydroxy-4-(4-methoxyphenyl)-1-(3-pyrrolidinyl)-6-(trifluoromethyl)-2H-1-benzazepin-2-one, fumarate (1:1) salt The title C compound (600 mg, 1.43 mmol) was dissolved in 5 ml of methanol and fumaric acid (166 mg, 1.43 mmol) was added as a solution in hot methanol. The solution was concentrated to dryness and the solid residue was crystallized from methanol/ethyl ether to afford 650 mg (86%) of the title compound as a colorless crystalline solid, m.p. 228°-231° C., $[\alpha]_D +57.8°$ (c=1.0 HOAc).

Analysis calc'd for $C_{22}H_{23}F_3N_2O_3 \cdot C_4H_4O_4$: C, 58.20; H, 5.07; N, 5.22; F, 10.62;

Found: C, 58.09; H, 4.81; N, 5.27; F, 10.45.

EXAMPLE 34

[3R-[1(R*),3α,4α]]-1,3,4,5-Tetrahydro-3-hydroxy-4-(4-methoxyphenyl)-1-(3-pyrrolidinyl)-6-(trifluoromethyl)-2H-1-benzazepin-2-one, fumarate (1:1) salt A) 3S-1-Benzyl-3-(benzoyloxy)-pyrrolidine Diethyl azodicarboxylate (4.8 ml; 30 mmol) was added dropwise to a stirred solution of 3(R)-1-benzyl-3-hydroxypyrrolidine (3.5 g, 20 mmol), triphenyl phosphine (7.86 g, 30 mmol), and benzoic acid (6.12 g, 50 mmol) in 200 ml of tetrahydrofuran at room temperature. After stirring for 1.5 hours, the tetrahydrofuran was removed in vacuo and the residue was partitioned between 1N hydrochloric acid and ethyl acetate. The ethyl acetate layer was extracted again with 1N hydrochloric acid and the combined acid layers were basified with solid sodium carbonate. The resulting basic layer was extracted with ethyl acetate. The ethyl acetate layer was washed with water, followed by brine and then dried over sodium sulfate. The organic layer was concentrated and the residue was flash chromatographed on a 5×30 cm SiO₂ column using ethyl acetate/hexane, 1:3 as the mobile phase. The pure fractions were concentrated to afford 3.30 g (59%) yield of the title A compound as a colorless oil.

B) 3S-1-Benzyl-3-hydroxypyrrolidine

1N Sodium hydroxide (25 ml, 25 mmol) was added to a solution of the title A compound (3.15 g, 11.2 mmol) in 100 ml of methanol. The reaction became cloudy immediately and cleared after 30 minutes. After stirring an additional 30 minutes, the methanol was removed in vacuo and the aqueous mixture that remained was extracted with ethyl acetate. The organic phase was washed with water, followed by brine. After drying over sodium sulfate, the ethyl acetate was removed in vacuo to afford 1.5 g (77%) yield of the title B compound as a colorless oil.

(C) 3S-1-Benzyl-3-(p-toluenesulfonyloxy)pyrrolidine

A mixture of the title B compound (1.45 g, 8.2 mmol) and p-toluene sulfonyl chloride (2.35 g, 12.3 mmol) was stirred in 16 ml of pyridine for 20 hours at room temperature. After this time the reaction mixture was partitioned between ethyl ether and sodium carbonate solution. The organic layer was washed with sodium carbonate solution, water and brine. After drying over sodium sulfate, the organic layer was concentrated first on low vacuum and finally on high vacuum to remove traces of pyridine. The residue was flash chromatographed on a 5×25 cm $SiO_2$ column using ethyl acetate/hexane, 1:3 as the eluant, the pure fractions were concentrated to afford 2.31 g (85%) yield of the title C compound as a light yellow oil.

(D) [3R-[1(R*),3α,4α]]-1-(Benzyl-3-pyrrolidinyl)-3-hydroxy-1,3,4,5-tetrahydro-4-(4-methoxyphenyl)-6-trifluoromethyl)-2H-1-benzazepin-2-one A mixture of the title C compound (2.2 g, 6.64 mmol), (3R-cis)-3-hydroxy-4-(4-methoxyphenyl)-6-(trifluoromethyl)-2H-1-benzazepin-2-one (1.86 g, 5.31 mmol) and cesium carbonate (8.65 g, 26.5 mmol) was refluxed in 75 ml of methyl ethyl ketone for 18 hours. The reaction was cooled, diluted with 150 ml of ethyl ether, and filtered through celite.

The filtrate was concentrated and the residue was flash chromatographed on a 5×25 cm $SiO_2$ column using ethyl acetate/hexane, 3:1 as the eluant. The column only afforded partial purification so the concentrated fractions (2.35 g, 88% crude) were rechromatographed on a 5×25 cm $SiO_2$ column using 2.5% MeOH:$CH_2Cl_2$ as the eluant. The pure fractions were concentrated to afford 1.64 g (61%) yield of the title D compound as a white foam.

(E) [3R-[1(R*),3α,4α]]-1,3,4,5-Tetrahydro-3-hydroxy-4-(4-methoxyphenyl)-1-(3-pyrrolidinyl)-6-(trifluoromethyl)-2H-1-benzazepin-2-one, fumarate (1:1) salt A solution of the title D compound (1.58 g, 3.1 mmol) in 30 ml of glacial acetic acid was hydrogenated over 20% Pd(OH)$_2$/C for 3 hours at room temperature, using a balloon apparatus. After this time, the catalyst was filtered off and the filter cake was washed with 15 ml of glacial acetic acid. The filtrate was diluted with 150 ml of water and the acidic mixture was basified with solid sodium carbonate. The now basic mixture was extracted with ethyl acetate (150 ml). The organic layer was washed with brine and dried over magnesium sulfate. After concentrating the filtrate, the residue was flash chromatographed on a 5×25 cm $SiO_2$ column which was packed in 94:5:1, $CH_2Cl_2$:MeOH:$Et_3N$. The column was eluted as follows: 2L 5% MeOH/$CH_2Cl_2$, and 1 L. 10% MeOH/$CH_2Cl_2$. The pure fractions were concentrated to a semisolid residue which was dissolved in 5% MeOH/$CH_2Cl_2$ and filtered through celite. The filtrate was concentrated to afford 1.173 g (90%) yield of the free base as a white foam.

Free base (1.08 g, 2.57 mmol) was dissolved in methanol an fumaric acid (298 mg, 2.57 mmol) was added as a solution in hot methanol. The resulting solution was concentrated to a white foam which was crystallized from hot isopropanol. Filtration and vacuum drying afforded 925 mg (68%) yield of the title compound as a white crystalline solid, m.p. 214°–216° C; $[\alpha]_D +58.9°$ (c=0.50, MeOH).

Analysis calc'd for $C_{22}H_{23}N_2F_3O_3 \cdot C_4H_4O_4 = 0.1$ $C_3H_8O$ (isopropanol):
C, 58.22; H, 5.17; N, 5.16; F, 10.51;
Found: C, 58.07; H, 5.11; N, 5.26; F, 10.44.

EXAMPLE 35

(This Example 35 is for the title compound of Example 16, but provides an alternate procedure to prepare the title A compound in Example 16.)

[3R-[1(S*),3α,4α]]-1,3,4,5-Tetrahydro-3-hydroxy-4-(4-methoxyphenyl)-1-(2-pyrrolidinylmethyl)-6-(trifluoromethyl)-2H-1-benzazepin-2-one, monohydrochloride

A. S-1-(benzyloxycarbonyl)-2-[(4-methylphenylsulfonyloxy)-methyl]-pyrrolidine To S-1-(benzyloxycarbonyl)-2-pyrrolidinemethanol (105.7 g., 449 mmol) in pyridine (400 ml) at 0° C. was added slowly p-toluenesulfonyl chloride (102.8 g, 539 mmol). The reaction mixture was allowed to warm to room temperature and stirred for a total of 20 hours. Half of the pyridine was removed under reduced pressure before it was diluted with water and extracted with ether (×3). The combined extract was washed with a dilute aqueous HCl - aqueous CuSO$_4$ solution (×3), dried (MgSO$_4$), filtered and concentrated to a crude viscous liquid which was extracted with warm hexane (×3). The dark orange viscous liquid (147.7 g, 84%) slowly solidified at 5° C. to give the title A compound as a pale purple solid.

B. [3R-[1(S*),3α,4α]]-1-[(1-Benzyloxycarbonyl-2-pyrrolidinyl)methyl]-3-hydroxy-1,3,4,5-tetrahydro-4-(4-methoxyphenyl)-6-(trifluoromethyl)-2H-1-benzazepin-2-one (3R-cis)-1,3,4,5-Tetrahydro-3-hydroxy-4-(4-methoxyphenyl)-6-(trifluoromethyl)-2H-1-benzazepin-2-one (25 g, 71.2 mmol), cesium carbonate (34.8 g, 106.7 mmol) and the title A compound (34.6 g, 89.0 mmol) in DMF (200 ml) were heated to 50° C. After 8 hours, additional title A compound (2.8 g, 7.2 mmol) was added and stirring was continued for another 12 hours. The reaction mixture was cooled to room temperature, diluted with water and extracted with EtOAc (×3). The combined extract was washed with 10% aqueous LiCl (×3), dried (MgSO$_4$), filtered and concentrated. The pale yellow solid was triturated with ether (100 ml) for 30 minutes before hexane (100 ml) was added and stirred for an additional 30 minutes. Filtration yielded the title B compound as a pale yellow powder (34.5 g).

C.
[3R-[1(S*),3α,4α]]-1,3,4,5-Tetrahydro-3-hydroxy-4-(4-methoxyphenyl)-1-(2-pyrrolidinylmethyl)-6-(trifluoromethyl)-2H-1-benzazepin-2-one, monohydrochloride The title B compound (35 g, 61.6 mmol), palladium hydroxide on carbon (7 g) and acetyl chloride (35 ml) in absolute ethanol (700 ml) was placed in the Parr shaker apparatus and shaken for 1 hour 40 minutes at a pressure of 50 lb of $H_2$. After evacuation of all $H_2$, anhydrous $MgSO_4$ was added and the reaction mixture was suction filtered to remove the catalyst. The solids were washed well with absolute ethanol. The filtrate was concentrated and the residue was diluted with 30 saturated aqueous $KHCO_3$ and extracted with EtOAc (×3). The combined extract was dried ($MgSO_4$), filtered and concentrated to yield a pale yellow foam which was dissolved in MeOH (350 ml) and filtered. Fumaric acid (7.15 g, 61.6 mmol) was added and heated on a steam bath to form a homogeneous solution. The solution was allowed to cool and crystallize overnight.

The white crystalline solid was filtered and washed well with EtOAc to obtain the fumarate salt of the title compound (29.76 g, 88%). The fumarate salt was converted to the free base by washing with saturated aqueous $KHCO_3$ and extracting with ether/EtOAc (×3). To the free base dissolved in ether was added excess ethereal HCl. The white precipitate was collected and dried to obtain the title compound (21.6 g, 100% from the fumarate), m.p. 165°-167° C., $[\alpha]_D = +75.3°$ (c=1, MeOH).

Analysis calc'd for $C_{23}H_{25}F_3N_2O_3 \cdot HCl \cdot 0.73 H_2O$: C, 57.07; H, 5.72; N, 5.7g; Cl, 7.32; F, 11.78
Found: C, 57.31, H, 5.56; N, 5.55; Cl, 7.42; F, 12.03

EXAMPLE 36
[3R-[1(S*),3α,4α]]-3-(Acetyloxy)-1,3,4,5-tetrahydro-7-methoxymethoxy-4-(4-methoxyphenyl)-1-(2-pyrrolidinyl methyl)-2H-1-benzazepin-2-one, fumarate (1:1) salt

A.
[3R-[1S*,3α,4α]]-1-[(N-Benzyloxycarbonyl-2-pyrrolidinyl)methyl]-3-hydroxy-1,3,4,5-tetrahydro-4-(4-methoxyphenyl)-7-(methoxymethoxy)-2H-1-benazepin-2-one A suspension of cis-3-hydroxy-7-methoxymethoxy-4-(4-methoxyphenyl)-2H-1-benzazepin-2-one (1.5 g, 4.37 mmol), anhydrous cesium carbonate (2.84 g, 8.75 mmol) and the title A compound from Example 35 (2.55 g, 6.56 mmol) in DMF (50 ml) was heated to 58° C. for 28 hours. The reaction mixture was cooled, diluted with water and extracted with EtOAc (×3). The organic extracts were combined, washed with a 10% aqueous lithium chloride solution, dried ($MgSO_4$), filtered and concentrated to obtain the crude product. A series of silica gel columns were run to isolate the desire (+) isomer, title A compound. The first column was eluted with 20% EtOAc-$CH_2Cl_2$ to isolate the pure (±) diastereomers. The second column was eluted with 1-10% ether in $CH_2Cl_2$ to give the fast moving isomer of the title A compound (0.44 g, $R_f$=0.64 (50% ether in $CH_2Cl_2$), $[\alpha]_D = +161.31°$ (c=1.0, MeOH)), the slow moving isomer (0.08 g, $R_f$0.55 (50% ether in $CH_2Cl_2$), $[\alpha]_D = 81.81°$ (c=1.0, MeOH)) and some mixed fractions (0.57 g). The final chromatography of the mixed fractions was eluted with 4-10% ether in $CH_2Cl_2$ to give an additional amount of the fast moving isomer (0.33 g). Total yield of the fast moving isomer was 0.77 g.

B.
[3R-[1S*,3α,4α]]-1-[(1-Benzyloxycarbonyl-2-pyrrolidinyl)methyl]-3-(acetyloxy)-1,3,4,5-tetrahyo-4-(4-methoxyphenyl)-7-(methoxymethoxy)-2H-1-benazepin-2-one The title A compound (0.70 g, 1.25 mmol), 4-dimethylaminopyridine (0.31 g, 2.5 mmol) and acetic anhydride (0.64 g, 6.24 mmol) were stirred at room temperature under argon for 14 hours. The reaction solution was absorbed onto silica gel (60-200 mesh) and chromatographed onto a silica gel (60-200 mesh) and chromatographed on a silica gel column. Elution with 20-40% EtOAc in hexane afforded the title B compound (0.74 g) as a white foam.

C.
[3R-[1(S*),3α,4α]]-3-(Acetyloxy)-1,3,4,5-tetrahydro-7-methoxymethoxy-4-(4-methoxyphenyl)-1-(2-pyrrolidinylmethyl)-2H-1-benzazepin-2-one, fumarate (1:1) salt To a solution of the title B compound (0.64 g, 1.06 mmol) in EtOAc (10 ml) and trifluoroacetic acid (0.4 ml) was added with stirring palladium hydroxide on carbon (130 mg). The reaction flask was equipped with a hydrogen filled balloon. The reaction flask was evacuated under reduced pressure and filled with hydrogen. The mixture was then stirred vigorously at room temperature for 6 hours before the $H_2$ was removed and anhydrous $MgSO_4$ was added. The solids were removed by suction filtration and washed well with EtOAc. The filtrate was concentrated at reduced pressure and the residue was dissolved in EtOAc. The organic layer was washed with aqueous $KHCO_3$ and partitioned. The aqueous layer was extracted with EtOAc (×2) and the combined organic layers were dried ($MgSO_4$), filtered and concentrated to give the free amine as a pale orange foam (0.32 g). The free amine was dissolved in methanol (20 ml) and fumaric acid (79.3 mg, 0.68 mmol) was added and stirred until the solution was homogeneous. Concentration yielded the title compound (0.41 g) as a pale yellow foam, m.p. 126°-130° C., $[\alpha]_D = +89.7°$ (c=1, MeOH).

Analysis calc'd for $C_{26}H_{32}N_2O_6 \cdot C_4H_4O_4 \cdot 0.6 H_2O$: C, 60,50; H, 6.30; N, 4.71;
Found: C, 60.44; H, 6.00; N, 4.74.

EXAMPLE 37
[3R-[1(2S*,4R*),3α,4α]]-1,3,4,5-Tetrahydro-3-hydroxy-4-(4-methoxyphenyl)-1-[[4-(phenylmethoxy)-2-pyrrolidinyl]methyl]-6-(trifluoromethyl)-2H-1-benzazepin-2-one, monohydrochloride

A.
(2S,4R)-4-hydroxy-1-(t-butoxycarbonyl)-2-pyrrolidinecarboxylic acid

A suspension of 20.0 g (0.152 mole) of trans-4-hydroxy-L-proline and 38.0 g (0.174 mole) of di-tertiary butyl dicarbonate in 250 ml of dioxane was treated gradually with 350 ml of 1N NaOH, then stirred at room temperature for 24 hours. The mixture was concentrated in vacuo to approximately 200 ml, then diluted with 750 ml of $H_2O$. After washing with EtOAc, the aqueous solution was acidified with 6N HCl and saturated with NaCl before extraction with EtOAc (×2X). The organic solution was washed with $H_2O$ and brine, dried and evaporated to give 30.9 g of the title A compound as a tan solid, m.p. 104°-106°.

Analysis calc'd for $C_{10}H_{17}NO_5$:
C, 51.94; H, 7.40; N, 6.05;
Found: C, 51.31; H, 7.65; N, 5.67.

B.
(2S,4R)-4-(phenylmethoxy)-1-(t-butoxycarbonyl)-2-pyrrolidinecarboxylic acid A solution of 7.04 g (0.030 mole) of the title A compound and 5.2 g (0.030 mole) of benzyl bromide (benzyl chloride works equally well) in 70 ml of DMF (-78° bath) was treated with 0.38 g (0.009 mole) of 60×NaH and stirred at room temperature for 3 hours, then poured over ice. The solution was washed with EtOAc and acidified to pH 2 using 6N HCl saturated with NaCl. Extraction with EtOAc (×2X) gave 7.16 g of an oil. Flash chromatography using EtOAc gave 4.44 g of the title B compound.

Analysis calc'd for $C_{17}H_{23}NO_5$:
C, 63.53; H, 7.21; N, 4.35.
Found: C, 63.08; H, 7.38; N, 4.06.

C.
(2S,4R)-4-(phenylmethoxy)-1-(t-butoxycarbonyl)-2-pyrrolidinemethanol

A solution of 4.40 g (0.013 mole) of the title B compound and 1.47 g (0.013 mole) of ethyl chloroformate in 65 ml of THF (151) was treated dropwise with a solution of 1.40 g (0.013 mole) of $Et_3N$ in 10 ml of THF. After stirring for one hour at room temperature, the mixture was filtered directly into a 3 neck flask. The stirred solution was treated dropwise with a solution of 0.75 g (0.020 mole) of $NaBH_4$ in 8 ml of $H_2O$. After one hour, the solvent was evaporated and the residue, 5 in EtOAc, was washed with 1N HCl, $H_2O$, 1N NaOH, $H_2O$ and brine. The dried solution was evaporated to afford 3.23 g of an oil. Flash chromatography using EtOAc/hexane 1:2 gave 2.76 g of the title C compound, $[\alpha]_D = -28.3°$, (c=1.86, $CHCl_3$).

D.
(2S,4R)-4=(phenylmethoxy)-1-(t-butoxycarbonyl)-2-(bromomethyl)pyrrolidine A solution of 2.7 g (0.0087 mole) of the title C compound, 5.8 g (0.0174 mole) of $CBr_4$ and 4.5 g (0.0174 mole) of triphenylphosphine in 150 ml of ether was stirred overnight at room temperature. The ether was decanted, and the residual solids were washed with hot hexane (×2X). The hexane extracts were combined with the ether solution and the solvents were evaporated to leave a semi solid material which was extracted with boiling hexane (×2X). The oil residue after hexane evaporation was dissolved in EtOAc and treated with Baker silica gel (60-200 mesh). The solvent was evaporated and the powder was placed over a column of the same $SiO_2$ and eluted with hexane to remove excess $CBr_4$. Elution with EtOAc/hexane 1:2 gave 2.3 g of desired the title D compound, $[\alpha]_D = -37.9°$, (c=2.59, $CHCl_3$).

E.
[3R-[1(2S*,4R*)3α,4α]]-1-[[1-(t-butoxycarbonyl)-4-(phenylmethoxy)-2-pyrrolidinyl]-methyl]-3-hydroxy-1,3,4,5-tetrahydro-4-(4-methoxyphenyl)-6-(trifluoromethyl)-2H-1-benzazepin-2-one A stirred solution of 0.93 g (0.0026 mole) of (3R-cis)-3-hydroxy-4-(4-methoxyphenyl)-6-(trifluoromethyl)-2H-1-benzazepin-2-one in 10 ml of DMF was treated with 0.13 g (0.0033 mole) of KH (0.39 ml of 35% oil suspension). After one hour, a solution of 1.23 g (0.0033 mole) of the title D compound in 2 ml of DMF was added gradually to the reaction mixture, then heated (60° oil bath) for 18 hours. The cooled mixture was diluted with EtOAc, washed with $H_2O$ (×2X) and brine. The dried solvent was evaporated to give 2.2 g of semi-solid material. This crude product was dissolved in 5 ml of toluene, chilled for 1 hour, then filtered to give 0.28 g of starting material. Flash chromatography of the remaining solution over 400 ml of $SiO_2$ using EtOAc/hexane 1:1.5 gave 0.57 g of the title E compound as a glass-like solid, $[\alpha]_D = +116.9°$, (c=1.95, $CHCl_3$).

F.
[3R-[1(2S*,4R*),3α,4α]]-1,3,4,5-Tetrahydro-3-hydroxy-4-(4-methoxyphenyl)-1-[[4-(phenylmethoxy)-2-pyrrolidinyl]methyl]-6-(trifluoromethyl)-2H-1-benzazepin-2-one, monohydrochloride The title E compound (0.95 g, 0.00148 mole) was dissolved in 8 ml of $CH_2Cl_2$ containing 0.84 g (0.0074 mole) of trifluoroacetic acid. The solution was stirred overnight at room temperature. The solvent was evaporated. The residue was dissolved in toluene and the solvent was evaporated in vacuo to remove excess acid. The residue, in EtOAc, was washed with 1N NaOH, $H_2O$ and brine. The solution was dried and evaporated to afford 0.51 g of the title compound as an oil, $[\alpha]_D = +137.0°$, (c=1.0, $CHCl_3$).

Analysis calc'd for $C_{30}H_{31}N_2F_3O_4$:
C, 66.65; H, 5.77; N, 5.18.
Found: C, 65.13; H, 5.69; N, 5.04.

The above was dissolved in 15 ml of ether and treated with one equivalent of ethereal HCl to form 0.42 g of colorless product, m.p. 184°-186°, $[\alpha]_D = +50.4°$ C., (c=1.15, MeOH).

Analysis calc'd for $C_{30}H_{31}F_3N_2O_4 \cdot HCl$:
C, 60.55; H, 5.93; N, 4.70; Cl, 5.95;
Found: C, 60.79; H, 5.59; N, 4.43; Cl, 6.04.

EXAMPLE 38
[3R-[1(2S*,4R*),3α,4α]]-1,3,4,5-Tetrahydro-3-hydroxy-1-[(4-hydroxy-2-pyrrolidinyl)methyl]-4-(4-methoxyphenyl)-6-(trifluoromethyl)-2H-1-benzazepin-2-one, monohydrochloride A suspension of 1.9 g (0.0035 mole) of the title compound of Example 37 in 25 ml of HOAc was treated with 0.5 g of 10% Pd/C and hydrogenated at atmospheric pressure for 24 hours. TLC (20% MeOH/EtOAc) indicated reaction to be about 60% complete. An additional 0.2 g of catalyst was added and the reaction was allowed to proceed for 48 hours. The catalyst was filtered and washed with EtOH. The solution was evaporated in vacuo (40°) and the residue, in EtOAc, was washed with saturated $NaHCO_3$. This resulted in the formation of the solid product, insoluble in either layer. This material, 1.3. g was dissolved in 7 ml of hot EtOH, then filtered through hyflo (#50 paper). The solvent was evaporated and the residue was treated with $CH_3CN$ to form 0.77 g of a colorless solid, m.p. 212°-214°, $[\alpha]_D = +74.1°$, (c=0.72, MeOH).

The above product was dissolved in 3 ml of MeOH and treated with 1 eq. of ethereal HCl. The solvent was evaporated and the residue was treated with $CH_3CN$ to form 0.61 g of colorless solid, m.p. 214°-216°. Analytically pure material was obtained by solution in hot MeOH and gradual addition of CH₃CN as the MeOH was removed by boiling. The cloudy suspension was cooled and filtered to give 0.45 g of colorless title compound, m.p. 217°–218°, $[\alpha]_D = +75.2°$, (c=1.0, MeOH).

Analysis calc'd for $C_{23}H_{25}F_3N_2O_4 \cdot HCl \cdot 0.75\ H_O$:
C, 55.21; H, 5.54; N, 5.60; Cl, 7.09;
F, 11.39;
Found: C, 55.24; H, 5.50; N, 5.62; Cl, 7.29;
F, 11.37.

EXAMPLE 39

[3R-[1(2S*,4S*),3α, 4α]]-1,3,4,5-Tetrahydro-3-hydroxy-4-(4-methoxyphenyl)-1-[[4-(phenylmethoxy)-2-pyrrolidinyl]methyl]-6-(trifluoromethyl)-2H-1-benzazepin-2-one, monohydrochloride

A.
(2S,4S)-4-hydroxy-1-(t-butoxycarbonyl)-2-pyrrolidinecarboxylic acid

A solution of N-Boc-4-trans hydroxy-L-proline (11.55 g, 0.05 mole) and triphenyl phosphine (14.4 g, 0.055 mole) in 450 ml of dry THF under argon at 20° was treated dropwise with a solution of diisopropyl azodicarboxylate (10.9 ml, 11.1 g, 0.055 mole) in 50 ml of THF over 30 minutes, then allowed to stir an additional 2 hours. The reaction mixture was concentrated in vacuo to 100 ml, then treated with 100 ml of 1N NaOH. After stirring for 15 minutes, THF was removed and the residual aqueous solution washed with EtOAc (discard). The aqueous layer was acidified to pH 1.5 with 6N HCl, saturated with NaCl and extracted with EtOAc (×2). The organic fractions were washed with brine, dried (MgSO₄) and concentrated in vacuo to give 13g of a viscous oil. Trituration with hot IPE and cooling afforded 10.2 g of the title A compound, m.p. 147°–148.5°, $[\alpha]_D = -47.1°$, (c=0.92, EtOH).

B.
(2S,4S)-4-(phenylmethoxy)-1-(t-butoxycarbonyl)-2-pyrrolidinecarboxylic acid A solution of the title A compound (10.1 g, 0.0438 mole) and benzyl chloride (5.55 g, 0.0438 mole) in 60 ml of dry DMF under argon was cooled to −78° and treated at once with sodium hydride (3.50 g, 0.087 mole, 60% in MO). The cooling bath was removed and the reaction mixture allowed to warm to room temperature and stir overnight. The mixture was poured onto ice and washed with EtOAc (×2). The basic aqueous solution was acidified to pH 2.0 with 6N HCl, saturated with NaCl and extracted with EtOAc (×2). The organic fractions were washed with brine, combined and dried (MgSO₄) and concentrated in vacuo to give 18.6 g of an oil. Flash chromatography on 1700 ml LPS-1 SiO₂ and elution with EtOAc/HOAc (200:1) gave 9.35 g of the title B compound as a crude solid. Crystallization from IPE afforded 7.75 g of the title B compound, m.p. 110°–111°, $[\alpha]_D = -28.8°$, (c=0.96, EtOH).

C.
(2S,4S)-4-(phenylmethoxy)-1-(t-butoxycarbonyl)-2-pyrrolidinemethanol

A solution of the title B compound (7.75 g, 0.024 mole) and ethyl chloroformate in 150 ml of dry THF under argon at 15°–20° was treated dropwise with a solution of triethylamine (2.44 g, 0.024 mole) in 10 ml of THF over 10°–15 minutes. After stirring for 2 hours, solids were filtered and washed with fresh THF. The combined filtrate and washings was cooled in a water bath at 15° and treated dropwise with a solution of NaBH₄ (1.36 g, 0.036 mole) in 10 ml of H₂O. After stirring at room temperature for 4 hours, volatiles were removed in vacuo and the residue, dissolved in EtOAc, was washed with 1N HCl, H₂O, 1N NaOH, H₂O and brine. The dried (MgSO<) organic fraction was concentrated in vacuo to give 7.2 g of crude product. Flash chromatography on 1 1 of LPS-1 SiO₂, eluting with 4:1 of EtOAc/Hexane (3:7) and 2 1 of EtOAc/Hexane (1:1) gave 6.15 g of the title C compound as an oil, $[\alpha]_D = -18.5°$, (c=1.5, CHCl₃).

D.
(2S,4S)-4-(phenylmethoxy)-1-(t-butoxycarbonyl)-2-4-methylphenylsulfonyloxy)methyl]pyrrolidine A solution of the title C compound (3.0 g, 9.6 mmol) in 15 ml of dry pyridine was treated with toluene sulfonyl chloride (2.05 g, 10.7 mmol) and stirred under argon at room temperature overnight. The reaction mixture was diluted with EtOAc and washed with 1N HCl until the aqueous wash remained acidic (3 to 4 times), then with H_O, NaHCO₃ and brine. The dried (MgSO₄) organic fraction was concentrated in vacuo to give 4.55 g of an oil. Flash chromatography on 800 ml of LPS-1 SiO₂ and elution with EtOAc/Hexane (1:4) gave 3.9 g of the title D compound, $[\alpha]_D = -8.01°$, (c=1.76, CHCl₃).

E.
[3R-[1(2S*,4S*)3a,4a]]-1-[[1-(t-butoxycarbonyl)-4-(phenylmethoxy)-2-pyrrolidinyl]-methyl]-3-hydroxy-1,3,4,5-tetrahydro-4-(4 methoxyphenyl)-6-(trifluoromethyl)-2H-1benzazepin-2-one A solution of (3R-cis)-3-hydroxy-4-(4-methoxyphenyl)-6-(trifluoromethyl)-2H-1-benzazepin-2-one (2.35 g, 6.7 mmol) and the title D compound (3.50 g, 7.6 mmol) in 25 ml of dry DMF under argon was treated with cesium carbonate (3.26 g, 10.05 mmol), then heated at 50° overnight. Starting benzazepine remained, though tosylate was consumed. An additional 0.4 g (0.8 mmol) of tosylate was added and the mixture was stirred at 60° for two more days. The reaction mixture, diluted with EtOAc, was washed with H₂O and brine, dried (MgSO₄) and concentrated in vacuo to give 4.87 g of an oil. Flash chromatography on 1000 ml of LPS-1 SiO₂ and elution with toluene/EtOAc (5:1) gave 3.36 g of the title E compound, $[\alpha]_D = +113.2°$, (c=0.84, CHCl₃).

F.
[3R-[1(2S*,4S*),3α,4α]]-1,3,4,5-Tetrahydro-3-hydroxy-4-(4-methoxyphenyl)-1-[[4-(phenylmethoxy)-2-pyrrolidinyl]methyl]-6-(trifluoromethyl)-2H-1-benzazepin-2-one, monohydrochloride A solution of the title E compound (3.1 g, 4.84 mmol) in 10 ml of CH₂Cl₂ under argon at room temperature was treated with TFA (7.5 ml, 0.1 mole) and heated at gentle reflux temperature for 1 hour. Volatiles were stripped in vacuo and the residue, dissolved in EtOAc, was washed with NaHCO₃, water and brine. The dried (MgSO₄) organic fraction was concentrated in vacuo to give 2.5 g of an oil. Flash chromatography on 800 ml LPS-1 SiO₂ and elution with EtOAc/MeOH (93:7) gave 2.08 g of the title compound as an oil, $[\alpha]_D = +141.1°$, (c=0.88, CHCl₃).

The above free base (700 mg, 1.3 mmol) in 15 ml of CH$_3$CN was treated with excess ethereal HCl. Volatiles were stripped in vacuo and the residue triturated with IPE to give 730 mg of the salt as an off white powder, m.p. 120°–140° (foam), $[\alpha]_D = +78.6°$, (c=0.90, MeOH).

Analysis calc'd for C$_{30}$H$_{31}$F$_3$N$_2$O$_4$.HCl.0.2 H$_2$O:
C, 62.03; H, 5.63; N, 4.82; F, 9.81;
Cl, 6.10;
Found: C, 61.93; H, 5.77; N, 4.92; F, 9.79;
Cl, 6.01.

EXAMPLE 40

[3R-[1(2S*,4S*),3α,4α]]-1,3,4,5-Tetrahydro-3-hydroxy-1-[(4-hydroxy-2-pyrrolidinyl)methyl]-4-(4-methoxyphenyl)-6-(trifluoromethyl)-2H-1-benzazepin-2-one, monohydrochloride A solution of the title compound from Example 39 (1.25 g, 2.31 mmol) in 15 ml of methanol containing 400 mg of 10% Pd/C was treated with ammonium formate (730 mg, 11.6 mmol) and the mixture heated at reflux temperature overnight. TLC analysis showed the reaction to be incomplete. Additional 10% Pd/C (200 mg) and ammonium formate (300 mg) were added and heating continued overnight. Catalyst was removed by filtration through celite and the solvent stripped in vacuo. The residue, dissolved in EtOAc, was washed with 1N NaOH, water and brine. The dried (MgSO$_4$) organic solution was concentrated in vacuo to give 0.75 g of an oil. Flash chromatography on 200 ml of LPS-1 SiO$_2$ (pretreated with CH$_2$Cl$_2$/Et$_3$N - 100:1) and elution with CH$_2$Cl$_2$/MeOH (95:5) gave 0.50 g of the title compound as a foam, m.p. 75°–90°, $[\alpha]_D = +148.9°$, (c=0.85, CHCl$_3$).

The above free base (0.48 g, 1.06 mmol) in 10 ml CH$_3$CN was treated with excess ethereal HCl, causing precipitation of the salt. The salt was collected, washed with CH$_3$CN and ether and dried in vacuo over P$_2$O$_3$ at 100° to give 436 mg, m.p. 252°–255°, $[\alpha]_D = +84.8°$, (c=0.56, MeOH).

Analysis calc'd for C$_{23}$H$_{25}$F$_3$N$_2$O$_4$.0.5 H$_2$O:
C, 56.73; H, 5.38; N, 5.75; Cl, 7.28;
F, 11.71;
Found: C, 56.55; H, 5.26; N, 5.70; Cl, 7.48;
F, 11.74.

EXAMPLE 41

[3R-[1(3S*,5S*),3α,4α]]-1,3,4,5-Tetrahydro-3-hydroxy-1-[5-(hydroxymethyl)-3-pyrrolidinyl]-4-(4-methoxyphenyl)-6-(trifluoromethyl)-2H-1-benzazepin-2-one, fumarate (1:1) salt

A. (2S,4R)-4-hydroxy-2-pyrrolidinecarboxylic acid methyl ester

Acetyl chloride (7.6 ml; 107 mmol) was added slowly to MeOH (70 ml). The reaction was exothermic. (2S,4R)-4-Hydroxy-2-pyrrolidinecarboxylic acid (10 g; 76.2 mmol) was added and the mixture was refluxed for 4 hours. At this time, another portion of 3 ml of acetyl chloride in 30 ml of MeOH was added. The mixture was refluxed an additional 3 hours. The reaction was cooled to room temperature and ~750 ml of Et$_2$O was added. The resulting colorless crystals were filtered and dried to afford 11.89 g of the title A compound.

B. (2S,4R)-4-hydroxy-1-(phenylmethyl)-2-pyrrolidinecarboxylic acid methyl ester A mixture of the title A compound (11.85 g; 65.2 mmol), Et$_3$N (18.55 ml; 130.04 mmol), and benzyl chloride (15 ml; 130.04 mmol) was refluxed in 60 ml of CH$_2$Cl$_2$ for 7 hours. The resulting suspension was partitioned between CHCl$_3$ and 1N NaOH. The organic layer was washed with 1N NaOH, followed by brine. The organic layer was then dried (Na$_2$SO$_4$) and concentrated. The crude residue was flash chromatographed on a (12×35 cm) SiO$_2$ column with the following elution scheme: 1) 2 L CH$_2$Cl$_2$; 2) 4 L 3% MeOH/CH$_2$Cl$_2$, and 4 L 5% MeOH CH$_2$Cl$_2$. The pure fractions were concentrated to afford 15.3 g of the title B compound as a colorless oil.

C. (2S,4R)-4-hydroxy-1-(phenylmethyl)-2-pyrrolidinemethanol

A suspension of lithium aluminum hydride (5 g; 126 mmol) in 250 ml of Et$_2$O was cooled to 0° C. The title B compound (9.88 g; 42 mmol) was added dropwise as a solution in 150 ml of Et$_2$O. After stirring 1 hour at 0° C., the reaction was carefully quenched by adding 5 ml of H$_2$O, 5 ml of 15% NaOH, and 15 ml H$_2$O. After stirring for 1 hour at room temperature, the suspension was filtered through celite and the filter cake was washed thoroughly with Et$_3$O. The filtrate was concentrated and co-evaporated from toluene (2×100 ml), to afford 7.97 g, of the title C compound as a colorless oil.

D. (2S,4R)-4-hydroxy-1-(phenylmethyl)-2-(t-butyldiphenylsilyloxymethyl) pyrrolidine t-Butylchlorodiphenysilane (11.05 ml; 42.5 mmol) was added dropwise to a solution of the title C compound (7.97 g; 38.5 mmol) in 20 ml pyridine at 0° C. After stirring for 1 hour at 0° C., the reaction mixture was partitioned between Et$_2$O and H$_2$O. The organic layer was washed with H$_2$O (2×50 ml), dried (MgSO$_4$), and concentrated. The crude residue was flash chromatographed on a (2.5×40 cm) SiO$_2$ column which was eluted first with CH$_2$Cl$_2$ (2 L) and then with 5% MeOH/CH$_2$Cl$_2$ (2 L). The pure fractions were combined and the mixed fractions were rechromatographed on a 5×25 cm SiO$_2$ column which was eluted with 2% MeOH/CH$_2$Cl$_2$. All pure fractions were concentrated to afford 9.88 g of the title D compound.

E. (2S,4R)-4-(4-methylphenylsulfonyloxy)methyl]-1-(phenylmethyl)-2-(t-butyldiphenylsilyloxymethyl) pyrrolidine p-Toluenesulfonyl chloride (3.10 g; 16.3 mmol) was added to a solution of the title D compound (4.56 g; 10.9 mmol) in 12 ml of pyridine at 0° C. After stirring 1 hour at 0° C. and 4 hours at room temperature, the reaction mixture was partitioned between NaHCO$_3$ solution and Et$_2$O. The organic layer was dried (MgSO$_4$) and concentrated. TLC indicated that significant amounts of the title D compound remained. The residue was redissolved in pyridine (12 ml) and p-toluenesulfonyl chloride (2 g; 11 mmol) was added. The reaction was allowed to stir an additional 18 hours. Workup as before gave a crude residue (5.8 g) which was flash chromatographed on a 5×25 cm SiO$_2$ column with Hex:EtOAc, 4:1. The pure fractions were concentrated to afford 4.44 g, of the title E compound as a light yellow oil.

F.

[3R-[1(3S*,5S*)3α,4α]]-1-[5-(t-butyldiphenylsilyloxymethyl)-1-(phenylmethyl)-3-pyrrolidinyl]-3-hydroxy-1,3,4,5-tetrahydro-4-(4-methoxyphenyl)-6-(trifluoromethyl)-2H-1-benazepin-2-one A mixture of (3R-cis-1,3,4,5-tetrahydro-3-hydroxy-4-(4-methoxyphenyl)-6-(trifluoromethyl)-2H-1-benazepin-2-one (1.58 g; 4.5 mmol), the title E compound (3.00 g; 5 mmol), and cesium carbonate (7.34 g; 22.5 mmol) was refluxed in 45 ml of distilled methyl ethyl ketone for 18 hours. After cooling to room temperature 50 ml of Et$_2$O was added and the suspension was filtered through celite. The filter cake was washed well with Et$_2$O and the filtrate was concentrated to a dark orange oil. The crude product was flash chromatographed on a 5×25 cm SiO$_2$ column which was eluted with 15% EtOAc/Hex. The pure fractions were concentrated to afford 2.4 g of the title F compound as a colorless foam.

G.

[3R-[1(3S*,5S*)3α,4α]]-1-[5-(hydroxymethyl)-1-(phenylmethyl)-3-pyrrolidinyl]-3-hydroxy-1,3,4,5-tetrahydro-4-(4-methoxyphenyl)-6-(trifluoromethyl)-2H-1-benazepin-2-one A solution of tetrabutyl ammonium fluoride (2.90 g; 9.18 mmol), in 15 ml of THF was added to a stirred solution of the title F compound (3.19 g; 4.17 mmol) in 35 ml of THF. After stirring two hours, the reaction was diluted with Et$_2$O (100 ml) and the Et$_2$O layer was washed with H$_2$O (50 ml) and brine (50 ml). The organic layer was dried (MgSO$_4$) and concentrated. The residue was flash chromatographed on a 5×30 cm SiO$_2$ column using 5% MeOH/CH$_2$Cl$_2$. The pure fractions were combined and the mixed fractions were rechromatographed on a 5×30 cm column using the following elution scheme: 1 L CH$_2$Cl$_2$, 1 L 1% MeOH/CH$_2$Cl$_2$, 1 L 2% MeOH/CH$_2$Cl$_2$, 500 ml 3% MeOH/CH$_2$Cl$_2$, and 500 ml 5% MeOH/CH$_2$Cl$_2$. The pure fractions from the previous run concentration afforded 1.788 g of the title G compound as a white foam.

H.

[3R-[1(3S*,5S*),3α,4α]]-1,3,4,5-Tetrahydro-3-hydroxy-1-[5-(hydroxymethyl)-3-pyrrolidinyl]-4-(4-methoxyphenyl)-6-(trifluoromethyl)-2H-1-benazepin-2-one, fumarate (1:1) salt The title G compound (1.55 g; 2.87 mmol) was hydrogenated over 20% Pd(OH)$_2$/C (175 mg) in EtOAc (30 ml) for 24 hours using a balloon apparatus. TLC at this time showed that substantial amounts of starting material remained. Additional 20% Pd(OH)$_2$/C (175 mg) was added and hydrogenation was continued for an additional 48 hours. The reaction was still not complete, so the reaction was filtered through celite and the filter cake was washed well with MeOH (~150 ml). The filtrate was concentrated to a dark residue which was redissolved in MeOH (30 ml) (fresh bottle). 20% Pd(OH)$_2$/C (370 mg) was added and the mixture was hydrogenated, as before, for 8 hours. After this time, the reaction was filtered and the filtrate was concentrated. The residue was chromatographed on a 5×25 cm SiO$_2$ column using the following elution scheme: 2 1 CH$_2$Cl$_2$:MeOH: Et$_3$N, 94:5:1; 1 CH$_2$Cl$_2$:MeOH: Et$_3$N, 89:10:1. The pure fractions were concentrated to a gray solid which was coevaporated from toluene: MeOH, 1:1 (50 ml) and EtOAc: MeOH, 1:1 (2×50 ml) to afford 1.04 g of the title compound.

The free base (972 mg; 2.158 mmol) was dissolved in MeOH and fumaric acid (250 mg; 2.158 mmol) was added as a solution in hot MeOH. This solution was concentrated to a foam, which was dissolved in a mixture of MeOH, I.P.A., and EtOH and filtered through celite. The filtrate was concentrated to a yellow crystalline solid which was triturated with hot IPA to afford 1.15 g of the title compound as a white crystalline solid, m.p. 212°–214° C. (dec.), 168° C. (softened), 185° C. (darkened). TLC: R$_f$=0.19, CH$_2$Cl$_2$:MeOH:NH$_4$OH, 95:4:1, (free base). [α]$_D$= +66.8 (c 1.0, MeOH).

Analysis calc'd for C$_{23}$H$_{25}$F$_3$N$_2$O$_4$·C$_4$H$_4$O$_4$·0.5C$_3$H$_8$O$_1$:
C, 57.38; H, 5.58; F, 9.55; N, 4.67.
Found: C, 57.33; H, 5.59; F, 9.41; N, 4.73.

EXAMPLE 42

3R-[1(3R*,5S*),3α,4α]]-1,3,4,5-Tetrahydro-3-hydroxy-1-[5-(hydroxymethyl)]-3-pyrrolidinyl]-4-(4-methoxyphenyl)-6-(trifluoromethyl)-2H-1-benazepin-2-one, fumarate (1:1) salt

A.

(2S,4S)-4-(phenylcarbonyloxy)-1-(phenylmethyl)-2-(t-butyldiphenylsilyloxymethyl) pyrrolidine Diethylazodicarboxylate (2.80 ml; 16.8 mm) was added dropwise over 5 minutes to a stirred solution of the title D compound from Example 41 (5 g; 11.2 mmol), triphenyl phosphine (4.41 g; 16.8 mmol), and benzoic acid (3.14 g; 28 mmol) in 110 ml of THF at room temperature. After stirring 2 hours the reaction mixture was partitioned between ethyl ether and saturated sodium carbonate solution. The organic layer was washed with saturated brine, dried (MgSO$_4$), and concentrated. The residue was flash chromatagraphed twice on a 5×25 cm silica gel column using 5:95 EtOAc:Hexane as the eluant. The purest fractions were concentrated to afford 3.97 g of the title A compound as a light yellow oil.

B.

(2S,4S)-4-hydroxy-1-(phenylmethyl)-2-(t-butyldiphenylsilyloxymethyl) pyrrolidine A mixture of the title A compound (3.95 g; 7.2 mmol), 1N NaOH (72 ml; 72 mmol), 72 of THF, and 72 ml of MeOH was refluxed for 1 hour. The reaction mixture was partitioned between brine and EtOAc. The EtOAc layer was washed with brine, dried (MgSO$_4$), and concentrated. The residue was flashed chromatagraphed on a 5×20 cm silica gel column using EtOAc: Hexane, 1:3 as the eluant. The pure fractions were concentrated to afford 1.85 g of the title B compound as a colorless oil.

C.

(2S,4S)-4-[(4-methylphenylsulfonyloxy)methyl]-1-(phenylmethyl)-2-(t-butyldiphenylsilyloxymethyl) pyrrolidine A mixture of the title B compound (1.85 g; 4.15 mmol) and p-toluenesulfonyl chloride (1.2 g; 6.25 mmol) in 5 ml of pyridine was stirred for 18 hours at room temperature. The reaction mixture was partitioned between saturated sodium carbonate solution and ethyl ether. The organic layer was washed with brine, dried (MgSO$_4$), and concentrated. The residue was flash chromatographed on a 5×25 cm silica gel column using EtOAc:Hexane, 1:9 as the eluant. The pure fractions were concentrated to afford 2.13 g of the title C compound as a colorless oil.

D.
[3R-[1(3R*,5S*)3α,4α]]-1-[5-(t-butyldiphenylsilyloxymethyl)-1-(phenylmethyl)-3-pyrrolidinyl]-3-hydroxy-1,3,4,5-tetrahydro-4-(4methoxyphenyl)-6-(trifluoromethyl)-2H-1-benazepin-2-one A mixture of the title C compound (2 g; 3.33 mmol), cesium carbonate (5.4 g; 16.7 mmol), (3R-cis)-3-hydroxy-4-(4-methoxyphenyl)-6-(trifluoromethyl)-2H-1-benzazepin-2-one (1.2 g; 3.33 mmol), and methyl ethyl ketone (30 ml) was refluxed for 20 hours. The reaction mixture was cooled to room temperature and 50 ml of ethyl ether was added. The resulting thick suspension was filtered through celite and the filtrate was concentrated to dryness. The residue was flashed chromatographed on a 5×35 cm silica gel column using EtOAc: Hexane, 1:4 as the eluant. Concentration of the pure fractions afforded 980 mg of the title D compound. Concentration of the mixed fractions yielded 800 mg of impure material which was rechromatographed on a 5×35 cm column using the following elution scheme: 3 L 15% EtOAc/Hexane, 1 L 25% EtOAc/Hexane. The pure fractions were combined with the pure fractions from the first column to afford 1.45 g of the title D compound as a colorless oil.

E.
[3R-[1(3R*,5S*)]3α,4α]]-1-[5-(hydroxymethyl)-1-(phenylmethyl)-3-pyrrolidinyl]-3-hydroxy-1,3,4,5-tetrahydro-4-(4-methoxyphenyl)-6-(trifluoromethyl)-2H-1-benazepin-2-one A 1N solution of tetra-n-butylammonium fluoride (3.65 ml; 3.65 mmol) was added to a solution of the title D compound (1.395 g; 1.83 mmol) in 20 ml of THF at room temperature. After stirring for one hour at room temperature, the reaction mixture was diluted with 50 ml of Et$_2$O and the resulting organic layer was washed with water (50 ml). After washing with brine and drying (MgSO$_4$), the filtrate was concentrated to a yellow foam, which was flash chromatographed on a 5×30 cm silica gel column using EtOAc:hex., 3:1 as the eluent. The pure fractions were concentrated to afford 0.85 g of the title E compound as white foam.

F.
[3R-[1(3R*,5S*),3α,4α]]-1,3,4,5-Tetrahydro-3-hydroxy-1-5-(hydroxymethyl)-3-pyrrolidinyl]-4-(4-methoxyphenyl)-6-(trifluoromethyl)-2H-1-benzazepin-2-one, fumarate (1:1) salt A mixture of the title E compound (0.80 g, 1.48 mmol) and 20% Pd(OH)$_2$/carbon in 20 ml of AcOH was hydrogenated using a balloon apparatus for 18 hours at room temperature. The catalyst was removed by filtration through celite and the filter cake was washed with 20 ml of AcOH. Removal of the AcOH in vacuo afforded an oil which was partitioned between saturated sodium carbonate and EtOAc. The organic layer was washed with saturated brine, dried (MgSO$_4$), and concentrated to a white foam. This foam was flash chromatographed on a 5×20 cm silica gel column which was eluted as follows: 1 L 5% MeOH/CH$_2$Cl$_2$, 1 L 10% MeOH/CH$_2$Cl$_2$, 2 L 15% MeOH/CH$_2$Cl$_2$, 500 ml MeOH: CH$_2$Cl$_2$, 1:1. The pure fractions were concentrated to afford 595 mg (89%) of the free base of the title compound as a white foam.

The free base (405 mg, 0.9 mmol) was dissolved in 3 ml of MeOH and a solution of fumaric acid (104 mg; 0.9 mmol) in 2 ml of hot MeOH was added. The resulting mixture was concentrated to a solid which was triturated with Et$_2$O and dried at 50° C, 0.5 mm Hg to afford 532 mg the title compound as a white powder, m.p. 121°-130° C. (dec.); [α]$_D$+68.0 (c=0.54, MeOH).
Analysis calc'd for C$_{28}$H$_{29}$F$_3$N$_2$O$_8$.1.41 H$_2$O:
C, 54.7B; H, 5.42; F, 9.63; N, 4.73;
Found: C, 55.16; H, 5.27; F, 9.24; N, 4.79.

EXAMPLE 43
(3R-cis)-1-[(4,5-Dihydro-1H-imidazol-2-yl)methyl]-1,3,4,5-tetrahydro-3-hydroxy-4-(4-methoxyphenyl)-6-(trifluoromethyl)-2H-1-benzazepin-2-one, monohydrochloride

A. 2-chloromethyl imidazoline hydrochloride

To a chilled solution of 2-chloromethyl imidazoline hydrochloride salt (3 g, 19.4 mmoles) (preparation of which has been described in Helv. Chim. Acta. 27, 1773 (1944)) in 5 ml H$_2$O, was added ca. 75 ml of anhydrous ethyl ether. To this solution was added excess solid potassium carbonate and the resulting mixture stirred for 10 minutes. The ether layer was decanted off, and the remaining slurry was washed four times with ca. .75 ml of anhydrous ethyl ether. The ethereal layers were combined and dried over anhydrous magnesium sulfate. Stripping of the solvent in vacuo left 1.89 g of the title A compound as a white foam, m.p. 63°-64° C.

B.
(3R-cis)-1-[(4,5-Dihydro-1H-imidazol-2-yl)methyl]-1,3,4,5-tetrahydro-3-hydroxy-4-(4-methoxyphenyl)-6-(trifluoromethyl)-2H-1-benzazepin-2-one, A solution of (3R-cis)-3-hydroxy-4-(4-methoxyphenyl)-6-(trifluoromethyl)-2H-1-benzazepin-2-one (4.44 g, 12.6 mmoles) and a 60% dispersion of NaH (0.62 g, 15.5 mmoles) in mineral oil in 70 ml of dry DMF (4 Å sieves) was heated at 70° C. for 30 minutes. Then 2-chloromethyl imidazoline (1.08 g, 9.1 mmoles) was added. The mixture was allowed to stir for 16 hours at 70° C. The reaction mixture was washed twice with ice-water. The organic layers were combined, dried over anhydrous magnesium sulfate and then evaporated in vacuo to yield a yellowish residue. The residue was dissolved in ethyl acetate and flash chromatographed, (800 ml silica gel, pretreated with a 10:1:1 EtOAc/MeOH/Et$_3$N solution). Elution with 10:1:0.1 EtOAc/MeOH/Et$_3$N gave 2.55 g of the title B compound, [α]$_D$= +116.5°, (c=1.07, MeOH).

C. (3R-cis)-1-[(4,5-Dihydro-1 H-imidazol-2-yl)-methyl]-1,3,4,5-tetrahydro-3-hydroxy-4-(4-methoxyphenyl)-6-(trifluoromethyl)-2H-1benzazepin-2-one, monohydrochloride A solution of the title B compound (1.02 g, 23.5 mmoles) in 30 ml of acetonitrile was treated with excess ethereal HCl. Solvents were removed by vacuum evaporation and the residue triturated with anhydrous ethyl ether to yield the title compound (1.03 g). The title compound (0.96 g, 2.04 mmoles) was recrystallized from methylene chloride and isopropyl ether to yield 0.86 g of the title compound, m.p. 128-130° C., [α]$_D$= +90.6°, (c=0.98, MeOH).
Analysis calc'd for C$_{22}$H$_{22}$F$_3$N$_3$O$_3$.HCl.1.2H$_2$O: C, 53.77; H, 5.21; N, 8.55; Cl, 7.21; F, 11.60; Found: C, 53.77; H, 4.91; N, 8.55; Cl, 7.14; F, 11.38.

EXAMPLE 44 cis-1[(4,5-Dihydro-1H-imidazol-2-yl)methyl]-1,3,4,5-tetrahydro-3-hydroxy-7-(methoxymethoxy)-4-(4-methoxyphenyl)-2H-1-benzazepin-2-one, fumarate (1:1) salt The title compound was prepared using the procedure described in Example 43 but substituting cis-3-hydroxy-7-methoxymethoxy-4-(4-methoxyphenyl)-2H-1-benzazepin-2-one for (3R-cis)-3-hydroxy-4-(4-methoxyphenyl)-6-(trifluoromethyl)- 2H-1-benzazepin-2-one in step B of that example, m.p. 200–210° C. (dec.).

Analysis calc'd for $C_{23}H_{27}N_3O_5 \cdot C_4H_4O_4 \cdot 0.83H_2O$: C, 58.28; H, 5.91; N, 7.55; Found: C, 58.46; H, 5.73; N, 7.37.

EXAMPLE 45

(3R-cis)-1,3,4,5-Tetrahydro-3-hydroxy-1-[(1H-imidazol-2-yl)methyl]-4-(4-methoxyphenyl)-6-(trifluoromethyl)-2H-1-benzazepin-2-one, monohydrochloride

A.

(3R-cis)-1-[(1H-3-phenylmethyl-imidazol-2-yl)methyl]-1,3,4,5-tetrahydro-3-hydroxy-4-(4-methoxyphenyl)-6-(trifluoromethyl)-2H-1-benzazepin-2-one A solution of (3R-cis)-3-hydroxy-4-(4-methoxyphenyl)-6-(trifluoromethyl)-2H-1-benzazepin-2-one (2.02 g, 5.74 mmoles), 1-phenylmethyl-2-chloromethylimidazole hydrochloride (1.67 g, 6.87 mmoles) (preparation of which is described in JACS, 71, 383 (1949)) and a 60% dispersion of NaH in mineral oil (0.59 g, 14.8 mmoles, 2.6 eq.) was left stirring overnight.

The reaction was quenched with 1N HCl and then neutralized with 50% NaOH to pH~11. The reaction mixture was extracted twice with EtOAc. The organic layers were combined and washed 2×50 mL saturated NaHCO₃, followed by 2×50 ml washes of brine. Solvents were removed in vaco to yield a reddish-brown oil. Flash chromatography on 800 ml of LPS-1 silica gel using 20:1 EtOAc/MeOH gave 1.11 g of the title A compound as a white solid foam, $[\alpha]_D = +105.0°$, (c=1.01, MeOH).

B.

(3R-cis)-1-[(1H-imidazol-2-yl)methyl]-1,3,4,5-tetrahydro-3-hydroxy-4-(4-methoxyphenyl)-6-(trifluoromethyl)-2H-1-benzazepin-2-one A solution of the title A compound (1.09 g, 1.95 mmoles) and 10% Pd/C (0.24 g) in 5 ml of 95% alcohol was hydrogenated at atmospheric pressure overnight.

The reaction mixture was filtered and solvents removed in vacuo. The residue was taken up in EtOAc and washed with 1N NaOH. The aqueous phase was extracted three times with EtOAc. The combined organic layers were dried (MgSO₄) and concentrated in vacuo to yield 0.6660 g of the title B compound as a white solid foam.

C.

(3R-cis)-1,3,4,5-Tetrahydro-3-hydroxy-1-[(1H-imidazol-2-yl)methyl]-4-(4-methoxyphenyl)-6-(trifluoromethyl)-2H-1-benzazepin-2-one, monohydrochloride A solution of the title B compound (0.52 g, 1.21 mmoles) in acetonitrile was treated with excess ethereal HCl. Volatiles were removed in vacuo, yielding a white solid. The solid was triturated with IPE and dried in vacuo over P₂O₅ at 100° to give 0.45 g of the title compound, m.p. 188°–191°, $[\alpha]_D = +101.0°$, (c=1.02, MeOH).

Analysis calc'd for $C_{22}H_{20}F_3N_3O_3 \cdot HCl \cdot 0.2\ H_2O$: C, 56.03; H, 4.58; N, 8.91; Cl, 7.52; F, 12.09; Found: C, 56.20; H, 4.35; N, 8.92; Cl, 7.15; F, 11.71.

EXAMPLE 46

[2S-[2α,3α,5(R*)]]-3-(Acetyloxy)-2,3-dihydro-2-(4-methoxyphenyl)-5-(2-pyrrolidinylmethyl)-1,5-benzothiazepin-4(5H)-one, monohydrochloride

A.

S-1-(t-butoxycarbonyl)-2-[(4-methylphenylsulfonyloxy)-methyl]-pyrrolidine

To S-1-(t-butoxycarbonyl)-2-pyrrolidinemethanol (20.6 g, 102.4 mmol) in pyridine (100 ml) at room temperature under argon was added with stirring p-toluenesulfonyl chloride (23.4 g, 122.8 mmol). After 5 hours, additional p-toluenesulfonyl chloride (9.8 g, 51.2 mmol) was added. After a total of 23 hours stirring, the reaction mixture was diluted with EtOAc and washed with saturated aqueous CuSO₄ solution (×3). The organic layer was dried (MgSO₄), filtered and concentrated. The yellow liquid was chromatographed on a silica gel column and eluted with 10–30% EtOAc-hexane to give the title A compound (32.1 g) as a viscous colorless liquid.

B. [2S-[2α,3α,5(R*)]]-2,3-dihydro-3hydroxy-2-(4-methoxyphenyl)-5-(1-(t-butoxycarbonyl)-2-pyrrolidinylmethyl]-1,5-benzothiazepin-4-(5H)-one (2S-cis)-2,3-dihydro-3-hydroxy-2-(4-methoxyphenyl)-1,5-benzothiazepin-4(5H)-one (3.56 g, 11.81 mmol), cesium carbonate (5.77 g, 17.72 mmol) and the title A compound (6.30 g, 17.72 mmol) in DMF (40 ml) were heated to 50° C. After 16 hours the reaction mixture was cooled to room temperature, diluted with water and extracted with ether (×3). The combined extract was washed with 10% aqueous LiCl (×3), dried (MgSO₄), filtered and concentrated. The yellow foam was chromatographed on a silica gel column. Elution with 10–25% EtOAc in hexane gave the title B compound (4.51 g) as a yellow foam.

C.

[2S-[2α,3α,5(R*)]]-2,3-dihydro-3-(acetyloxy)-2-(4-methoxyphenyl)-5-(1-(t-butoxycarbonyl)-2-pyrrolidinyl]methyl]-1,5-benzothiazepin-4-(5H)-one The title B compound (1.0 g, 2.06 mmol), 4-dimethylaminopyridine (0.50 g, 4.13 mmol) and acetic anhydride (1.05 ml, 10.3 mmol) in CH₂Cl₂ (20 ml) were stirred at room temperature under argon for 15 hours. The reaction solution was absorbed onto silica gel (60–200 mesh) and chromatographed on a silica gel column. Elution with 5–20% EtOAc in hexane afforded the title C compound (0.94 g) as a white solid.

D.

[2S-[2α,3α,5(R*)]]-3-(Acetyloxy)-2,3-dihydro-2-(4-methoxyphenyl)-5-(2-pyrrolidinylmethyl)-1,5-benzothiazepin-4(5H)-one, monohydrochloride The title C compound (0.84 g, 1.60 mmol) in trifluoroacetic acid (5 ml) and CH₂Cl₂ (5 ml) was stirred under argon at room temperature for 1 hour. The reaction solution was concentrated at reduced pressure, then diluted with aqueous KHCO₃ and extracted with EtOAc (×3). The combined extracts were dried (MgSO₄), filtered and concentrated. The yellow foam was dissolved in EtOAc and excess ethereal HCl was added. Concentration followed by trituration with ether (50 ml) yielded the title compound (0.75 g) as a white foam, m.p. 132°–135° C., $[\alpha]_D = +66.06°$ (c=1, MeOH).

Analysis calc'd for $C_{23}H_{26}N_2O_4S \cdot HCl \cdot 0.73 H_2O$: C, 58.01; H, 6.03; N, 5.88; Cl, 7.44; S, 6.73; Found: C, 58.00; H, 6.06; N, 5.89; Cl, 7.18; S, 6.48.

EXAMPLE 47

[2S-[2α,3α,5(R*)]]-3-(Acetyloxy)-2,3-dihydro-8-methoxy-2-(4-methoxyphenyl)-5-(2-pyrrolidinylmethyl)-1,5-benzothiazepin-4(5H)-one, monohydrochloride The title compound was prepared using the procedure of Example 46 above but substituting cis-2,3-dihydro-3-hydroxy-2-(4-methoxyphenyl)-8-methoxy-1,5-benzothiazepin-4(5H)-one for (2S-cis)-2,3-dihydro-3-hydroxy-2-(4-methoxyphenyl)-1,5-benzothiazepin-4(5H)-one in part B of that example, m.p. 147°–154° C., $[\alpha]_D = +50.0°$ (c=1, MeOH).

Analysis calc'd for $C_{24}H_{28}N_2O_5S \cdot HCl \cdot 0.89 H_2O$: C, 56.63; H, 6.09; N, 5.51; Cl, 6.97; S, 6.30; Found: C, 56.72; H, 5.94; N, 5.42; Cl, 7.15; S, 6.30.

EXAMPLE 48

[2S-[2α,3α,5(R*)]]-2,3-Dihydro-3-hydroxy-2-(4-methoxyphenyl)-5-(2-pyrrolidinylmethyl)-1,5-benzothiazepin-4(5H)-one, monohydrochloride

A.

[2S-[2α,3α,5(R*)]]-2,3-dihydro-3-hydroxy-2-(4-methoxyphenyl)-5-(1-(benzyloxycarbonyl)-2-pyrrolidinyl]methyl]-1,5-benzothiazepin-4(5H)-one (2S-cis)-2,3-dihydro-3-hydroxy-2-(4-methoxyphenyl)-1,5-benzothiazepin-4(5H)-one (1.25 g, 4.15 mmol), cesium carbonate (2.03 g, 6.22 mmol) and S-1-(benzyloxycarbonyl)-2-[(4-methylphenylsulfonyloxy)methyl]-pyrrolidine (2.02 g, 5.19 mmol) in DMF (20 ml) were heated to 50° C. After 23 hours the reaction mixture was cooled to room temperature, diluted with water and extracted with ether (×3). The combined extract was washed with 10% aqueous LiCl (×3), dried (MgSO₄), filtered and concentrated. The viscous yellow oil was chromatographed on a silica gel column and eluted with 15–30% EtOAc:hexane to give the title A compound (1.74 g) as a white solid.

B.

[2S-[2α,3α,5(R*)]]-2,3-Dihydro-3-hydroxy-2-(4-methoxyphenyl)-5-(2-pyrrolidinylmethyl)-1,5-benzothiazepin-4(5H)-one, monohydrochloride The title A compound (1.2 g, 2.31 mmol), 10% Pd/C (1.2 g, 100% (w/w)), and ammonium formate (1.2 g, 19.0 mmol) in methanol (40 ml) was heated to reflux. After 5 hours, additional Pd/C (0.6 g) was added and stirring was continued for another 19 hours. The reaction mixture was cooled to room temperature and anhydrous MgSO₄ was added before it was filtered to remove the catalyst. The solids were washed well with MeOH. The filtrate was concentrated and the residue diluted with saturated aqueous KHCO₃ and extracted with EtOAc (×3). The combined extract was dried (MgSO₄), filtered and concentrated to yield a pale yellow foam which was dissolved in CH₂Cl₂. To this was added excess ethereal HCl. Removal of the volatiles at reduced pressure followed by trituration of the resulting solids with a 2:1 ether-CH₂Cl₂ mixture gave the title compound (0.35 g) as an amorphous white solid, m.p. >240° C. (dec.), $[\alpha]_D = +91.6°$ (c=1, MeOH).

Analysis calc'd for $C_{21}H_{24}N_2O_2S \cdot 1.1.1HCl \cdot 0.46 H_2O$: C, 58.26; H, 6.06; N, 6.47; Cl, 9.01; S, 7.41; Found: C, 58.45; H, 5.76; N, 6.28; Cl, 9.35; S, 7.41.

EXAMPLE 49

[2S-[2α,3α,5(R*)]]-2,3-Dihydro-2-(4-methoxyphenyl)-3-(2-methyl-1-oxopropoxy)-5-(2-pyrrolidinylmethyl)-1,5-benzothiazepin-4(5H)-one, monohydrochloride

A.

[2S-[2α,3α,5(R*)]]-2,3-dihydro-3-(2-methyl-1-oxopropoxy)-2-(4-methoxyphenyl)-5-(1-(t-butoxycarbonyl)-2-pyrrolidinyl]methyl]-1,5-benzothiazepin-4(5H)-one A solution of [2S-[2α,3α,5(R*)]]-2,3-dihydro-3-hydroxy-2-(4-methoxyphenyl)-5-(1-(t-butoxycarbonyl)-2-pyrrolidinyl]methyl]-1,5-benzothiazepin-4(5H)-one (847 mg, 1.75 mmol), N,N-dimethylaminopyridine (427 mg, 3.5 mmol) and isobutyric anhydride (600 ml, 3.6 mmol) in CH₂Cl₂ (25 ml) was stirred at room temperature for 3 hours. The reaction mixture was concentrated under reduced pressure and the residual oil was chromatographed on a silica gel column. Elution with 10–20% EtOAc in hexane afforded the title A compound (0.870 g) as a white foam.

B.

[2S-[2α,3α,5(R*)]]-2,3-Dihydro-2-(4-methoxyphenyl)-3-(2-methyl-1-oxopropoxy)-5-(2-pyrrolidinylmethyl)-1,5-benzothiazepin-4(5H)-one, monohydrochloride The title A compound (1.02 g, 1.84 mmol) in CH₂Cl₂ (5 ml) and trifluoroacetic acid (5 ml) was stirred at room temperature for 15 minutes. The reaction mixture was then concentrated at reduced pressure and the resulting residue was dissolved in EtOAc and washed with saturated aqueous KHCO₃. The aqueous layer was extracted with EtOAc (3 times) and the combined organic layers were dried (MgSO₄), filtered and concentrated. The yellow solid was chromatographed on a silica gel column (pretreated with 1% Et₃N) and eluted with 7% MeOH in CH₂Cl₂. The free amine was dissolved in ether and converted to the hydrochloride salt by the addition of excess ethereal HCl. Concentration yielded a pale yellow foam which was triturated well with ether and filtered off to yield the title compound (0.70 g) as a yellow solid, m.p. 197–199° C. (dec.), $[\alpha]_D = +34.86$ (c=1, MeOH).

Analysis calc'd for $C_{25}H_{30}N_2O_4S \cdot HCl \cdot 0.3 H_2O$: C, 60.47; H, 6.42; N, 5.64; Cl, 7.14; S, 6.46; Found: C, 60.32; H, 6.38; N, 5.76; Cl, 6.80 S, 6.55.

EXAMPLE 50

[2S-[2α,3α,5(R*)]]-2,3-Dihydro-2-(4-methoxyphenyl)-3-[[(methylamino)carbonyl]oxy]-5-(2-pyrrolidinylmethyl)-1,5-benzothiazepin-4(5H)-one, monohydrochloride

A.

[2S-[2α,3α,5(R*)]]-2,3-dihydro-3-[[(methylamino)carbonyl]oxy]-2-(4-methoxyphenyl)-5-(1-(t-butoxycarbonyl)-2-pyrrolidinyl]methyl]-1,5-benzothiazepin-4(5H)-one To a solution of [2S-[2α,3α,5(R*)]]-2,3-dihydro-3-hydroxy-2-(4-methoxyphenyl)-5-(1-(t-butoxycarbonyl)-

2-pyrrolidinyl]methyl]-1,5-benzothiazepin-4(5H)-one (1.0 g, 2.06 mmol) in anhydrous CH$_2$Cl$_2$ (15 ml) at 0° C. was added with stirring triethyl amine (116 ml, 0.82 mmol) and methyl isocyanate (0.19 g, 3.30 mmol). The reaction mixture was allowed to warm to room temperature. After 10 hours, additional methyl isocyanate (0.19 g, 3.39 mmol) was added and the stirring continued for another 5 hours. Water was added and the aqueous mixture was extracted with EtOAc (×3). The combined organic extracts were dried (MgSO$_4$), filtered and concentrated. The crude white foam was chromatographed on a silica gel column and eluted with 10-20% EtOAc in hexane to obtain the title A compound (0.89 g) as a white foam.

B.
[2S-[2α,3α,5(R*)]]-2,3-Dihydro-2-(4-methoxyphenyl)-3-[[(methylamino)carbonyl]oxy]-5-(2-pyrrolidinylmethyl)-1,5-benzothiazepin-4(5H)-one, monohydrochloride The title A compound (0.89 g, 1.64 mmol) in CH$_2$Cl$_2$ (5 ml) and trifluoroacetic acid (5 ml) was stirred at room temperature for 30 minutes. The reaction mixture was concentrated and the resulting residue was dissolved in EtOAc and washed with saturated aqueous KHCO$_3$. The organic layer was separated and the aqueous layer was extracted with EtOAc (×2). The combined organic layers were dried (MgSO$_4$), filtered and concentrated. The free base was dissolved in ether with a minimal amount of EtOAc added to insure a homogeneous solution. Excess ethereal HCl was added and the volatiles were removed under reduced pressure to obtain the title compound (0.66 g) as a pale yellow solid, m.p. 170°-177° C., $[\alpha]_D = +37.02°$ (=1, MeOH).

Analysis calc'd for C$_{23}$H$_{27}$N$_3$O$_4$S.HCl 1.0 H$_2$O: C, 55,70; H, 6.10; N, 8.47; Cl, 7.15 S, 6.46; Found: C, 55.79; H, 5.81; N, 8.49; Cl, 7.03 S, 6.50.

EXAMPLE 51

[3R-[1(S*),3α,4α]]-3-(Acetyloxy)-1,3,4,5-tetrahydro-7-methoxy-4-(4-methoxyphenyl)-1-(2-pyrrolidinylmethyl)-2H-1-benzazepin-2-one, monohydrochloride The title compound was prepared using the procedures of Example 13 employing cis-3-hydroxy- 7-methoxy-4-(4-methoxyphenyl)-2H-1-benzazepin-2-one, m.p. >250° C., $[\alpha]_D = +92.17°$ (c=1, MeOH).

Analysis calc'd for C$_{25}$H$_{30}$N$_2$O$_5$.HCl 0.2 H$_2$O: C, 62.74; H, 6.61; N, 5.86; Cl, 7.41; Found: C, 62.88; H, 6.70; N, 6.04; Cl, 7.26.

EXAMPLE 52

[2S-(2α,3α)]-2,3-Dihydro-5-[(4,5-dihydro-1H-imidazol-2-yl)methyl]-3-hydroxy-2-(4-methoxyphenyl)-1,5-benzothiazepin-4(5H)-one, monohydrochloride The title compound was prepared using the procedures of Example 43 employing (2S-cis)-2,3-dihydro-3-hydroxy-2-(4-methoxyphenyl)-1,5-benzothiazepin-4(5H)-one. The product was crystallized from ethanol, m.p. 252° C. (dec.), $[\alpha]_D = +94.0°$ (c=1.0, MeOH); R$_f$ 0.28 (18:1:1 CH$_2$Cl$_2$ :MeOH:AcOH).

Analysis calc'd for C$_{20}$H$_{21}$N$_3$O$_3$S.HCl.0.7 H$_2$O: C, 55.53; H, 5.45; N, 9.71; Cl, 8.20; S, 7.41; Found: C, 55.38; H, 5.64; N, 9.68; Cl, 8.50; S, 7.55.

EXAMPLE 53

[2S-(2α,3α)]-3-(Acetyloxy)-2,3-dihydro-2-(4-methoxyphenyl)-5-(2-pyridinylmethyl)-1,5-benzothiazepin-4(5H)-one, monohydrochloride The title compound was prepared by heating the title compound of Example 23 with acetic anhydride for 3 hours at 110°-115°. After crystallization from acetonitrile, the colorless product melted at 200°-202° C. (dec.); $[\alpha]_D = +137°$ (c=1.0, MeOH).

Analysis calc'd for C$_{24}$H$_{22}$N$_3$O$_4$S.HCl.1.5 H$_2$O: C, 57.88; H, 5.26; N, 5.63; Cl, 7.12; S, 6.44; Found: C, 58.09; H, 5.20; N, 5.62; Cl, 7.48; S, 6.52.

EXAMPLE 54

(3R-cis)-3-(Acetyloxy)-1-[(4,5-dihydro-1H-imidazol-2-yl)methyl]-1,3,4,5-tetrahydro-4-(4-methoxyphenyl)-6-(trifluoromethyl)-2H-1-benzazepin-2-one, monohydrochloride

A.
(3R-cis)-1-[(4,5-Dihydro-1-(t-butoxycarbonyl)-imidazol-2-yl)methyl]-1,3,4,5-tetrahydro-3-hydroxy-4-(4-methoxyphenyl)-6-(trifluoromethyl)-2H-1-benzazepin-2-one A solution of the title compound of Example 43 (3.83 g, 8.84 mmol) in 30 ml of dry CH$_2$Cl$_2$ was treated with t-BOC anhydride (2.77 g, 12.7 mmol, 1.4 eq) and DMAP (0.11 g, 0.90 mmol, 10 mol). The solution was allowed to stir overnight. The reaction mixture was concentrated to ca 15 ml and flash chromatographed on ca 800 ml of LPS-1 silica gel using 2:1 Hexane/EtOAc as the mobile phase. Removal of solvents in vacuo left 1.51 g of the title A compound as a white solid foam, m.p. 116°-° C.

B.
(3R-cis)-3-(Acetyloxy)-1-[(4,5-dihydro-1-(t-butoxycarbonyl)-imidazol-2yl) methyl]-1,3,4,5-tetrahydro-4-(4-methoxyphenyl)-6-(trifluoromethyl)-2H-1-benzazepin-2-one A solution of the title A compound (1.50 g, 2.8 mmol) in 30 ml of dry CH$_2$Cl$_2$ was treated with acetic anhydride (1.66 g, 16.2 mmol, 5.8 eq) and DMAP (0.68 g, 5.7 mmol, 2 eq). The solution was allowed to stir overnight. The reaction mixture was adsorbed on ca 30 ml of celite, and chromatographed on 350 ml of LPS-1 silica gel (1.5:1:0.1 Hexane/EtOAc/MeOH). Removal of solvents in vacuo left 0.96 g of the title B compound as a white foam, m.p. 105°-108° C.

C.
(3R-cis)-3-(Acetyloxy)-1-[(4,5-dihydro-1H-imidazol-2-yl)methyl]-1,3,4,5-tetrahydro-4-(4-methoxyphenyl)-6-(trifluoromethyl)-2H-1-benzazepin-2-one, monohydrochloride A solution of the title B compound (0.87 g, 1.5 mmol) in 10 ml of dry CH$_2$Cl$_2$ was treated with 10 ml of trifluoroacetic acid. The reaction mixture was left stirring at room temperature for 2 hours. The solvents were removed in vacuo, and the resulting oil taken up in EtOAc. The EtOA layer was washed twice with saturated K$_2$CO$_3$ followed by brine. The organic layer was dried over MgSO$_4$ and solvents removed in vacuo to yield 0.770 g of a white foam, m.p. 109°-111° C. A solution of the above free base (0.740 g, 1.6 mmol) in EtOAc was treated with excess ethereal HCl. The solid that formed was collected and washed four times with EtOAc. The solid was dissolved off the filter with $CH_3CN$ and solvents removed in vacuo to yield 0.42 g (51%) of the title compound as a white solid, m.p. 260°–261° C., $[\alpha]_D = +84.6$, (c=1.11, MeOH).

Analysis calc'd for $C_{24}H_{24}F_3N_3O_4 \cdot HCl \cdot 1.43\ H_2O$: C, 53.72; H, 5.04; N, 7.83; Cl, 10.62; F, 6.61; Found: C, 53.87; H, 5.14; N, 7.68; Cl, 10.70; F, 6.79.

EXAMPLE 55

(3R-cis)-1-[(4,5-Dihydro-1H-imindazol-2-yl)methyl]-1,3,4,5-tetrahydro-3-hydroxy-7-methoxy-4-(4-methoxyphenyl)-2H-1-benzazepin-2-one, monohydrochloride

A.

[3R-(3α,4α,3S*)]-3-(2-Benzyloxycarbonylamino-3-phenyl)propionyl-1,3,4,5-tetrahydro-7-methoxy-4-(4-methoxyphenyl)-2H-1-benzazepine-2-one A suspension of (cis)-1,3,4,5-tetrahydro-3-hydroxy-7-methoxy-4-(4-methoxyphenyl)-2H-1-benzazepin-2-one (7.24 g, 23.1 mmole) in 70 ml of tetrahydrofuran was treated with 2S-N-carbobenzyloxyamino phenylalanine (8.60 g, 28.88 mmole) followed by water soluble carbodiimide (8.82 g, 46.2 mmole). After one hour, N,N-dimethylaminopyridine (566 mg) was added and the homogeneous solution was stirred at room temperature for 1.5 hours. 250 ml of ether was added to the reaction mixture and it was filtered. The filtrate was washed with 250 ml of each of 1 N aqueous hydrochloric acid solution, saturated sodium bicarbonate solution and brine, dried over anhydrous magnesium sulfate, filtered and concentrated. The residue was chromatographed on a silica gel column and eluted with d50-75% ethyl acetate in hexanes, followed by ethyl acetate to obtain 10.5 g of a white foam. The white foam was further chromatographed and eluted with 50% ethyl acetate in hexanes to obtain 4.4 g of the diastereomeric (3S-cis) product and 4.6 g of the (3R-cis) title A compound.

B.

(3R-cis)-1,3,4,5-Tetrahydro-3-hydroxy-7-methoxy-4-(4-methoxyphenyl)-2H-1-benzazepin-2-one A stirred suspension of the title A compound (4.6 g, 7.73 mmole) in 85 ml of methanol was treated with a 25% solution of sodium methoxide in methanol (5.52 ml, 23.19 mmole). Within 5 to 10 minutes, all the solids went into solution. After 30 minutes, the mixture was poured into 250 ml of 1 N aqueous acid solution and was extracted three times with ethyl acetate. The ethyl acetate extracts were combined, dried over anhydrous sodium sulfate, filtered and concentrated. The residue was triturated with ethyl acetate-hexanes (1:1) and the precipitated solid was filtered, dried in vacuo to obtain 1.73 g of the title compound. The mother liquor was concentrated and was then chromatographed on a silica gel column and eluted with 50 to 75% ethyl acetate in hexanes to obtain additional 350 mg of the title B product as a white solid, m.p. 171°–173° C., $[\alpha]_D = 187°$ (c 0.55, methanol).

C.

(3R-cis)-1-[(4,5-dihydro-1H-imidazol-2-yl)methyl]-1,3,4,5-tetrahydro-3-hydroxy-7-methoxy-4-(4-methoxyphenyl)-2H-benzazepin-2-one, monohydrochloride Sodium hydride (100 mg, 4.14 mmole) was added with stirring to a solution of the title B compound (1.08 g, 3.45 mmole) in 15 ml of dry dimethylformamide. After 30 minutes, 2-chloromethyl imidazoline (490 mg, 4.14 mmole) was added. The mixture was stirred at room temperature for 1.5 hours and was then quenched with water. The mixture was extracted three times with ethyl acetate. The ethyl acetate extracts were combined and washed three times with 10% aqueous lithium chloride solution. The ethyl acetate extract was then washed with dilute aqueous hydrochloric acid solution and with water. The aqueous extracts were combined, basified with solid potassium bicarbonate and extracted five times with methylene chloride. The methylene chloride extracts were combined, dried over anhydrous magnesium sulfate, filtered and concentrated to obtain 1.32 g of the free base of the title compound as a white solid. A solution of the free base (1.8 g) in methylene chloride-ethyl acetate was treated dropwise with excess etheral hydrogen chloride and the precipitated white solid was filtered, washed twice with ethyl acetate and twice with etherm dried in vacuo to obtain 1.64 g of the title compound, m.p. 183°–188° C.; $[\alpha]_D = +155.5°$ (c=1.0, methanol).

Analysis calculated for $C_{22}H_{25}N_3O_5 \cdot HCl\ 0.62\ H_2O$: C, 59.78; H, 5.98; N, 9.51; Cl, 8.02. Found: C, 59.36; H, 6.14; N, 9.43; Cl, 7.92.

EXAMPLE 56

(3R-cis)-3-(Acetyloxy)-1-[(4,5-dihydro-1H-imidazol-2-yl)methyl]-1,3,4,5-tetrahydro-7-methoxy-4(4-methoxyphenyl)-2H-1-benzazepin-2-one, monohydrochloride The title compound was prepared from (3R-cis)-1-[(4,5-dihydro-lH-imidazol-2-yl)methyl]-1,3,4,5-tetrahydro-3-hydroxy-7-methoxy-4(4-methoxyphenyl)-2H-benzazepin-2-one according to
10 the procedure described in Example 54, m.p. >270° C. $[\alpha]_D = +95.0°$ C. (c=1.0, methanol).

Analysis calculated for $C_{24}H_{27}N_3O_5 \cdot HCl\ 0.72\ H_2O$: C, 59.19; H, 6.09; N, 8.63; Cl, 7.28. Found: C, 59.36; H, 5.75; N, 8.46; Cl, 7.05.

EXAMPLE 57

[3R-[1(S*),3α,4α]]-1,3,4,5-Tetrahydro-3-hydroxy-7-methoxy-4-(4-methoxyphenyl)-1-(2-pyrrolidinylmethyl)-2H-1-benzazepin-2-one, monohydrochloride

A.

[3R-[1(S*),3α,4α]]-1,3,4,5-Tetrahydro-3-hydroxy-7-methoxy-4-(4-methoxyphenyl)-1-[[(N-benzyloxycarbonyl)pyrrolidin-2-yl]methyl]-2H-1-benzazepin-2-one Prepared from (cis)-1,3,4,5-tetrahydro-3-hydroxy-7-methoxy-4-(4-methoxyphenyl)-2H-1-benzazepin-2-one (Part E of Example 55) following the procedure described in the preparation of the title compound of part A of Example 38.

B.

[3R-[1(S*),3α,4α]]-1,3,4,5-Tetrahydro-3-hydroxy-7-methoxy-4-(4-methoxyphenyl)-1-(2-pyrrolidinylmethyl)-2H-1-benzazepin-2-one, monohydrochloride Prepared from [3R-[1(S*),3α,4α]]-1,3,4,5-Tetrahydro-3-hydroxy-7-methoxy-4-(4-methoxyphenyl)-1-[[(N-benzyloxycarbonyl)pyrrolidin-2-yl]methyl]-2H-1-benzazepin-2-one following the procedure described in the preparation of the title compound of Example 16, m.p. 179°–181° C. $[\alpha]_D = +109.4°$ (c =1.0, methanol).

Analysis calculated for $C_{24}H_{28}N_2O_4 \cdot HCl\ 0.48\ H_2O$: C, 62.55; H, 6.84; N, 6.35; Cl, 8.03. Found: C, 62.86; H, 6.88; N, 6.04; Cl, 8.23.

EXAMPLE 58

[2S-[2α,3α,5(R*)]]-2,3-dihydro-3-hydroxy-8-methoxy-2-(4-methoxyphenyl)-5-(2-pyrrolidinylmethyl)-1,5-benzothiazepin-4-(5H)-one, monohydrochloride

A.

[2S-[2α,3α,3(R*)]]-2,3-dihydro-3-(2-benzyloxycarbonylamino-3-phenyl)propionyl-8-methoxy-2-(4-methoxyphenyl)-1,5-benzothiazepin-4-(5H)-one (2-S)-Carbobenzyloxyamino phenylalanine (6.88 g, 22.99 mmol) was added at room temperature with stirring to cis-2,3-dihydro-3-hydroxy-8-methoxy-2-(4-methoxyphenyl)-1,5-benzothiazepin-4-(5H)-one (6.09 g, 18.4 mmol) in dry dimethylformamide (55 ml) under argon. Water soluble carbodiimide (7.05 g, 36.7 mmol) was added, followed after one hour by dimethylaminopyridine (0.45 g, 3.7 mmol). Stirring was continued for 75 minutes, the mixture was diluted with ether (280 ml), washed with 1 N hydrochloric acid, saturated sodium bicarbonate, saturated brine, dried over magnesium sulfate, and concentrated in vacuo. The mixture was purified by chromatography, followed by reverse phase HPLC to give the title A compound (1.30 g).

B.

(2S-cis)-2,3-Dihydro-3-hydroxy-8-methoxy-2-(4-methoxyphenyl)-1,5-benzothiazepin-4-(5H)-one The title A compound (1.30 g, 2.12 mmol) in methanol (21 ml) and water (0.2 ml) under argon was treated with 25% sodium methoxide in methanol (1.0 ml, 4.3 mmol). Stirring was continued for 90 minutes and the mixture was diluted with water (100 ml) and stirred an additional 30 minutes. The colorless solid product was collected by filtration, m.p. 180°–183° C. (dec). $[\alpha]_D = +85.4°$ (c =0.79, dimethylformamide).

C.

[2S-[2α,3α,5(R*)]]-2,3-dihydro-3-hydroxy-8-methoxy-2-(4-methoxyphenyl)-5-(2-pyrrolidinylmethyl)-1,5-benzothiazepin-4-(5H)-one monohydrochloride The title compound was prepared from (2S-cis)-2,3-dihydro-3-hydroxy-8-methoxy-2-(4-methoxyphenyl)-1,5-benzothiazepin-4-(5H)-one following the procedures described in Example 46, parts B and D, m.p. 121°–124° C. (dec). $[\alpha]_D = +62.9$ (c=1.08, methanol).

Analysis calc'd for $C_{23}H_{25}N_3ClSO_5 \cdot HCl \cdot 2.14H_2O$: C, 53.98; H, 6.44; N, 5.72; Cl, 7.24; S, 6.55. Found: C, 53.99; H, 6.02; N, 5.71; Cl, 7.57; S, 6.65.

EXAMPLE 59

(2S-cis)-5-[4,5-Dihydro-1H-imidazol-2-yl)methyl]-2,3-dihydro-3-hydroxy-8-methoxy-2-(4-methoxyphenyl)-1,5-benzothiazepin-4-(5H)-one, monohydrochloride The title compound was prepared from (2S-cis)-2,3-dihydro-3-hydroxy-8-methoxy-2-(4-methoxyphenyl)-1,5-benzothiazepin-4-(5H)-one as described in Example 43, m.p. 192°–199° C. $[\alpha]_D = +62.9°$ (c=1.0, methanol).

Analysis calculated for $C_{21}H_{22}N_3O_4S \cdot HCl \cdot 0.66 H_2O$: C, 54.30; H, 5.30; N, 9.05; Cl, 8.40; S, 6.90. Found: C, 54.16; H, 5.52; N, 9.19; Cl, 8.04; S, 6.92.

EXAMPLE 60

(2S-cis)-3-Acetyloxy-5-4,5-dihydro-1H-imidazol-2-yl)methyl]-2,3-dihydro-8-methoxy-2-(4-methoxyphenyl)-1,5-benzothiazepin-4-(5H)-one, monohydrochloride The title compound was prepared from (2S-cis)-5-[4,5-dihyro-1H-imidazol-2-yl)methyl]-2,3-d ihydro-3-hydroxy-8-methoxy-2-(4-methoxyphenyl)-1, 5-benzothiazepin-4(5H)-one (title compound of Example 59), following the procedures described in Example 54, m.p. 275° C. $[\alpha]_D = +65.19$ (c =1.0, methanol).

Analysis calculated for $C_{23}H_{25}N_3ClSO_5 \cdot HCl \cdot 0.93 H_2O$: C, 54.29; H, 5.52; N, 8.26; Cl, 6.97; S, 6.30. Found: C, 54.6B: H, 5.32 N, 7.72 Cl, 7.42: S, 5.95.

EXAMPLE 61

(cis)-1-[(4,5-Dihydro-1H-Imidazol-2-yl)methyl]-1, 3,4,5-tetrahydro-3-hydroxy-7-methylthio-4-(4-methoxyphenyl)-2H-1-benzazepin-2-one, monohydrochloride The title compound was prepared from (cis)-1,3,4,5-tetrahydro-3-hydroxy-7-methylthio-4-(4-methoxyphenyl)-2H-1-benzazepin-2-one following the procedures described in Example 43, m.p. 195°–198° C.

Analysis calculated for: $C_{22}H_{25}N_3O_3S \cdot HCl \cdot 0.64 H_2O$: C, 57.50; H, 5.98; N, 9.15; Cl, 7.72; S, 6.98. Found: C, 57.60; H, 6.19; N, 9.05; Cl, 7.63; S, 6.84.

EXAMPLE 62

(cis)-1-[(4,5-Dihydro-1H-imidazol-2-yl)methyl]-1,3,4,5-tetrahydro-3-hydroxy-7-methylsulfinyl-4-(4-methoxyphenyl)-2H-1-benzazepin-2-one, monohydrochloride

A.

(cis)-1,3,4,5-tetrahydro-3-hydroxy-7-methylsulfinyl-4-(4-methoxyphenyl)-2H-1-benzazepin-2-one A solution of (cis)-1,3,4,5-Tetrahydro-3-hydroxy-7-methylthio-4-(4-methoxyphenyl)-2H-1-benzazepin-2-one (1.0 g, 3.04 mmol) in dry methylene chloride (30 ml) at 5° C. was treated with m-chloroperoxybenzoic acid (0.615 g, 3.04 mmol). After 30 minutes, the reaction was complete and the reaction mixture was diluted with ethyl acetate, washed with saturated sodium hydrogen carbonate, water, and brine. The organic layer was filtered and concentrated in vacuo to give a solid residue (1.02×g). Trituration with hot ethyl acetate, cooling and filtration afforded the product (600 mg), m.p. 214° 14 216° C. The mother liquors were concentrated in vacuo and chromatographed on LPS-1 silica (methylene chloride/methanol). The product fractions were combined and concentrated in vacuo, and the residue crystallized from ethyl acetate to give an additional 200 mg of product.

B.

(cis)-1-[(4,5-Dihydro-1H-imidazol-2-yl)-methyl]-1,3,4,5-tetrahydro-3-hydroxy-7-methylsulfinyl-4-(4-methoxyphenyl)-2H-1-benzazepin-2-one, monohydrochloride The title B compound was prepared from title A compound using the procedures described in EXAMPLE 43, m.p. 195°–205° C.

Analysis calculated for $C_{22}H_{25}ClN_3O_4S \cdot 1.3 H_2O$: C, 54.21; H, 5.91; N, 8.62; S, 6.58; Cl, 7.27. Found: C, 54.48; H, 5.77; N, 8.35; S, 6.33; Cl, 7.62.

EXAMPLE 63

[3R-[1(S*),3α,4α]]-1,3,4,5-Tetrahydro-3-hydroxy-4-(4-methoxyphenyl)-1-(2-azetidinylmethyl)-6-(trifluoromethyl)-2H-1-benzazepin-2-one, fumarate (1:1) salt

A.
S-1-[(1,1-Dimethylethoxy)carbonyl]azetidine-2-carboxylic acid

Di-t-butyl dicarbonate (2.18 g, 9.9 mmol) was added in one portion to a stirred mixture of (L)-azetidine-2-carboxylic acid (1.0 g; 9.9 mmol), triethylamine (2.12 ml; 15.0 mmol), 10 ml of acetone and 10 ml of water. The resulting reaction mixture was stirred 4 hours at room temperature at which time the mixture was partitioned between ethyl acetate (100 ml) and water (100 ml). The aqueous layer was acidified to pH 3 with 10% citric acid solution. The resulting acidic mixture was extracted with 2×200 ml ethyl acetate and the combined organic extracts dried (magnesium sulfate) and concentrated to afford the title A compound (2.0 g) as a colorless oil.

B.
S-1-[(1,1-Dimethylethoxy)carbonyl]azetidine-2-carboxylic acid methyl ester A mixture of (S)-1-[(1,1-Dimethylethoxy)carbonyl]-azetidine-2-carboxylic acid (2.0 g; 9.9 mmol), potassium carbonate (6.9 g; 50.0 mmol), and methyliodide (6.25 ml; 100.0 mmol) in 20 ml of dimethylformamide was stirred under argon at room temperature for 1 d. The excess methyliodide was pumped into a dry ice cooled trap and the remaining mixture poured into water and extracted with 300 ml of ethyl ether. The organic extract was washed with 2×150 ml of brine, dried (magnesium sulfate) and concentrated to afford 1.85 g of the title B as a colorless liquid. $[α]_D = -114.8°$ (c = 2.5, chloroform).

C.
R,S-1-[(1,1-Dimethylethoxy)carbonyl]azetidine-2-carboxylic acid 1,1-dimethylethyl ester To a solution of S-1-[(1,1-Dimethylethoxy)carbonyl-azetidine-2-carboxylic acid methyl ester (1.83 g; 8.5 mmol) in 38 ml of t-butanol at room temperature was added 18.8 ml of a 1 M solution of potassium t-butoxide in tetrahydrofuran. The reaction mixture was stirred for 5 hours, at which time it was diluted with ml of ethyl ether. The resulting mixture was washed successively with 100 ml each of brine, 1 N hydrochloric acid, saturated sodium hydrogen carbonate and brine. The organic extracts were dried (magnesium sulfate) and concentrated to afford 1.63 g of the title C compound as a colorless liquid.

D.
R,S-1-[(1,1-Dimethylethoxy)carbonyl]azetidine-2-methanol

Lithium borohydride (0.23 g; 10.5 mmol) was added in one portion to a solution of (R,S)-1-(1,1-dimethylethoxy)carbonyl]-azetidine-2-carboxylic acid, 1,1-dimethylethyl ester (1.59 g; 6.19 mmol) in 20 ml of tetrahydrofuran at 0°. The reaction was allowed to warm to room temperature and stirred for 18 hours at which time it was partitioned between brine and ethyl acetate. The organic extracts were washed with 1 N hydrochloric acid and brine, dried (magnesium sulfate) and concentrated to afford 0.92 g of the title D compoun colorless oil. $[α]_D = 0$.

E.
R,S-1-[(1,1-Dimethylethoxy)carbonyl]azetidine methyl(4-methylbenzene)sulfonate A mixture of R,S-1-[(1,1-dimethylethoxy)carb azetidine-2-methanol (0.9 g; 4.9 mmol) and p-tolue fonyl chloride (1.87 g; 9.8 mmol) in 10 ml of py was stirred for 60 hours at room temperature at point an additional 0.5 g (2.6 mmol) of p-toluenesu chloride was added and the reaction stirred for an tional 2 hours. 10 ml of saturated sodium hyd carbonate was then added and the mixture stirred minutes after which it was partitioned between 1 of ethyl acetate and 100 ml of saturated sodium h gen carbonate. The organic layer was washed 2×70 ml of 1 N hydrochloric acid, 50 ml of satu sodium hydrogen carbonate, and 50 ml of brine, (magnesium sulfate) and concentrated. The crud due was purified by flash chromatography (5×1 4:1 hexanes ethyl acetate) to give 1.43 g of the t compound as a yellow oil.

F.
[3R-[1(S*),3α,4α]]-1,3,4,5-Tetrahydro-3-hydroxy methoxyphenyl)-1-[1-[(1,1-dimethylethoxy)carb ]azetidinyl-2-methyl]-6-(trifluoromethyl(-2H-1-i zazepin-2-one (6) and
3R-[(1,1-dimethylethoxy)carbonyl]azetidinyl-methyl]-6-(trifluoromethyl)-2H-1-benzazepin-2-

A mixture of R,S-1-[(1,1-Dimethylethoxy)carb azetidine-2-methyl (4-methylbenzene)sulfonate (0. 1.46 mmol), (3R-cis)-1,3,4,5-tetrahydro-3-hydrox methoxyphenyl)-2H-1-benzazepin-2-one (0.46 mmol) and cesium carbonate (0.977 g; 30.0 mmo ml of dimethylformamide was stirred at 60° C. hours at which time the reaction mixture was tioned between 100 ml of ethyl acetate and 100 water. The organic extracts were washed with 2× of water and 50 ml of brine and then dried (magn sulfate) and concentrated. The crude light-yellov due was purified and the isomers separated by chromatography (5×12 cm; 5 L 3:1 Hexanes:eth tate, 1 L 1:1 Hexanes:ethyl acetate) to give 0.2 g of [3R-[1(S*),3α,4α]]-1,3,4,5-tetrahydro-3-hydr (4-methoxyphenyl)-1-[1-[(1,1-dimethylethoxy)car bonyl]azetidinyl-2-methyl]-6-(trifluoromethyl)-2H benzazepin-2-one as a white foam along with 0. (34%) of [3R-[1(R*),3α,4α]]-1,3,4,5-tetrahy hydroxy-4-(4-methoxyphenyl)-1-[1[(1,1-dimethyle y)-carbonyl]azetidinyl-2-methyl]-6-(trifluorometh 2H-1-benzazepin-2-one also as a white foam, as v 0.15 g of mixed fractions.

G.
[3R-[(S*),3α,4α]]-1,3,4,5-Tetrahydro-3-hydroxy-methoxyphenyl)-1-(2-azetidinylmethyl)-6-(trifluoi thyl)-2H-1-benzazepin-2-one, fumarate (1:1) s.

A mixture of [3R-[1(S*),3α,4α]]-1,3,4,5-tetrahy hydroxy-4-(4-methoxyphenyl)-1-[1-[(1,   1-dime thoxy)carbonyl]azetidinyl-2-methyl]-6-(trifluorom thyl)-2H-1-benzazepin-2-one (0.55 g; 1.06 mmol) a ml of trifluoroacetic acid in 3.3 ml of methyl ch was stirred at room temperature for 2 hours. The tion mixture was concentrated at reduced pre Toluene was added and the mixture was reconcen to a yellow oil which was partitioned between acetate and 1 N sodium hydroxide. The organic extracts were washed with brine, dried (magnesium sulfate) and concentrated to afford 0.424 g of the crude free base which was purified by flash chromatography, m.p. 155° C. (soften), 162°–170° C. (dec). $[\alpha]_D = +62.8$ (c=0.50, methanol).

Analysis calculated for $C_{22}H_{25}N_2F_3O_3 \cdot C_4H_4O_4 \cdot 0.49$ $H_2O$. C, 57.26; H, 5.17; N, 5.14; F, 10.45. Found: C, 57.24; H, 5.05; N, 5.16; F, 10.61.

EXAMPLE 64

[3R-[1(R*),3α,4α]]-1,3,4,5-Tetrahydro-3-hydroxy-4-(4-methoxyphenyl)-1-(2-azetidinylmethyl)-6-(trifluoromethyl)-2H-1-benzazepin-2-one, fumarate (1:1) salt The title compound was prepared from [3R-[1(R*),3α,4α]]-1,3,4,5-tetrahydro-3-hydroxy-4-(4-methoxyphenyl)-1-[1-(1,1-dimethylethoxy)carbonyl]azetidinyl-2-methyl]-6-(trifluoromethyl)-2H-1-benzazepin-2-one, described in part F of EXAMPLE 63, using the procedures described in part G of Example 63, m.p. 112° C. (soften), 140°–146° C. (dec). $[\alpha]_D = +90.2°$ (c =0.55, methanol).

Analysis calculated for $C_{22}H_{23}N_2F_3O_3 \cdot C_4H_4O_4 0.99$ $H_2O$: C, 56.33; H, 5.27; N, 5.05; F, 10.28. Found: C, 56.21; H, 5.22; N, 5.17; F, 10.55.

EXAMPLE 65

(3R-cis)-1-[(1-methyl-4,5-Dihydro-imidazol-2-yl)methyl-3-hydroxy-4-(4-methoxyphenyl)-6-(trifluoromethyl)-2H-1-benzazepin-2-one

A.

(3R-cis)-1-(cyanomethyl)-3-hydroxy-4-(4-methoxyphenyl)-6-(trifluoromethyl)-2H-1-benzazepin-2-one To a solution of 0.60 g of sodium hydride (14.9 mmol of a 60% oil dispersion) in 150 ml of dry tetrahydrofuran was added 5.0 g of (3(R)-cis)-3-hydroxy-4-(4-methoxyphenyl)-6-trifluoromethyl)-2H-1-benzazepin-2-one. The solution was stirred for 15 minutes at room temperature, cooled to 0° C. and a solution of 1.03 ml of iodoacetonitrile (14.2 mmol) in 10 ml of dry tetrahydrofuran was added dropwise. The solution was allowed to come to room temperature over 2 hours and was partitioned between water and ether. The aqueous layer was washed with ether and the combined ether extracts were washed with brine and dried (magnesium sulfate). The solution was evaporated to about 20 ml, 10 ml of hexane were added and the solution was chilled to afford 0.74 g of (3R-cis)-1-(cyanomethyl)-3-hydroxy-4-(4-methoxyphenyl)-6-(trifluoromethyl)-2H-1-benzazepin-2-one as a light yellow crystalline solid. The mother liquor afforded an additional 2.04 g of product.

B.

(3R-cis)-1-[(1-Methyl-4,5-Dihydroimidazol-2-yl)methyl]-3-hydroxy-4-(4-methoxyphenyl)-6-(trifluoromethyl)-2H-1-benzazepin-2-one Gaseous hydrogen chloride was bubbled through a suspension of 1.95 g of (3R-cis)-1-cyanomethyl)-3-hydroxy-4-(4-methoxyphenyl)-6-(trifluoromethyl)-2H-1-benzazepin-2-one (5.0 mmol) in 20 ml of ether containing 0.31 ml of absolute ethanol (5.24 mmol) at 0° C. until the solid dissolved. The solution was capped and stored at 5° C. for 4 days and at −20° C. for 6 days. The ether was decanted from the thick oily residue which had settled and dry ether was added to the residue to afford a white solid. The ether was decanted and the white solid was washed with ether. The white solid was dissolved in 25 ml od dimethylformamide and 12.5 ml of this solution was added dropwise to a solution of 0° C. of 0.33 ml of N-methylethylenediamine (3.75 mmol) in 5 ml od dry dimethylformamide. The solution was stirred at room temperature for 90 minutes, aqueous potassium carbonate was added and the solution was extracted twice with ether. The combined ether extracts were washed twice with water, once with brine, dried (potassium carbonate) and evaporated to afford 0.77 g of white solid. The solid was dissolved in ether and hydrogen chloride saturated ether was added to afford a white solid. The solid was filtered, rinsed twice with ether and dissolved in a homogeneous mixture of aqueous potassium carbonate, ether and dioxane. Ether was added to achieve phase separation, the aqueous layer was washed with additional ether and the combined organic extracts were washed with brine, dried (potassium carbonate) and evaporated to afford 0.66 g of white solid. The solid was chromatographed with 5% methanol/dichloromethane on three silica preparative thin layer chromatography plates which had been previously eluted with 5% triethylamine/dichloromethane. The main band was excised and extracted twice with 10% methanol/dichloromethane and the combined solutions were evaporated to afford 0.27 g of light yellow foamy solid. The solid was dissolved in ethyl acetate and hydrogen chloride-saturated ether was added to afford a waxy solid. The solution was evaporated and chased with ether. The solid was dissolved in 20 ml of 1:1 methanol:isopropyl ether and 150 ml of isopropyl ether was added. The solid was filtered and air dried to afford 235 mg of (3R-cis)-1-[(1-methyl-4,5-dihydro-imidazol-2-yl)methyl]-3-hydroxy-4-(4-methoxyphenyl)-6-(trifluoromethyl)-2H-1-benzazepin-2-one as a tan solid, m.p. >240° C. $[\alpha]_D + 98.2$ (c =1, methanol).

Analysis calculated for $C_{23}H_{25}N_3O_3F_3Cl \cdot 1.70$ $H_2O$: C, 53.68; H, 5.56; N, 8.16; F, 11.07; Cl, 6.89. Found: C, 54.08; H, 5.46; N, 7.90; F, 10.68; Cl, 6.90.

EXAMPLE 66

(3R-cis)-1-[(4,5-Dihydro-1H-imidazol-2-yl)methyl]-1,3,4,5-tetrahydro-3-hydroxy-6-chloro-4-(4-methoxyphenyl)-2H-1benzaxzepin-2-one, monohydrochloride

A.

(cis)-1,3,4,5-Tetrahydro-3-[(2-carboxyphenyl)carboxyl]-6-chloro-4-(4-methoxyphenyl)-2H-1-benzazepin-2-one, A stirred suspension of (cis)-1,3,4,5-tetrahydr-3-hydroxy-6-chloro-4-(4methxoyphenyl)-2H-1-benzazepin-2-one, prepared by the procedures of Example 61, in dichloromethane (100 ml) was treated with a solution of triethylamine (5.55 g, 55 mmol) in dichloromethane (50 ml), followed by dimethylaminopyridine (1.0 g) and phthalic anhydride (8.2 g, 55 mmol). The solids rapidly dissolved and jthe resulting solution was stirred for two hours at room temperature. The mixture was treated portion wise with 1 N hydrochloric acid (83 ml) to give a heavy precipitate. After stirring and cooling for 30 minutes, the product was filtered, washed with 25 ml of water (five times) and dried to give the title A product (22.58 g), m.p. 165°–167° C. After recrystallization form acetonitrile, a sample of this material melted at 220°–222 C.

B.
(3R-cis)-1,3,4,5-Tetrahydro-3-[(2-carboxyphenyl)carboxyl]-6chloro-4-(4-methoxyphenyl)-2H-1-benzazepin-2-one, benzazepin-2-one, S-α-methylbenzylamine salt A stirred suspension of (cis)-1,3,4,5-tetrahydro-3-[(2-carboxyphenyl)carboxyl]-6-chloro-4-(4methoxyphenyl)-2H-1-benzazepin-2-one (22.17 g, 47.5 mmol) in methznol (250 ml) was warmed and treated wit a solution of S-α-methylbenzylamine (5.80 g, 47.5 mmol) in methanol (50 ml). The mixture was heated to reflux to give a solution which then began to crystallize. After standing overnight at room temperature, the crystalline product was filtered, washed with methanol (3×20 ml) and dried to give the title B compound (12.03 g), m.p. 160° C. $[\alpha]_D = -15.5°$ (c=1.0, HOAc).

C.
(3R-cis)-1,3,4,5-tetrahydro-3-hydroxy-6-chloro-4-(4-methoxyphenyl)-2H-1-benzazepin-2-one To a stireed solution of lithium hydroxide water (3.40 g, 81 mmol) in water (113 ml) was added the title B compound (11.85 g, 20.5 mmol). The resulting solution was treated with methanol (11 ml) and heated to reflux. A heavy precipitate separated. This suspension was heated at 60° to 70° C. for one hour, diluted with water (100 ml), cooled and stirred for 2 hours. The solid was filtered, washed with water and dried to give the title C compound as a colorless solid (5.76 g), m.p. 191°–193° C. $[\alpha]_D = +83.4°$ (c=1.0, HOAc)

D.
(3R-cis)-1-(4,5-Dihydro-1H-imidazol-2-yl)methyl]-1,3,4,5-tetrahydro-3-hydroxy-6-chloro-4-(4-methoxyphenyl)-2H-1-benzazepin-2-one, monohydrochloride The title D compound was prepared from the title C compound following procedures described in Example 43, m.p. 196°–200° C. $[\alpha]_D = +80.4°$ (c=1.0, methanol).

Analysis calculated for $C_{21}H_{22}Cl_2N_3O_3 \cdot 1.06 H_2O$: C, 55.38; H, 5.56; N, 9.23; Cl, 15.57. Found: C, 54.98; H, 5.15; N, 8.87; Cl, 15.95.

EXAMPLE 67
[3R-[1(R*),3α,4α]]-3-Acetyloxy-1,3,4,5-tetrahydro-4-(4-methoxyphenyl)-1-(2-pyrrolidinylmethyl)-6-trifluoromethyl-2H-1-benzazepin-2-one, monohydrochloride The title compound was prepared from R-1-(t-butoxycarbonyl)-2-[(4-methylphenylsulfonyloxy)methyl]-pyrrolidine and (3R-cis)-1,3,4,5-tetrahydro-3-hydroxy-4-(4-methoxyphenyl)-6-trifluoromethyl-2H-1-benzazepin-2-one as described in the procedures of Example 46, m.p. 153°–157° C. $[\alpha]_D = +104.8°$ (c=1.0, methanol).

Analysis calculated for $C_{25}H_{27}N_2N_2O_4F_3 \cdot HCl \cdot 0.32 H_2O$: C, 57.88; H, 5.57; N, 5.40; Cl, 6.83; F, 10.99. Found: C, 57.78; H, 5.89; N, 5.50; Cl, 6.88; F, 10.61.

What is claimed is:
1. A compound having the formula

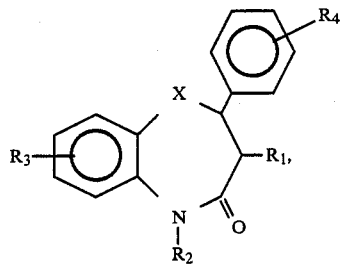

and the pharmaceutically acceptable salts thereof, wherein
X is —CH₂— or —S—;
R₁ is

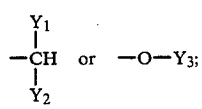

when X is —CH₂—, R₂ is

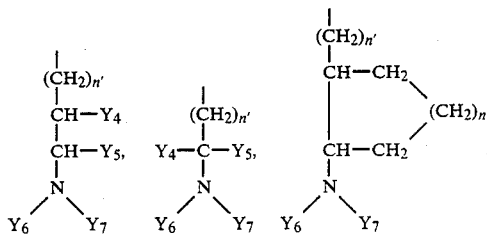

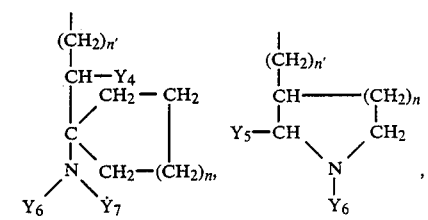

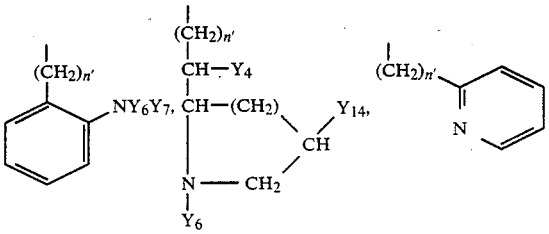

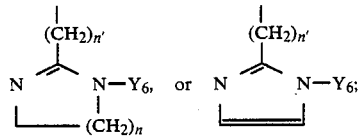

when X is —S—, R₂ is $$\begin{array}{c} | \\ (CH_2)_{n'} \\ | \\ CH-CH_2 \\ | \qquad \diagdown (CH_2)_n \\ CH-CH_2 \diagup \\ | \\ N \\ \diagup \diagdown \\ Y_6 \quad Y_7 \end{array}$$

$$\begin{array}{cc} \begin{array}{c} | \\ (CH_2)_{n'} \\ | \\ CH-Y_4 \\ | \quad CH_2-CH_2 \\ C \diagup \\ | \diagdown \\ N \quad CH_2-(CH_2)_{n'} \\ \diagup \diagdown \\ Y_6 \quad Y_7 \end{array} & \begin{array}{c} | \\ (CH_2)_{n'} \\ | \\ CH\text{———}(CH_2)_n \\ | \qquad \diagdown \\ Y_5-CH \qquad CH_2 \\ \diagdown \diagup \\ N \\ | \\ Y_6 \end{array} \end{array}$$

$$\begin{array}{ccc} \begin{array}{c} (CH_2)_{n'} \\ | \\ \text{Ph-}NY_6Y_7 \end{array} & \begin{array}{c} | \\ (CH_2)_{n'} \\ | \\ CH-Y_4 \\ | \\ CH-(CH_2) \quad Y_{14}, \\ | \qquad \diagdown \\ \qquad CH \\ N\text{———}CH_2 \\ | \\ Y_6 \end{array} & \begin{array}{c} (CH_2)_{n'} \\ | \\ \text{pyridinyl} \end{array} \end{array}$$

$$\begin{array}{cc} \begin{array}{c} | \\ (CH_2)_{n'} \\ | \\ N \qquad N-Y_6, \\ \diagdown \quad | \\ \diagdown (CH_2)_n \end{array} & \begin{array}{c} | \\ (CH_2)_{n'} \\ | \\ N \qquad N-Y_6; \\ \diagup\diagdown\diagup\diagdown \end{array} \end{array}$$

$R_3$ and $R_4$ are each independently hydrogen, halogen, alkyl, alkoxy, aryloxy, arylalkoxy, arylalkyl, cyano, hydroxy, alkanoyloxy, $$-O-\underset{\underset{O}{\|}}{C}-NY_8Y_9,$$

fluoro substituted alkoxy, fluoro substituted alkyl, (cycloalkyl)alkoxy, $-NO_2$, $-NY_{10}Y_{11}$, $-S(O)_m$alkyl, $-S(O)_m$aryl, $$-\underset{\underset{O}{\|}}{C}-Y_{12} \quad \text{or} \quad -O-\underset{\underset{O}{\|}}{C}-Y_{13};$$

n or n' are independently 0, 1, 2 or 3; m is 0, 1 or 2;
$Y_1$ and $Y_2$ are independently hydrogen or alkyl, $Y_1$ is hydrogen and $Y_2$ is alkenyl, alkynyl, aryl, heteroaryl, or cycloalkyl, or $Y_1$ and $Y_2$ together with the carbon atom to which they are attached are cycloalkyl;
$Y_3$ is hydrogen, alkyl, alkanoyl, alkenyl, arylcarbonyl, heteroarylcarbonyl, or $$-\underset{\underset{O}{\|}}{C}-NY_8Y_9;$$

$Y_4$ and $Y_5$ are each independently hydrogen, alkyl, aryl or arylalkyl, provided that when both are present they are not both hydrogen, and provided further that when both are attached to the same carbon atom neither of them is hydrogen, $Y_6$ and $Y_7$ are each independently hydrongen, alkyl, cycloalkyl or arylalkyl or $Y_6$ and $Y_7$ together with the nitrogen atom to which they are attached are azetidinyl, pyrrolidinyl, peperidinyl, or morpholinyl;

$Y_8$ and $Y_9$ are each independently hydrogen, alkyl, aryl or heteroaryl, or $Y_8$ and $Y_9$ together with the nitrogen atom to which they are attached are pyrrolidinyl, piperidinyl or morpholinyl;

$Y_{10}$ and $Y_{11}$ are each independently hydrogen, alkyl, alkanoyl, arylcarbonyl, heteroarylcarbonyl, or $$-\underset{\underset{O}{\|}}{C}-NY_8Y_9;$$

$Y_{12}$ is hydroxy, alkoxy, aryloxy, amino, alkylamino or dialkylamino;

$Y_{13}$ is alkyl alkoxy or aryloxy; and, $Y_{14}$ is hydrogen, hydroxy, alkoxy, aryloxy or arylalkoxy. wherein the terms "alkyl" and "alkoxy" refer to both straight and branched chain groups having 1 to 10 carbon atoms;

the term "alkenyl" refers to both straight and branched chain groups having 2 to 10 carbon atoms;

the term "aryl" refers to phenyl and substituted phenyl wherein said substituents may be 1, 2 or 3 groups independently selected from amino, alkylamino, dialkylamino, nitro, halogen, hydroxyl, trifluoromethyl, alkyl of 1 to 4 carbon atoms, alkoxy of 1 to 4 carbon atoms, alkylthio of 1 to 4 carbon atoms, alkanoyloxy, carbonyl, or carboxyl;

the term "alkanoyl" refers to groups having the formula $$\text{alkyl-}\underset{\underset{O}{\|}}{C}-$$

having 2 to 11 carbon atoms;

the term "heteroaryl" refers to an aromatic heterocyclic group selected from pyridinyl, pyrrolyl, imidazolyl, furyl, thienyl, oxazolyl and thiazolyl;

the term "cycloalkyl" refers to groups having 3,4, 5, 6 or 7 carbon atoms;

the term "halogen" refers to fluorine, chlorine, bromine and iodine; and, the terms "fluoro substituted alkyl" and "fluoro substituted alkoxy" refer to alkyl and alkoxy groups in which one or more hydrogens have been replaced by fluorine atoms.

2. A compound in accordance with claim 1 wherein $R_1$ is $$-\underset{\underset{Y_2}{|}}{\overset{\overset{Y_1}{|}}{CH.}}$$

3. A compound in accordance with claim 1 wherein $R_1$ is $-O-Y_3$.

4. A compound in accordance with claim 1 wherein $R_2$ is

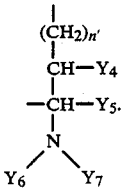

5. A compound in accordance with claim 1 wherein $R_2$ is

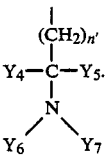

6. A compound in accordance with claim 1 wherein $R_2$ is

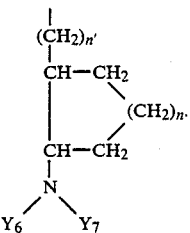

7. A compound in accordance with claim 1 wherein $R_2$ is

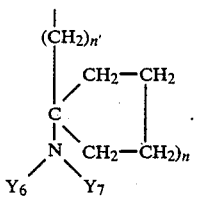

8. A compound in accordance with claim 1 wherein $R_2$ is

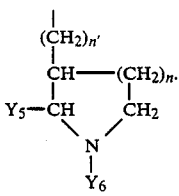

9. A compound in accordance with claim 1 wherein $R_2$ is

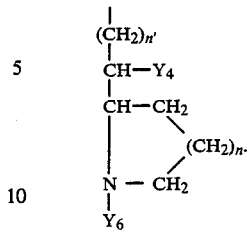

10. A compound in accordance with claim 1 wherein $R_3$ is methoxy or trifluoromethyl, $R_4$ is located in the 4-position of the phenyl ring to which it is attached, and $R_4$ is alkoxy.

11. A compound in accordance with claim 1 wherein $R_4$ is 4-methoxy.

12. A compound in accordance with claim 1 wherein $R_3$ is methoxy or trifluoromethyl.

13. The compound in accordance with claim 1, [3R-[1(S*),3α,4α]]-3-(acetyloxy)-1,3,4,5-tetrahydro-4-(4-methoxyphenyl)-1-(2-pyrrolidinylmethyl)-6-(trifluoromethyl)-2H-1-benzazepin-2-one or a pharmaceutically acceptable salt thereof.

14. The compound in accordance with claim 1, [3R-[1(S*),3α,4α)-1,3,4,5-tetrahydro-3-hydroxy-4-(4-methoxyphenyl)-1-(2-pyrrolidinylmethyl)-6-(trifluoromethyl)-2H-1-benzazepin-2-one, or a pharmaceutically acceptable salt thereof.

15. The compound in accordance with claim 1, [3R-[1(S*),3α,4α]]-6-chloro-1,3,4,5-tetrahydro-3-hydroxy-4-(4-methoxyphenyl)-1-(2-pyrrolidinylmethyl)-2H-1-benzazepin-2-one.

16. The compound in accordance with claim 1, [3R-[1(S*),3α,4α]]-3-(acetyloxy)-6-chloro-1,3,4,5-tetrahydro-4-(4-methoxyphenyl)-1-(2-pyrrolidinylmethyl)-2H-1-benzazepin-2-one.

17. The compound in accordance with claim 1, [3R-[1(2S*),3α,4α]]-1-[(2-dimethylamino)-1-phenylpropyl]-1,3,4,5-tetrahydro-3-hydroxy-4-(4-methoxyphenyl)-6-(trifluoromethyl)-2H-1-benzazepin-2-one, isomer B, monohydrochloride.

18. The compound in accordance with claim 1, (3(R)-cis)-1-[2-(Dimethylamino)-1-phenylethyl]-1,3,4,5-tetrahydro-3-hydroxy-4-(4-methoxyphenyl)-6-(trifluoromethyl)-2H-1-benzazepin-2-one, isomer B, monohydrochloride.

19. The compound in accordance with claim 1, [3(R)-[1(2S*),3α,4α]]-1-2-(Dimethylamino)-1-phenylpropyl-1,3,4,5-tetrahydro-3-hydroxy-4-(4-methoxyphenyl)-6-(trifluoromethyl)-2H-1-benzazepin-2-one, isomer A, monohydrochloride.

20. The compound in accordance with claim 1, [3R-[1(R*),3α,4α]-1,3,4,5-tetrahydro-3-hydroxy-4-(4-methoxyphenyl)-1-(3-pyrrolidinyl)-6-(trifluoromethyl)-2H-1-benzazepin-2-one, furmarate (1:1) salt.

21. The compound in accordance with claim 1, [3R-[1(2S*,4R*),3α,4α]]-1,3,4,5-tetrahydro-3-hydroxy-4-(4-methoxyphenyl)-1-[[4-(phenylmethoxy)-2-pyrrolidinyl]methyl]-6-(trifluoromethyl)-2H-1-benzazepin-2-one, monohydrochloride.

22. The compound in accordance with claim 1, [3R--[1(2S*,4R*),3α,4α]]-1,3,4,5-tetrahydro-3-hydroxy-1-[(4-hydroxy-2-pyrrolidinyl)methyl]-4-(4-methoxyphenyl)-6-(trifluoromethyl)-2H-1-benzazepin-2-one, monohydrochloride.

23. The compound in accordance with claim 1, [3R-[1(2S*,4S*),3α,4α]]-1,3,4,5-Tetrahydro-3-hydroxy-1-[(4-hydroxy-2-pyrrolidinyl)methyl]-4-(4-methoxyphenyl)-6-(trifluoromethyl)-2H-1-benzazepin-2-one, monohydrochloride.

24. The compound in accordance with claim 1, (3R-cis)-1-[(4,5-dihydro-1H-imidazol-2-yl)methyl]-1,3,4,5-tetrahydro-3-hydroxy-4-(4-methoxyphenyl)-6(trifluoromethyl)-2H-1-benzazepin-2-one, monohydrochloride.

25. The compound in accordance with claim 1, [2S-[2α,3α,5(R*)-3-(acetyloxy)-2,3-dihydro-8-methoxy-2-(4-methoxyphenyl)-5-(2-pyrrolidinylmethyl)-1,5-benzothiazepin-4(5H)-one, monohydrochloride.

26. The compound in accordance with claim 1, 2S-[2α,3α,5(R*)]-2,3-dihydro-2(4-methoxyphenyl)-3-(2-methyl-1-oxopropoxy)-5-(2-pyrrolidinylmethyl)-1,5-benzothiazepin-4(5H)-one, monohydrochloride.

27. The compound in accordance with claim 1, 3R-[1(S*),3α,4α]]-3-(acetyloxy)-1,3,4,5-tetrahydro-7-methoxy-4-(4-methoxyphenyl)-1-(2-pyrrolidinylmethyl)-2H-1-benzazepin-2-one, monohydrochloride.

28. The compound in accordance with claim 1, (3R-cis)-3-(Acetyloxy)-1-[(4,5-dihydro-1H-imidazol-2-yl)methyl]-1,3,4,5-tetrahydro-4-(4-methoxyphenyl)-6-(trifluoromethyl)-2H-1-benzazepin-2-one, monohydrochloride.

29. The compound in accordance with claim 1, (3R-cis)-1-[(4,5-Dihydro-1H-imidazol-2-yl)methyl]-1,3,4,5-tetrahydro-3-hydroxy-7-methoxy-4-(4-methoxyphenyl)-2H-1-benzazepin-2-one, monohydrochloride.

30. The compound in accordance with claim 1, (3R-cis)-3-(Acetyloxy)-1-[(4,5-dihydro-1H-imidazol2-yl)methyl-1,3,4,5-tetrahydro-7-methoxy-4-(4-methoxyphenyl)-2H-1-benzazepin-2-one, monohydrochloride.

31. The compound in accordance with claim 1, 3R-[1(S*),3α,4α]]-1,3,4-5-Tetrahydro-3-hydroxy-7-methoxy-4-(4-methoxyphenyl)-1-(2-pyrrolidinylmethyl)-2H-1-benzazepin-2-one, monohydrochloride.

32. The compound in accordance with claim 1, 2S-[2α,3α,5(R*)]]-2,3-dihydro-3-hydroxy-8-methoxy-2-(4-methoxyphenyl)-5-(2-pyrrolidinylmethyl)-1,5-benzothiazepin-4-(5H)-one, monohydrochloride.

33. The compound in accordance with claim 1, (2S-cis)-5-[4,5-Dihydro-1H-imidazol-2-yl)methyl]-2,3-dihydro-3-hydroxy-8-methoxy-2-(4-methoxyphenyl)-1,5-benzothiazepin-4-(5H)-one, monohydrochloride.

34. The compound in accordance with claim 1, (2S-czs)-3-Acetyloxy-5-[4,5-dihydro-1H-imidazol-2yl)methyl]-2,3-dihydro-8-methoxy-2-(4-methoxyphenyl)-1,5-benzothiazepin-4-(5H)-one, monohydrochloride.

35. The compound in accordance with claim 1, (cis)-1-[(4,5-Dihydro-1H-imidazol-2-yl)methyl]-1,3,4,5-tetrahydro-3-hydroxy-7-methyl-4-(4-methoxyphenyl)-2H-1-benzazepin-2-one, monohydrochloride.

36. The compound in accordance with claim 1, (cis)-1-[(4,5-Dihydro-1H-imidazol-2-yl)methyl]-1,3,4,5-tetrahydro-3-hydroxy-7-methylsulfinyl-4-(4-methoxyphenyl)-2H-1-benzazepin-2-one, monohydrochloride.

37. The compound in accordance with claim 1, [3R-[1(S*),3α,4α]]-1,3,4,5-Tetrahydro-3-hydroxy-4-(4-methoxyphenyl)-1-(2-azetidinylmethyl)-6-(trifluoromethyl)-2H-1-benzazepin-2-one, fumarate (1:1) salt.

38. The compound in accordance with claim 1, [3R-[1(R*),3α,4α]]-1,3,4,5-Tetrahydro-3-hydroxy-4-(4-methoxyphenyl)-1-(2-azetidinylmethyl]-6-(trifluoromethyl)-2H-1-benzazepin-2-one, fumarate (1:1) salt.

39. The compound in accordance with claim 1, (3(R)-cis)-1-[(1-methyl-4,5-dihydro-imidazol-2-yl)-methyl-3-hydroxy-4-(4-methoxyphenyl)-6-(trifluoro- methyl)-2H-1-benzazepine-2-one.

40. The compound in accordance with claim 1, (3R-cis)-1-[(4,5-Dihydro-1H-imidazol-2-yl)methyl]-1,3,4,5-tetrahydro-3-hydroxy-6-chloro-4-(4-methoxyphenyl)-2H-1-benzazepin-2-one, monohydrochloride.

41. The compound in accordance with claim 1, [3R-[1(R*),3α,4α]]-3-Acetyloxy-1,3,4,5-tetrahydro-4-(4-methoxyphenyl)-1-(2-pyrrolidinylmethyl)-6-tri- fluoromethyl-2H-1-benzazepin-2-one, monohydrochloride.

42. A method of treating a host having a disease susceptible to treatment with a vasodilator which comprises administering to said host an effective amount of a compound having the formula

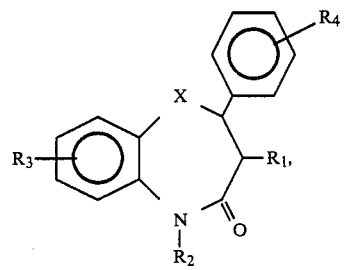

and the pharmaceutically acceptable salts thereof, wherein

X is —CH$_2$—or —S—;

R$_1$ is

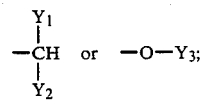

when X is —C$_2$2—, R$_2$ is

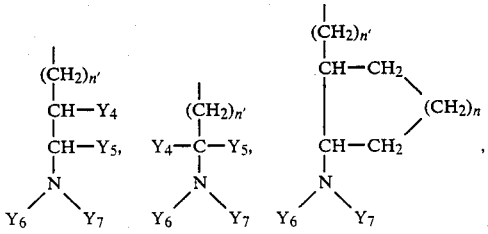

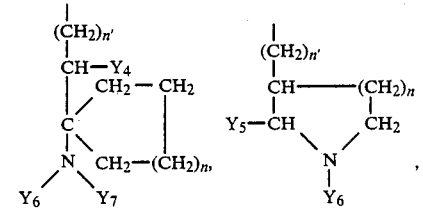

-continued

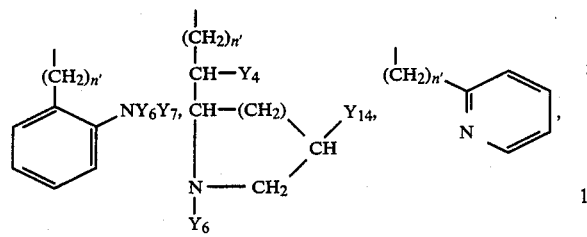

when X is —S—, R₂ is

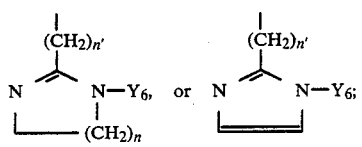

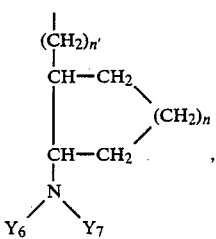

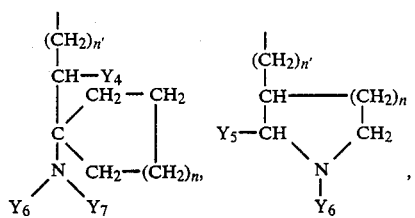

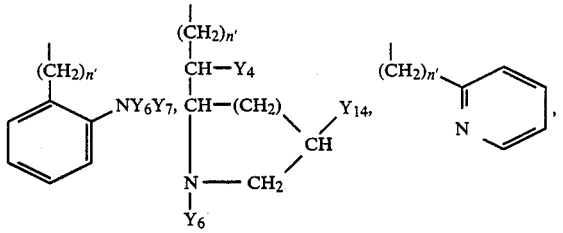

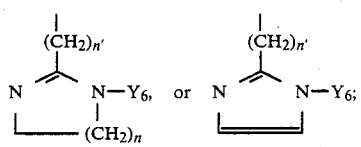

R₃ and R₄ are each independently hydrogen halogen, alkyl, alkoxy, aryloxy, arylalkoxy, arylalkyl,-cyano, hydroxy, alkanoyloxy,

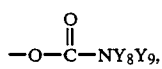

fluoro substituted alkoxy, fluoro substituted alkyl, (cycloalkyl)alkoxy, —NO₂, —NY₁₀Y₁₁, —S(O)$_m$aryl,

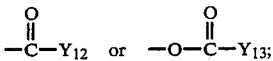

n or n' are independently 0, 1, 2 or 3;
m is 0, 1 or 2;
Y₁ and Y₂ are independently hydrogen or alkyl, Y₁ is hydrogen and Y₂ is alkenyl, alkynyl, aryl, heteroaryl, or cycloalkyl, or Y1 and Y2 together with the carbon atom to which they are attached are cycloalkyl;
Y₃ is hydrogen, alkyl, alkanoyl, alkenyl, arylcarbonyl, heteroarylcarbonyl, or

Y₄ and Y₅ are each independently hydrogen, alkyl, aryl or arylalkyl, provided that when both are present they are not both hydrogen, and provided further that when both are attached to the same carbon atom neither of them is hydrogen;
Y₆ and Y₇ are each independently hydrogen, alkyl, cycloalkyl or arylalkyl or Y₆ and Y₇ together with the nitrogen atom to which they are attached are azetidinyl, pyrrolidinyl, piperidinyl, or morpholinyl;
Y₈ and Y₉ are each independently hydrogen, alkyl, aryl or heteroaryl, or Y₈ and Y₉ together with the nitrogen atom to which they are attached are pyrrolidinyl, piperidinyl or morpholinyl;
Y₁₀ and Y₁₁ are each independently hydrogen, alkyl, alkanoyl, arylcarbonyl, heteroarylcarbonyl, or

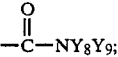

Y₁₂ is hydroxy, alkoxy, aryloxy, amino, alkylamino or dialkylamino;
Y₁₃ is alkyl, alkoxy or aryloxy; and,
Y₁₄ is hydrogen, hydroxy, alkoxy, aryloxy or arylalkoxy. wherein
the terms "alkyl" and "alkoxy" refer to both straight and branched chain groups having 1 to 10 carbon atoms;
the term "alkenyl" refers to both straight and branched chain groups having 2 to 10 carbon atoms;
the term "aryl" refers to phenyl and substituted phenyl wherein said substituents may be 1, 2 or 3 groups independently selected from amino, alkylamino, dialkylamino, nitro, halogen, hydroxyl, trifluoromethyl, alkyl of 1 to 4 carbon atoms, alkoxy of 1 to 4 carbon atoms, alkylthio of 1 to 4 Carbon atoms, alkanoyloxy, carbonyl, or carboxyl;
the term "alkanoyl" refers to groups having the formula

having 2 to 11 carbon atoms;
the term "heteroaryl" refers to an aromatic heterocyclic group selected from pyridinyl, pyrrolyl, imidazolyl, furyl, thienyl, oxazolyl and thiazolyl;

the term "cycloaalkyl" refers to groups having 3, 4, 5, 6 or 7 carbon atoms;

the term "halogen" refers to fluorine, chlorine, bromine and iodine; and, the term "fluoro substituted alkyl" and "fluoro substituted alkoxy" refer to alkyl and alkoxy groups in which one or more hydrogens have been replaced by fluorine atoms.

43. A compound having the formula

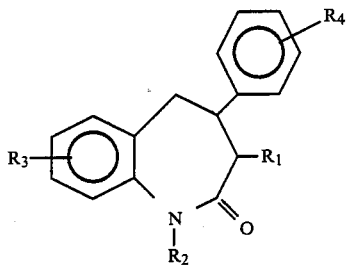

or a pharmaceutically acceptable salt thereof, wherein R₁ is

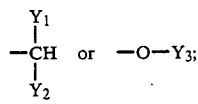

R₂ is

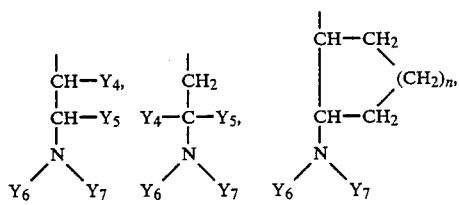

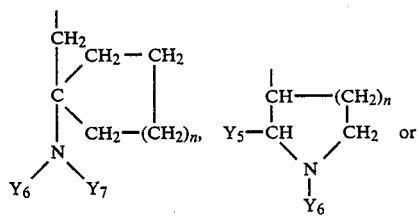

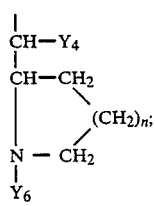

R₃ and R₄ are each independently hydrogen, halogen, alkyl, alkoxy, aryloxy, arylalkoxy, diarylalkoxy, arylalkyl, cyano, hydroxy, alkanoyloxy,

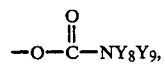

fluoro substituted alkoxy, fluoro substituted alkyl, (cycloalkyl)alkoxy, —NO₂, —NY₁₀Y₁₁, —S(O)ₘalkyl, —S(O)ₘaryl,

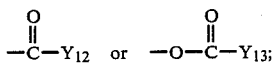

n is 0, 1, 2 or 3;

m is 0, 1 or 2;

Y₁ and Y₂ are each hydrogen or alkyl, Y₁ is hydrogen and Y₂ is alkenyl, alkynyl, aryl, heteroaryl, or cycloalkyl, or Y₁ and Y₂ together with the carbon atom to which they are attached are cycloalkyl;

Y₃ is hydrogen, alkyl, alkanoyl, alkenyl, arylcarbonyl, heteroarylcarbonyl, or

Y₄ and Y₅ are each independently hydrogen, alkyl, aryl or arylalkyl, provided that when both are present they are not both hydrogen, and provided further that when both are attached to the same carbon atom neither of them is hydrogen;

Y₆ and Y₇ are each independently hydrogen, alkyl, cycloalkyl or arylalkyl or Y₆ and Y₇ together with the nitrogen atom to which they are attached are azetidinyl, pyrrolidinyl, piperidinyl, or morpholinyl;

Y₈ and Y₉ are each independently hydrogen, alkyl, aryl or heteroaryl, or Y₈ and Y₉ together with the nitrogen atom to which they are attached are pyrrolidinyl, piperidinyl or morpholinyl;

Y₁₀ and Y₁₁ are each independently hydrogen, alkyl, alkanoyl, arylcarbonyl, heteroarylcarbonyl, or

Y₁₂ is hydroxy, alkoxy, aryloxy, amino, alkylamino or dialkylamino; and

Y₁₃ is alkyl, alkoxy or aryloxy. wherein the terms "alkyl" and "alkoxy" refer to both straight and branched chain groups having 1 to 10 carbon atoms;

the term "alkenyl" refers to both straight and branched chain groups having 2 to 10 carbon atoms;

the term "aryl" refers to phenyl and substituted phenyl wherein said substituents may be 1, 2 or 3 groups independently selected from amino, alkylamino, dialkylamino, nitro, halogen, hydroxyl, trifluoromethyl, alkyl of 1 to 4 carbon atoms, alkoxy of 1 to 4 carbon atoms, alkylthio of 1 to 4 carbon atoms, alkanoyloxy. carbonyl, or carboxyl;

the term "alkanoyl" refers to groups having the formula

having 2 to 11 carbon atoms;

the term "heteroaryl" refers to an aromatic heterocyclic group selected from pyridinyl, pyrrolyl, imidazolyl, furyl, thienyl, oxazolyl and thiazolyl;

the term "cycloalkyl" refers to groups having 3,4, 5, 6 or 7 carbon atoms;

the term "halogen" refers to fluorine, chlorine, bromine and iodine; and, the term "fluoro substituted alkyl" and "fluoro substituted alkoxy" refer to alkyl and alkoxy groups in which one or more hydrogens have been replaced by fluorine atoms.

* * * * *

UNITED STATES PATENT AND TRADEMARK OFFICE
CERTIFICATE OF CORRECTION

PATENT NO. : 4,902,684

DATED : February 20, 1990

INVENTOR(S) : D. M. Floyd et al.

It is certified that error appears in the above-identified patent and that said Letters Patent is hereby corrected as shown below:

Column 3, line 35, insert --hydrogen-- after "$Y_{14}$ is";

Column 78, line 9, "peperidinyl" should be --piperidinyl--;

Column 81, lines 15 and 16, insert brackets around "2S-[2α,3α,5(R*)]";

Column 81, line 19, "3R-" should be --[3R- --;

Column 81, line 36, "3R-" should be --[3R- --;

Column 81, line 40, "2S-" should be --[2S- --;

Column 81, line 50, "czs" should be --cis--;

Column 82, line 2, "methyl-3-" should be --methyl]-3- --;

UNITED STATES PATENT AND TRADEMARK OFFICE
CERTIFICATE OF CORRECTION

PATENT NO. : 4,902,684

DATED : February 20, 1990

INVENTOR(S) : D.M. Floyd, et al

It is certified that error appears in the above-identified patent and that said Letters Patent is hereby corrected as shown below:

Column 82, line 45, "-$C_2$2-" should be -- -$CH_2$- --;

Column 83, line 60, insert a comma after "hydrogen";

Column 83, line 67, insert -- -$S(O)_m$alkyl-- after "-$NY_{10}Y_{11}$,";

Column 84, line 10, "Y1 and Y2" should be --$Y_1$ and $Y_2$--;

Column 86, line 45, "alkyll" should be --alkyl--.

Signed and Sealed this

Twenty-seventh Day of August, 1991

Attest:

HARRY F. MANBECK, JR.

*Attesting Officer*           *Commissioner of Patents and Trademarks*